US012799189B2

(12) United States Patent
Cho et al.

(10) Patent No.: US 12,799,189 B2
(45) Date of Patent: Nov. 17, 2026

(54) HUMAN CXCLI6 ANTIBODIES AND THE USE THEREOF

(71) Applicant: CELLUS, INC., Daegu (KR)

(72) Inventors: Sun Wook Cho, Daegu (KR); Seong Keun Kim, Daegu (KR)

(73) Assignee: CELLUS, INC., Daegu (KR)

( * ) Notice: Subject to any disclaimer, the term of this patent is extended or adjusted under 35 U.S.C. 154(b) by 317 days.

(21) Appl. No.: 18/575,044

(22) PCT Filed: Nov. 22, 2022

(86) PCT No.: PCT/IB2022/061294

§ 371 (c)(1),
(2) Date: Dec. 28, 2023

(87) PCT Pub. No.: WO2023/094995

PCT Pub. Date: Jun. 1, 2023

(65) Prior Publication Data

US 2024/0327509 A1 Oct. 3, 2024

(30) Foreign Application Priority Data

Nov. 25, 2021 (KR) ........................ 10-2021-0164723

(51) Int. Cl.

| | |
|---|---|
| ***C07K 16/24*** | (2006.01) |
| ***A61K 31/337*** | (2006.01) |
| ***A61K 39/395*** | (2006.01) |
| ***A61K 47/68*** | (2017.01) |
| ***G01N 33/575*** | (2026.01) |

(52) U.S. Cl.

CPC ............ *C07K 16/24* (2013.01); *A61K 31/337* (2013.01); *A61K 39/3955* (2013.01); *A61K 47/6803* (2017.08); *A61K 47/6845* (2017.08); *G01N 33/5758* (2026.01); *C07K 2317/24* (2013.01);

(Continued)

(58) Field of Classification Search

IPC ........................................................ C07K 16/24

See application file for complete search history.

(56) References Cited

U.S. PATENT DOCUMENTS

| | | | |
|---|---|---|---|
| 2002/0150576 A1 | 10/2002 | Larosa et al. |
| 2003/0165995 A1 | 9/2003 | Briskin et al. |

FOREIGN PATENT DOCUMENTS

| | | |
|---|---|---|
| WO | 2012/082470 A2 | 6/2012 |
| WO | 2020/223573 A2 | 11/2020 |
| WO | 2022/187660 A1 | 9/2022 |

OTHER PUBLICATIONS

Gutwein et al., Journal of Cellular and Molecular Medicine, 13: 3809-3825, Abstract, downloaded Jun. 7, 2026 from CXCL16 and oxLDL are induced in the onset of diabetic nephropathy—Gutwein—2009—Journal of Cellular and Molecular Medicine—Wiley Online Library (Year: 2010).*

(Continued)

*Primary Examiner* — Karl J Puttlitz

(74) *Attorney, Agent, or Firm* — Bridgeway IP Law Group, PLLC; Jihun Kim

(57) ABSTRACT

This application discloses a CXCL16 antibody for cancer treatment. In some embodiments, a CXCL16 antibody disclosed herein can inhibit the growth of cancer, for example, thyroid cancer, breast cancer, and prostate cancer. Also described is a combination of a CXCL16 antibody with a targeted anticancer agent and/or an immune checkpoint inhibitor for cancer treatment.

30 Claims, 15 Drawing Sheets

Specification includes a Sequence Listing.

(52) U.S. Cl.
CPC .... *C07K 2317/31* (2013.01); *G01N 2333/521* (2013.01)

(56) References Cited

OTHER PUBLICATIONS

PCT/IB2022/061294, "International Search Report and Written Opinion", Apr. 14, 2023, 17 pages.

Luyten, Kattie, "European Search Report for EP Application No. 22898047.0", Jun. 6, 2025, EPO, Germany.

Examiner, "Request for the Submission of an Opinion for KR Application No. 10-2024-7002030", Mar. 16, 2026, KIPO, Republic of Korea.

Chung, Brile et al., "Human brain metastatic stroma attracts breast cancer cells via chemokines CXCL16 and CXCL12", npj Breast Cancer, Mar. 22, 2017, vol. 3, Article 6, Nature Publishing Group, London, United Kingdom.

Ikeda, Taro et al., "Mesenchymal stem cell-derived CXCL16 promotes progression of gastric cancer cells by STAT3-mediated expression of Ror1", Cancer Science, Apr. 2020, vol. 111, No. 4, 1254-1265 pages, John Wiley & Sons Australia, Ltd., Australia.

* cited by examiner

HUMAN CXCLI6 ANTIBODIES AND THE USE THEREOF

CROSS-REFERENCE TO RELATED APPLICATION

This application claims priority to Korean Patent Application No. 10-2021-0164723, filed on with the Korean Intellectual Property Office on Nov. 25, 2021. The entire content of said application is herein incorporated by reference for all purposes.

FIELD

The present invention relates to therapeutic antibodies used to treat cancer.

BACKGROUND

Cancer is currently one of the diseases that cause the highest number of deaths worldwide, and the cancer incidence rate is expected to increase further as the age of cancer onset is gradually decreasing while the average lifespan is gradually increasing. Cancer develops when abnormal cell division occurs due to genetic and environmental factors.

Unlike well-differentiated papillary thyroid carcinoma or follicular thyroid carcinoma, anaplastic thyroid carcinoma is a fatal disease due to rapid growth and high local recurrence, and the 5-year survival rate is 1.0% to 7.1%. It is known that the average survival period is 4 to 12 months. Any treatment has not shown satisfactory results. Various treatments have been tried, but they do not show satisfactory results in the clinical outcome and prognosis results so far. It occurs very rarely, and it is known that the proportion of all thyroid cancers is usually 5% to 10% or less. Because the growth of anaplastic thyroid carcinoma occurs rapidly in a short period of time, at the time of diagnosis, the tumor is not only large but also has severe local infiltration and distant metastases, making surgical treatment impossible in many cases. Therefore, for the treatment of thyroid anaplastic carcinoma, a multimodal approach is needed rather than a single therapy.

Triple-negative negative breast cancer (TNBC) does not have receptors that are commonly found in breast cancer. It does not express estrogen receptors or progesterone receptors, and it is HER2-negative (ER−/PR−/HER2−). TNBC is resistant to a number of conventional breast cancer therapies, such as taxol, tamoxifen, and anti-HER2 receptor antibody (trastuzumab). Triple-negative breast cancer occurs in a younger age group, is more common in premenopausal age, has a high local and distant recurrence rat, is more likely to metastasize to hematogenous than to lymph node metastasis, has a higher nuclear and tissue grade than other types, and has a large tumor size. All these characteristics are associated with a poor prognosis. However, triple-negative breast cancer still has no effective molecular target therapy or anticancer agent compared to other breast cancers, so it is necessary to investigate various tumor biology.

Based on recent research, it is reported that anticancer drugs having a specific target are more likely to develop resistance (acquired resistance) than anticancer drugs without a target. To prevent acquired resistance to anticancer drugs and maximize the efficacy of an anticancer drug, combination therapy with drugs that inhibit the factors that induce acquired resistance is emerging. In addition, the scope of application of the targeted anticancer agent is often limited, and it is also possible to expand the scope of application by co-administration with inhibitors of other factors. In addition, by such combined administration, it is possible to reduce the amount of the anticancer agent administered by enhancing the efficacy of the anticancer agent even when the efficacy is shown as well as the case where resistance to the anticancer agent is shown. Through this, it is possible to increase the anticancer efficacy while minimizing the toxicity and/or side effects of the anticancer agent on each organ of the body.

BRIEF SUMMARY

This application discloses a CXCL16 antibody for cancer treatment. In some embodiments, a CXCL16 antibody disclosed herein can inhibit the growth of cancer, for example, thyroid cancer, breast cancer, and prostate cancer. Also described is a combination of a CXCL16 antibody with a targeted anticancer agent and/or an immune checkpoint inhibitor for cancer treatment.

In one aspect, provided herein is an antibody that binds to CXCL16 comprising a heavy chain variable region comprising: an HCDR1 of any one of SEQ ID NO: 12 or a variant thereof in which 1, 2, 3, 4, or 5 amino acids are substituted relative to the sequence; an HCDR2 of any one of SEQ ID NO: 13 or a variant thereof in which 1, 2, 3, 4, or 5 amino acid is substituted relative to the sequence; and an HCDR3 in of any one of SEQ ID NO: 14 or a variant thereof in which 1, 2, 3, 4, or 5 amino acids are substituted relative to the sequence; a light chain variable region comprising: an LCDR1 of any one of SEQ ID NO: 15 or a variant thereof in which 1, 2, 3, 4, or 5 amino acid is substituted relative to the sequence; an LCDR2 of any one of SEQ ID NO: 16 or a variant thereof in which 1, 2, or 3 amino acid is substituted relative to the sequence; and an LCDR3 of any one of SEQ ID NO: 17 or a variant thereof in which 1, 2, 3, 4, or 5 amino acid is substituted relative to the sequence.

In some embodiments, the antibody comprises one or more of the following: an HC-FR1 that is at least 80% identical to SEQ ID NO: 22; an HC-FR2 that is at least 80% identical to SEQ ID NO: 23; an HC-FR3 that is at least 80% identical to SEQ ID NO: 24; an HC-FR4 that is at least 80% identical to SEQ ID NO: 25; an LC-FR1 that is at least 80% identical to SEQ ID NO: 26; an LC-FR2 that is at least 80% identical to SEQ ID NO: 27; an LC-FR3 that is at least 80% identical to SEQ ID NO: 28; and an LC-FR4 that is at least 80% identical to SEQ ID NO: 29

In some embodiments, the antibody comprises: an HC-FR1 having an amino acid sequence of SEQ ID NO: 22; an HC-FR2 having an amino acid sequence of SEQ ID NO: 23; an HC-FR3 having an amino acid sequence of SEQ ID NO: 24; an HC-FR4 having an amino acid sequence of SEQ ID NO: 25; an LC-FR1 having an amino acid sequence of SEQ ID NO: 26; an LC-FR2 having an amino acid sequence of SEQ ID NO: 27; an LC-FR3 that is at least 80% identical to SEQ ID NO: 28; and an LC-FR4 that is at least 80% identical to SEQ ID NO: 29.

In some embodiments, the antibody comprises one or more of the following: an HC-FR1 having an amino acid sequence of SEQ ID NO: 22; an HC-FR2 having an amino acid sequence of SEQ ID NO: 23; an HC-FR3 having an amino acid sequence of SEQ ID NO: 24; an HC-FR4 having an amino acid sequence of SEQ ID NO: 25; an LC-FR1 having an amino acid sequence of SEQ ID NO: 26; an LC-FR2 having an amino acid sequence of SEQ ID NO: 27; an LC-FR3 that is at least 80% identical to SEQ ID NO: 28; and an LC-FR4 that is at least 80% identical to SEQ ID NO:

29. In some embodiments, the antibody competes with CXCR6 (SEQ ID NO: 21) for binding to CXCL16.

In some embodiments, the antibody comprises: a heavy chain variable region comprising: an HCDR1 of any one of SEQ ID NO: 12 or a variant thereof in which 1, 2, 3, 4, or 5 amino acids are substituted relative to the sequence; an HCDR2 of any one of SEQ ID NO: 13 or a variant thereof in which 1, 2, 3, 4, or 5 amino acid is substituted relative to the sequence; and an HCDR3 in of any one of SEQ ID NO: 14 or a variant thereof in which 1, 2, 3, 4, or 5 amino acids are substituted relative to the sequence; a light chain variable region comprising: an LCDR1 of any one of SEQ ID NO: 15 or a variant thereof in which 1, 2, 3, 4, or 5 amino acid is substituted relative to the sequence; an LCDR2 of any one of SEQ ID NO: 16 or a variant thereof in which 1, 2, or 3 amino acid is substituted relative to the sequence; and an LCDR3 of any one of SEQ ID NO: 17 or a variant thereof in which 1, 2, 3, 4, or 5 amino acid is substituted relative to the sequence.

In some embodiments, the antibody comprises all six CDRs of SEQ ID NOs 12-17.

In some embodiments, the antibody comprises a VH region comprising a VH amino acid sequence of any one of SEQ ID NOs: 1-5 or an amino sequence having at least 70%, at least 75%, at least 80%, at least 85%, at least 90%, or at least 95% identity to the VH amino acid sequence, and/or wherein the antibody comprises a VL region comprising a VL amino acid sequence of any one of SEQ ID NOs: 6-10; and an amino sequence having at least 70%, at least 75%, at least 80%, at least 85%, at least 90%, or at least 95% identity to the VL amino acid sequence.

In some embodiments, the antibody comprises the VH of an antibody selected from the group consisting of HC4LC1, HC5LC1, HC5LC2, HC5LC3, and HC5LC5, or a variant thereof.

In some embodiments, the antibody comprises the VL of an antibody selected from the group consisting of HC4LC1, HC5LC1, HC5LC2, HC5LC3, and HC5LC5. In some embodiments, the antibody comprises both the VH and VL of an antibody selected from the group consisting of HC4LC1. HC5LC1. HC5LC2, HC5LC3, and HC5LC5.

In some embodiments, the antibody comprises a heavy chain of SEQ ID NO: 42 and a light chain of SEQ ID NO: 43.

In some embodiments, at least 1 or 2 of the substitutions are conservative substitutions; at least 50% of the substitutions are conservative substitutions; or all of the substitutions are conservative substitutions.

In another aspect, provided herein is an isolated antibody or an antibody fragment disclosed herein.

In some embodiments, the antibody is a humanized antibody, a chimeric antibody, a multispecific antibody, a bispecific antibody, an scFv, or an Fab. In some embodiments, the CXCL16 antibody is a humanized antibody and comprises a human IgG1 isotype constant domain SEQ ID NO: 48. In some embodiments, the humanized CXCL16 antibody comprises SEQ ID NO: 49.

In some embodiments, the antibody competes for binding with an CXCL16 antibody disclosed herein.

In some embodiments, the antibody comprises a VH region comprising a VH amino acid sequence of any one of SEQ ID NO: 1-5, and/or a VL region comprising a VL amino acid sequence of any one of SEQ ID NO: 6-10, or an antibody comprising a VH region with at least 70% identity to the VH amino acid sequence and a VL region having at least 70% identity to VL amino acid sequence, with variations to the corresponding VH or VL regions present only in Framework regions.

In some embodiments, the FW regions in the VL region of the antibody are at least 80% identical to the FW regions present in the VL region of any one of the corresponding antibody.

In another aspect, provided herein is an immunoconjugate comprising the antibody and a cytotoxic agent.

In another aspect, provided herein is a polypeptide comprising (1) a VH sequence having at least 70% amino acid sequence identity to a VH amino acid sequence any one of SEQ ID NO: 1-5 and/or a VL sequence having at least 70% amino acid sequence identity to a VL amino acid sequence of any one of SEQ ID NO: 6-10.

In another aspect, provided herein is a polynucleotide encoding the polypeptide disclosed above.

In another aspect, provided herein is an expression vector comprising a polynucleotide encoding the VH region and/or the VL region of the antibody disclosed above.

In another aspect, provided herein is a host cell that comprises an expression vector of example(s) 20. In some embodiments, the host cell comprises a polynucleotide that encodes the VH region and/or the VL region of the antibody disclosed above.

In another aspect, provided herein is a pharmaceutical composition comprising (i) an antibody disclosed above or an immunoconjugate of the antibody and (ii) a pharmaceutically acceptable carrier.

In another aspect, provided herein is a method of inducing an immune response and/or treating cancer, the method comprising administering the antibody or the pharmaceutical composition disclosed above.

In another aspect, provided herein is a method for inhibiting tumor metastasis, the method comprising administering an antibody or the pharmaceutical composition disclosed above. In some embodiments, the method for inhibiting tumor metastasis, wherein the tumor metastasis is bone metastasis. In some embodiments, the antibody is administered intravenously.

In another aspect, provided herein is a method of treating a cancer patient having tumor tissue that can be bound by an antibody that binds a CXCL16, the method comprising administering the antibody disclosed above to the patient. In some embodiments, the cancer is thyroid cancer or breast cancer. In some embodiments, the breast cancer is triple-negative breast cancer. In some embodiments, the antibody is administered intravenously.

In some embodiments, the method further comprises administering chemotherapy and/or radiation therapy. In some embodiments, the chemotherapy is paclitaxel. In some embodiments, the method further comprises administering an agent that targets an immunological checkpoint antigen.

In some embodiments, the agent is a monoclonal antibody. In some embodiments, the monoclonal antibody blocks PD-1 ligand binding to PD-1. In some embodiments, the monoclonal antibody is an anti-PD-1 antibody.

In yet another aspect, provided herein is a method of identifying a patient having a tumor suitable for treatment with an antibody that binds CXCL16, wherein the method comprises contacting a tumor sample from the patient with an antibody disclosed above, and detecting binding of the antibody to the tumor sample, wherein detection of the binding indicates the patient having a tumor suitable for treatment with the antibody that binds CXCL16.

In yet another aspect, provided herein is a method of producing an antibody, the method comprising culturing a host cell disclosed above under conditions in which the polynucleotide encoding the heavy chain and the polynucleotide encoding the light chain are expressed.

In yet another aspect, provided herein is a method of identifying an antibody having tumor-targeting activity, the method comprising mutagenizing a polynucleotide encoding a VH or a VL CDR3 of an antibody disclosed above; expressing an antibody comprising the mutagenized VH or VL CDR3; and selecting an antibody that inhibits tumor growth or decreases tumor size, tumor invasion, and/or metastasis in vivo.

In yet another aspect, provided herein is use of an antibody disclosed above for a method of treating cancer. In some embodiments, the cancer is associated with increased CXCL16 expression. In some embodiments, the cancer is breast cancer, thyroid cancer, cervical cancer, lung cancer, pancreatic cancer, non-small cell lung cancer, liver cancer, colon cancer, colorectal cancer, bone cancer, skin cancer, head cancer, cervical cancer, skin melanoma, intraocular melanoma, uterine cancer, ovarian cancer, rectal cancer, liver cancer, brain tumor, bladder cancer, blood cancer, stomach cancer, perianal cancer, breast cancer, fallopian tube carcinoma, endometrial carcinoma, vaginal cancer, vulvar carcinoma. Hodgkin's disease, esophageal cancer, small intestine cancer, endocrine adenocarcinoma, thyroid cancer, parathyroid cancer, adrenal cancer. Soft tissue sarcoma, urethral cancer, penile cancer, prostate cancer, bladder cancer, kidney cancer, ureter cancer, renal cell carcinoma, renal pelvic carcinoma, CNS central nervous system tumor, primary CNS lymphoma, spinal cord tumor, or brain stem glioma.

BRIEF DESCRIPTION OF DRAWINGS

FIG. 9A shows bioluminescence image (BLI) of bone tumor in tibia at 5 and 7 weeks. FIG. 9B is a schematic illustrating the development of ZA-R model of bone metastasis. FIG. 9C shows data indicating the CXCL16 concentration in bone marrow serum.

FIG. 10A illustrates the experimental design. FIG. 10B shows representative BLIs indicating the extent of bone metastasis. FIG. 10C contains dot plots representing the bioluminescence (BLI) results.

FIG. 11A shows the experimental design. FIG. 11B shows representative BLIs indicating the extent of bone metastasis. FIG. 11C contains dot plots representing the bioluminescence (BLI) results.

DETAILED DESCRIPTION

Figure 1A:
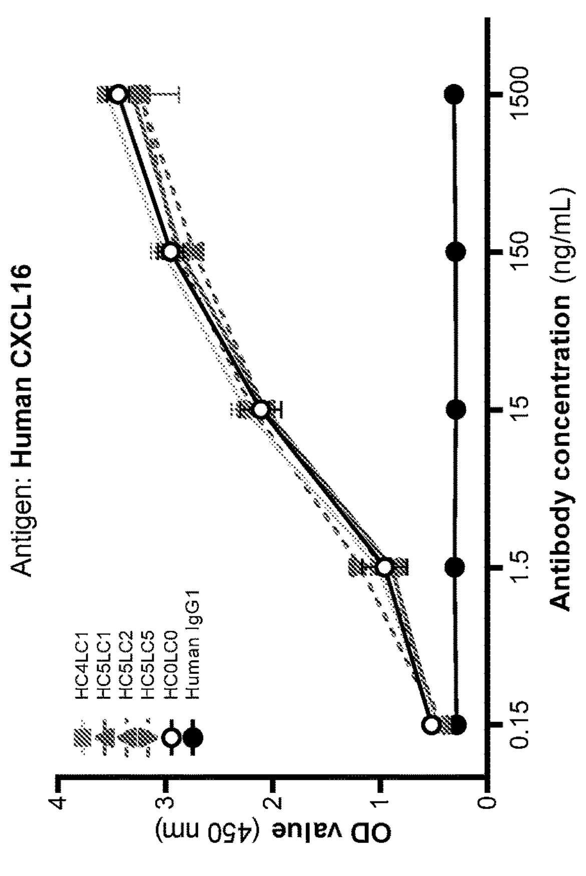
FIGS. 1A and 1B show the results of binding of humanized CXCL16 antibodies (HC4LC1, HC5LC1, HC5LC2, and HC5LC5) to human CXCL16 (FIG. 1A) versus mouse CXCL16 (FIG. 1B).

The present disclosure provides a pharmaceutical composition for preventing or treating cancer comprising a CXCL16 antibody. In some embodiments, the pharmaceutical further comprises one or more of a targeted anticancer agent and an immune checkpoint inhibitor. The CXCL16 antibody may be provided in the form of a full-length antibody or a fragment thereof.

TERMINOLOGY

As used herein, the singular forms "a," "an." and "the," include plural referents unless the content dictates otherwise. Thus, for example, reference to "an antibody" optionally includes a combination of two or more such molecules and the like.

The term "about," as used herein, refers to the usual error range for the respective value readily known to the skilled person in this technical field; for example, ±20%, ±10%, or ≡5%, are within the intended meaning of the recited value.

As used herein, the term "antibody" means an isolated or recombinant binding agent that comprises the necessary variable region sequences to specifically bind an antigenic epitope. Therefore, an "antibody" as used herein is any form of an antibody of any class or subclass or fragment thereof that exhibits the desired biological activity, e.g., binding a specific target antigen. Thus, it is used in the broadest sense and specifically covers a monoclonal antibody (including a full-length monoclonal antibody), a human antibody, a chimeric antibody, a nanobody, a diabody, a multispecific antibody (e.g., a bispecific antibody), and an antibody fragment including but not limited to scFv, Fab, and the like so long as it exhibits the desired biological activity. In this application, the terms "anti-CXCL16 antibody" and "CXCL16 antibody" are used interchangeably.

"Antibody fragments" comprise a portion of an intact antibody, for example, the antigen-binding or variable region of the intact antibody. Examples of antibody fragments include Fvs, Fab, Fab', $F(ab')_2$, and Fv fragments; diabodies; linear antibodies (e.g., Zapata et al., Protein Eng. 8 (10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab)_2$ fragment with two antigen combining sites and is still capable of cross-linking antigen. In the context of the present invention, the binding domains comprise an Fv, comprising a variable light chain (VL) and a variable heavy chain (VH). These are generally formatted as either an scFv domain, comprising either (N to C-terminal) VL-scFv linker-VH or VH-scFv linker-VL on a single polypeptide chain, or as Fab fragments on two different polypeptide chains, VH-CH1 coupled with VL-CL.

A single-chain Fv or scFv refers to an antibody fragment comprising the VH and VL domains of an antibody, wherein these domains are present in a single polypeptide chain. Generally, the Fv polypeptide further comprises a polypeptide linker between the VH and VL domains, which allows the scFv to form the desired structure for antigen binding. For an overview of scFv, see Pluckthun (1994) THE PHARMACOLOGY OF MONOCLONAL ANTIBODIES, vol. 113, Rosenburg and Moore eds. Springer-Verlag, New York, pp. 269-315]. See also WO 88/01649 and U.S. Pat. Nos. 4,946,778 and 5,260,203.

As used herein, "V-region" or "variable region" or "variable domain" refers to an antibody variable region domain comprising the segments of Framework 1, CDR1. Framework 2, CDR2. Framework 3, CDR3, and Framework 4. The heavy chain V-region, VH, is a consequence of rearrangement of a V-gene (HV), a D-gene (HD), and a J-gene (HJ), in what is known as V(D)J recombination during B-cell differentiation. The light chain V-region, VL, is a consequence of rearrangement of a V-gene (LV) and a J-gene (LJ), of an antibody refers to the amino-terminal domain of the heavy or light chain of an antibody. The variable region of a heavy chain is described as "VH" or "$V_H$" and the variable region of a light chain is described as "VL" or "$V_L$". These domains are generally the most variable portions of an antibody and contain the antigen-binding site.

As used herein, "complementarity-determining region (CDR)" refers to the three hypervariable regions (HVRs) in each chain that interrupt the four "framework" regions established by the light and heavy chain variable regions. The CDRs are the primary contributors to binding to an epitope of an antigen. The CDRs of each chain are referred to as CDR1, CDR2, and CDR3, numbered sequentially starting from the N-terminus, and are also identified by the chain in which the CDR is located. Thus, a VH CDR3 (HCDR3) is in the variable domain of the heavy chain of the antibody in which it is found, whereas a VL CDR3 (LCDR3) is the CDR3 from the variable domain of the light chain of the antibody in which it is located. The term "CDR" is used interchangeably with "HVR" when referring to CDR sequences.

The amino acid sequences of the CDRs and framework regions can be determined using various well-known definitions in the art, e.g., Kabat, Chothia, international ImMunoGene Tics database (IMGT), and AbM (see, e.g., Chothia & Lesk, 1987, Canonical structures for the hypervariable regions of immunoglobulins. J. Mol. Biol. 196, 901-917; Chothia C. et al., 1989. Conformations of immunoglobulin hypervariable regions. Nature 342, 877-883; Chothia C. et al., 1992, Structural repertoire of the human VH segments. J. Mol. Biol. 227, 799-817; Al-Lazikani et al., J. Mol. Biol. 1997, 273 (4)). Definitions of antigen combining sites are also described in the following: Ruiz et al., IMGT, The international ImMunoGeneTics database. Nucleic Acids Res., 28, 219-221 (2000); and Lefranc, M.-P. IMGT, the international ImMunoGeneTics database. Nucleic Acids Res. January 1; 29 (1): 207-9 (2001); MacCallum et al. Antibody-antigen interactions; Contact analysis and binding site topography, J. Mol. Biol . . . 262 (5), 732-745 (1996); and Martin et al., Proc. Natl Acad. Sci. USA. 86, 9268-9272 (1989); Martin, et al., Methods Enzymol., 203, 121-153, (1991); Pedersen et al., Immunomethods, 1, 126, (1992); and Rees et al., In Sternberg M. J. E. (ed.), Protein Structure Prediction. Oxford University Press, Oxford, 141-172 1996). Reference to CDRs as determined by Kabat numbering are based, for example, on Kabat et al., Sequences of Proteins of Immunological Interest, 5th Ed. Public Health Service, National Institute of Health, Bethesda, MD (1991)). Chothia CDRs are determined as defined by Chothia (see, e.g., Chothia and Lesk J. Mol. Biol. 196:901-917 (1987)). Numbering and placement of the CDRs can differ depending on the numbering system employed. It is understood that disclosure of a variable heavy and/or variable light sequence includes the disclosure of the associated CDRs, regardless of the numbering system employed. Unless explicitly stated otherwise, the CDRs in this application, for example, those shown in Table 3, are defined by combining IMGT and Kabat. As one illustrative example, the CDR1 region of SEQ ID NO: 1 is GFTFSNAVMN, which is a combination of residues of GFTFSNAV (according to IMGT) and NAVMN (according to Kabat).

An "Fc region" refers to the constant region of an antibody excluding the first constant region immunoglobulin domain. For human immunoglobulins, "Fc" refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 and Cγ3 and the hinge between Cγ1 and Cγ2. It is understood in the art that the boundaries of the Fc region may vary; however, the human IgG heavy chain Fc region is usually defined to comprise residues C226 or P230 to its carboxyl-terminus, using the numbering according to the EU index as in Kabat et al., (1991, NIH Publication 91-3242, National Technical Information Service, Springfield, VA). The term "Fc region" may refer to this region in isolation or this region in the context of an antibody or antibody fragment. "Fc region" includes naturally occurring allelic variants of the Fc region as well as modifications that modulate effector function. Fc regions also include variants that do not result in alterations to biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., *Science* 247:306-1310, 1990). For example, for IgG4 antibodies, a single amino acid substitution (S228P according to Kabat numbering; designated IgG4Pro) may be introduced to abolish the heterogeneity observed in recombinant IgG4 antibody (see, e.g., Angal, et al., *Mol Immunol* 30:105-108, 1993). In certain embodiments, the Fc region includes substitutions that improve pharmacokinetics properties of an antibody, e.g., increased serum half-life. Non-limiting examples of substitutions of the Fc region can be found in U.S. Pat. No. 8,088,376, the content of which is incorporated by reference in its entirety.

The term "heavy chain" as used herein refers to a full-length heavy chain comprising a variable region domain VH comprising an amino acid sequence having sufficient variable region sequence to confer specificity to an antigen, and three constant domain domains CH1, CH2 and CH3, and fragments thereof means all In addition, as used herein, the term "light chain" refers to both a full-length light chain including a variable region domain VL and a constant region CL comprising an amino acid sequence having a sufficient variable region sequence to confer specificity to an antigen and a fragment thereof.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, e.g., the length of the two sequences, when compared and aligned for maximum correspondence over a comparison window or designated region. Alignment for determining percent amino acid sequence identity can be performed in various methods, including those using publicly available computer software such as BLAST, BLAST-2, ALIGN, or Megalign (DNASTAR) software. Examples of algorithms suitable for determining percent sequence identity and sequence similarity are the BLAST 2.0 algorithms, described in Altschul et al., Nuc. Acids Res. 25:3389-3402 (1977) and Altschul et al., J. Mol. Biol. 215:403-410 (1990). Thus, for purposes of this invention, BLAST 2.0 can be used with the default parameters to determine the percent sequence identity.

Antibodies or fragments thereof of the present invention can be generated using methods known in the art, for example, phage display methods or yeast cell surface expression systems. For example, the methods described in U.S. Pat. Nos. 4,946,778 and 5,258,498 may be used to prepare an scFv, and the methods described in WO 92/22324 can be used to produce recombinant Fab, Fab', and F(ab')2 fragments.

The antibody of the present invention may be derived from any animal, including mammals, birds, and the like including humans. Preferably, the antibody may be a human, mouse, donkey, sheep, rabbit, goat, guinea pig, camel, horse, or chicken antibody.

A human antibody is an antibody having the amino acid sequence of a human immunoglobulin and includes either an antibody isolated from a human immunoglobulin library or an antibody isolated from an animal transfected for one or more human immunoglobulins which does not express endogenous immunoglobulins (USA). see U.S. Pat. No. 5,939,598).

The antibody or antigen-binding fragment thereof of the present invention includes all mutants that achieve the desired effect of the present invention through mutation, such as one or more substitutions, deletions, inversions or translocations, in the antibody defined by the above sequence.

The terms "nucleic acid" and "polynucleotide" are used interchangeably and as used herein, refer to both sense and anti-sense strands of RNA, cDNA, genomic DNA, and synthetic forms and mixed polymers of the above. In particular embodiments, a nucleotide refers to a ribonucleotide, deoxynucleotide, or a modified form of either type of nucleotide and combinations thereof. The terms also include, but are not limited to, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, the substitution of one or more of the naturally occurring nucleotides with an analog, internucleotide modifications such as uncharged linkages (e.g., methyl phosphonates, phosphotriesters, phosphoramidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). The above term is also intended to include any topological conformation, including single-stranded, double-stranded, partially duplexed, triplex, hair pinned, circular, and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids that encode the same polypeptide sequence.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. A "vector" as used here, refers to a recombinant construct in which a nucleic acid sequence of interest is inserted into the vector. Specific vectors can direct the expression of nucleic acids to which they are operatively linked. Such vectors are referred to herein as "expression vectors."

A "substitution." as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody or fragment thereof" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell." "host cell line." and "host cell culture" are used interchangeably and refer to cells into which exogenous nucleic acid has been introduced, including the progeny of such cells. Thus, a host cell is a recombinant host cells and includes the primary transformed cell and progeny derived therefrom without regard to the number of passages.

A polypeptide "variant," as the term is used herein, is a polypeptide that typically differs from a polypeptide specifically disclosed herein in one or more substitutions, deletions, additions and/or insertions. As used herein, a "variant" refers to an engineered sequence, rather than a naturally occurring sequence.

The term "comparable," in the context of describing the strength of binding of two antibodies to the same target, refers to two dissociation constant ($K_D$) values calculated from two binding reactions that are within three (3) fold from each other. In other words, the ratio between the first $K_D$ (the $K_D$ of the binding reaction between the first antibody and the target) and the second $K_D$ (the $K_D$ of the binding reaction between the second antibody and the target) is within the range of 1:3 or 3:1, endpoints exclusive. A lower $K_D$ value denotes stronger binding. For example, an antibody variant that has stronger binding as compared to a reference antibody binds to the target with a $K_D$ that is at least ⅓ of the $K_D$ measured against the same target for the reference antibody.

As used herein, "therapeutic agent" refers to an agent that, when administered to a patient suffering from a disease in a therapeutically effective dose, will cure, or at least partially arrest, the symptoms of the disease and complications associated with the disease.

As used herein, the term "individual" refers to a subject in need of treatment for a disease, for example, human or non-human primates, mice, rats, dogs, cats, horses, cattle, and the like. In some embodiments, the individual is a mammal.

As used herein, the term "administration" refers to providing a predetermined composition of the present invention to a subject by any suitable method.

As used herein, the term "prevention" refers to any action that suppresses or delays the onset of a target disease, As used herein, the term "treatment" means that the target disease and its metabolic abnormalities are improved.

As used herein, the term "improvement" means any action that reduces a parameter related to the desired disease, for example, the degree of a symptom by administration of the composition disclosed herein.

As used herein, the term "bone metastasis" refers to the spread of cancer cells from their original site to a bone. Nearly all types of cancer can spread (metastasize) to the bones, for example, breast cancer cells, thyroid cancer cells, prostate cancer cells, and the like.

CXCL16

CXCL16 (NM_022059) is a gene encoding a chemokine (C-X-C motif) ligand 16 (CXCL16). The CXCL16 protein is a small cytokine belonging to the CXC chemokine family. It consists of a CXC chemokine domain, a musin-like stalk, a transmembrane domain, and a cytoplasmic tail containing a potential tyrosine phosphorylation region capable of binding to SH2. Expression of CXCL16 is induced by the inflammatory cytokines IFN-gamma and TNF-alpha. CXCL16 is reported as a marker for predicting the prognosis of thyroid cancer. See Korean Patent No. 10-2019-0145732.

The human CXCL16 protein (SEQ ID NO: 11) comprises 254 amino acids, and it can bind to the chemokine receptor CXCR6. Kim et al., Scientific Reports, 9:13288| https://doi.org/10.1038/s41598-019-49613-z. Unlike other chemokines, CXCL16 is expressed as not only a membrane-bound molecule but also a soluble chemokine. Abel et al., J. Immunol. 172, 6362-6372 (2004). CXCL16 is produced by macrophages and dendritic cells and regulates immune cell chemotaxis into CXCL16-enriched environments. Jin et al., Oncol. Rep. 37, 3279-3286 (2017).

```
Huma CXCL 16:
                                              (SEQ ID NO: 11)
MGRDLRPGSRVLLLLLLLLLVYLTQPGNGNEGSVTGSCYCGKRISSDSPP

SVQFMNRLRKHLRAYHRCLYYTRFQLLSWSVCGGNKDPWVQELMSCLDLK

ECGHAYSGIVAHQKHLLPTSPPISQASEGASSDIHTPAQMLLSTLQSTQR

PTLPVGSLSSDKELTRPNETTIHTAGHSLAAGPEAGENQKQPEKNAGPTA

RTSATVPVLCLLAHIFILTAALSYVLCKRRRGQSPQSSPDLPVHYIPVAP

DSNT
```

CXCL16 Antibody

In some embodiments, a CXCL16 antibody disclosed herein binds to CXCL16 (SEQ ID NO: 11) and comprises a heavy chain variable region comprising: an HCDR1 comprising SEQ ID NO: 12, or a variant HCDR1 in which 1, 2, 3, 4, or 5 amino acids are substituted relative to the sequence; an HCDR2 comprising SEQ ID NO: 13, or a variant HCDR2 in which 1, 2, 3, 4, or 5 amino acid is substituted relative to the sequence; and an HCDR3 comprising SEQ ID NO: 14, or a variant HCDR3 in which 1, 2, 3, 4, or 5 amino acids are substituted relative to the sequence. In some embodiments, the antibody comprises a light chain variable region comprising: an LCDR1 comprising any one of SEQ ID NO: 15 or a variant LCDR1 in which 1, 2, 3, 4, or 5 amino acid is substituted relative to the sequence; an LCDR2 comprising any one of SEQ ID NO: 16, or variant LCDR2 in which 1, 2, or 3 amino acid is substituted relative to the sequence; and an LCDR3 comprising any one of SEQ ID NO: 17, or a variant LCDR3 in which 1, 2, 3, 4, or 5 amino acid is substituted relative to the sequence.

In some embodiments, an antibody that binds to CXCL16 comprises a VH comprising an amino acid sequence having at least 95% identity to any one of SEQ ID NO: 1-5; and a VL comprising an amino sequence having at 95% identity to any one of SEQ ID NO: 6-10.

In some embodiments, the CXCL16 antibody has at least one mutation and no more than 10, 20, 30, 40, or 50 mutations in the VL amino acid sequences compared to a VL sequence set forth in Table 3. In some embodiments, the VL amino acid sequence may comprise 1, 2, 3, 4, 5, 6, 7, 8, 9, or 10 amino acid insertions or deletions compared to a VL sequence set forth in Table 3. In some embodiments, the VL amino acid sequence may comprise a deletion or insertion, e.g., a 1, 2, 3, 4, 5, 6, or 7 amino acid deletion or insertion, relative to a CDR sequence shown in Table 2. In some embodiments, a CXCL16 antibody of the present disclosure comprises an LCDR1, LCDR2, and LCDR3, each having at least 70% identity to a LCDR1, LCDR2, and LCDR3, as shown in Table 2. In some embodiments, a CXCL16 antibody of the present invention comprises a LCDR1, LCDR2, and LCDR3, each having at least 80% identity to a LCDR1, LCDR2, and LCDR3, as shown in Table 2. In some embodiments, a CXCL16 antibody of the present invention comprises one, two, or all three of LCDR1, LCDR2, and LCDR3, as set forth in SEQ ID NOs: 15-17, respectively.

In some embodiments, the CXCL16 antibody has at least one mutation and no more than 10, 20, 30, 40, or 50 mutations in the VH amino acid sequences compared to a VH sequence set forth in Table 3. In some embodiments, the VH amino acid sequence may comprise 1, 2, 3, 4, 5, 6, 7, 8, 9, or 10 amino acid insertions or deletions compared to a VH sequence set forth in Table 3. In some embodiments, the VH amino acid sequence may comprise a deletion or insertion, e.g., a 1, 2, 3, 4, 5, 6, or 7 amino acid deletion or insertion, relative to a CDR sequence shown in Table 1. In some embodiments, the VH region comprises an HCDR1 having 1 or 2 substitutions relative to an HCDR1 sequence shown in Table 1. In some embodiments, an HCDR1 has 3, 4, or 5 substitutions relative to an HCDR1 sequence shown in Table 1. In some embodiments, the VH region comprises a CDR2 with 1 or 2; or 1, 2, or 3; substitutions relative to the HCDR2 sequence are shown in Table 1. In some embodiments, the VH region comprises an HCDR3 with 1, 2, or 3; or 1, 2, 3, or 4; substitutions relative to an HCDR3 sequence shown in Table 1. In some embodiments, a CXCL16 antibody of the present disclosure comprises an HCDR1, HCDR2, and HCDR3, each having at least 70% identity to a CDR1, CDR2, and CDR3, as shown in Table 1. In some embodiments, a CXCL16 antibody of the present invention comprises an HCDR1, HCDR2, and HCDR3, each having at least 80% identity to an HCDR1, HCDR2, and HCDR3, as shown in Table 1. In some embodiments, an anti-tumor antibody of the present invention comprises one, two, or all three of HCDR1, HCDR2, and HCDR3, as set forth in SEQ ID NOs: 12-14, respectively.

In some embodiments, the FR1 region of a VH region of a CXCL16 antibody as described herein is at least 80% or at least 90% identical to SEQ ID NO: 22. In some embodiments, the FR1 region of a $V_H$ region of a CXCL16 antibody has a sequence of SEQ ID NO: 22

In some embodiments, the FR2 region of a VH region of a CXCL16 antibody as described herein is at least 80% or at least 90% identical to SEQ ID NO: 23. In some embodiments, the FR2 region of a $V_H$ region of a CXCL16 antibody has a sequence of SEQ ID NO: 23

In some embodiments, the FR3 region of a VH region of a CXCL16 antibody as described herein is at least 80% or at least 90% identical to SEQ ID NO: 24. In some embodiments, the FR3 region of a $V_H$ region of a CXCL16 antibody has a sequence of SEQ ID NO: 24

In some embodiments, the FR4 region of a VH region of a CXCL16 antibody as described herein is at least 80% or at least 90% identical to SEQ ID NO: 25. In some embodiments, the FR4 region of a $V_H$ region of a CXCL16 antibody has a sequence of SEQ ID NO: 25.

In some embodiments, the FR1 region of a VL region of a CXCL16 antibody as described herein is at least 80% or at least 90% identical to SEQ ID NO: 26. In some embodiments, the FR1 region of a $V_L$ region of a CXCL16 antibody has the sequence of SEQ ID NO: 26.

In some embodiments, the FR2 region of a $V_L$ region of a CXCL16 antibody as described herein is at least 80% or at least 90% identical to SEQ ID NO: 27. In some embodiments, the FR2 region of a $V_L$ region of a CXCL16 antibody has a sequence of SEQ ID NO: 27.

In some embodiments, the FR3 region of a $V_L$ region of a CXCL16 antibody as described herein is at least 80% or at least 90% identical to SEQ ID NO: 28. In some embodiments, the FR3 region of a $V_L$ region of a CXCL16 antibody has a sequence of SEQ ID NO: 28.

In some embodiments, the FR4 region of a $V_L$ region of a CXCL16 antibody as described herein is at least 80% or at least 90% identical to SEQ ID NO: 29. In some embodiments, the FR4 region of a $V_L$ region of a CXCL16 antibody has a sequence of SEQ ID NO: 29.

In some embodiments, the CXCL16 antibody is any one of HC4LC1, HC5LC1, HC5LC2, HC5LC3, and HC5LC5. In some embodiments, the CXCL16 antibody is HC5LC1.

TABLE 1

Heavy chain CDR sequences of exemplary CXCL16 antibodies

| HCDRI | HCDR2 | HCDR3 |
|---|---|---|
| GFTFSNAVMN (SEQ ID NO: 12) | RIRTKPNNYATFYADSVKG (SEQ ID NO: 13) | TAWTTEGIY (SEQ ID NO: 14) |

TABLE 2

Light chain CDR sequences of exemplary CXCL16 antibodies

| LCDR1 | LCDR2 | LCDR3 |
|---|---|---|
| KSSQSLLYSGNQKNYLA (SEQ ID NO: 15) | WASTRQS (SEQ ID NO: 16) | QQYYDTPWT (SEQ ID NO: 17) |

TABLE 3

Heavy and Light variable region sequences exemplary CXCL 16 antibodies

| Antibody | VH | VL |
|---|---|---|
| HC4LC1 | EVQLVESGGGLVKPGGSLRLSCAAS GFTFSNAVMNWVRQAPGKGLEWVA RIRTKPNNYATFYADSVKGRFTFSRD DSKNTLYLQMNSLKTEDTAVYYCT AWTTEGIYWGQGTTVTVSS (SEQ ID NO: 4) | DIVMTQSPDSLAVSAGFTVTINCKSS QSLLYSGNQKNYLAWYQQKPGQSP KLLIYWASTRQSGVPDRFSGSGSGTD FTLTISSVQAEDVAVYYCQQYYDTP WTFGGGTKVEIK (SEQ ID NO: 6) |
| HC5LC1 | EVQLVESGGGLVQPGGSLKLSCAAS GFTFSNAVMNWVRQASGKGLEWVA RIRTKPNNYATFYADSVKGRFTFSRD DSKNTAYLQMNSLKTEDTAMYYCT AWTTEGIYWGQGTLVTVSS (SEQ ID NO: 5) | DIVMTQSPDSLAVSAGFTVTINCKSS QSLLYSGNQKNYLAWYQQKPGQSP KLLIYWASTRQSGVPDRFSGSGSGTD FTLTISSVQAEDVAVYYCQQYYDTP WTFGGGTKVEIK (SEQ ID NO: 6) |

TABLE 3-continued

| Heavy and Light variable region sequences exemplary CXCL 16 antibodies | | |
|---|---|---|
| Antibody | VH | VL |
| HC5LC2 | EVQLVESGGGLVQPGGSLKLSCAAS<br>GFTFSNAVMNWVRQASGKGLEWVA<br>RIRTKPNNYATFYADSVKGRFTFSRD<br>DSKNTAYLQMNSLKTEDTAMYYCT<br>AWTTEGIYWGQGTLVTVSS<br>(SEQ ID NO: 5) | DIVMTQSPSSLAVSLGFTATINCKSS<br>QSLLYSGNQKNYLAWYQQKPGQPP<br>KLLIYWASTRQSGVPDRFTGSGAGT<br>DFTLTISSVQAEDLAIYYCQQYYDTP<br>WTFGGGTKVEIK<br>(SEQ ID NO: 7) |
| HC5LC3 | EVQLVESGGGLVQPGGSLKLSCAAS<br>GFTFSNAVMNWVRQASGKGLEWVA<br>RIRTKPNNYATFYADSVKGRFTFSRD<br>DSKNTAYLQMNSLKTEDTAMYYCT<br>AWTTEGIYWGQGTLVTVSS<br>(SEQ ID NO: 5) | DIQMTQSPSSLSASVGDRVTITCKSS<br>QSLLYSGNQKNYLAWYQQKPGQSP<br>KLLIYWASTRQSGVPDRFSGSGSGTD<br>FTLTISSLQAEDFATYYCQQYYDTPW<br>TFGGGTKVEIK<br>(SEQ ID NO: 8) |
| HC5LC5 | EVQLVESGGGLVQPGGSLKLSCAAS<br>GFTFSNAVMNWVRQASGKGLEWVA<br>RIRTKPNNYATFYADSVKGRFTFSRD<br>DSKNTAYLQMNSLKTEDTAMYYCT<br>AWTTEGIYWGQGTLVTVSS<br>(SEQ ID NO: 5) | DIVMTQSPSSLAVSAGERATINCKSS<br>QSLLYSGNQKNYLAWYQQKPGQSP<br>KLLIYWASTRQSGVPDRFIGSGSGTD<br>FTLTISSLQAEDVAIYYCQQYYDTPW<br>TFGGGTKLELK<br>(SEQ ID NO: 10) |

Note: the name of each CXCL16 antibody m this disclosure consists of two parts: the first part represents the heavy chain, and the second part represents the light chain. As an example, antibody HCSLC1 comprises a heavy chain HC5 (comprising SEQ ID NO: 42) and a light chain LC1 (comprising SEQ ID NO: 43), and so on. See Table 4.

TABLE 4

| The full-length sequences of exemplary heavy chain and light chain | | |
|---|---|---|
| Antibody | Heavy chain | Light Chain |
| HC4LC1 | SEQ ID NO: 41 | SEQ ID NO: 43 |
| HC5LC1 | SEQ ID NO: 42 | SEQ ID NO: 43 |

TABLE 4-continued

| The full-length sequences of exemplary heavy chain and light chain | | |
|---|---|---|
| Antibody | Heavy chain | Light Chain |
| HC5LC2 | SEQ ID NO: 42 | SEQ ID NO: 44 |
| HC5LC3 | SEQ ID NO: 42 | SEQ ID NO: 45 |
| HCSLCS | SEQ ID NO: 42 | SEQ ID NO: 47 |

TABLE 5

| Framework region sequences of exemplary CXCL16 antibodies | | |
|---|---|---|
| FR sequences | Sequence | Description |
| HC-FR1 | $X_1$VQLVESGGG$X_2$V$X_3$P$X_4X_5$SL$X_6X_7$SCAAS<br>(SEQ ID NO: 21) | $X_1$ can be A, Q, E.<br>$X_2$ can be L, V.<br>$X_3$ can be Q, K.<br>$X_4$ can be K, G.<br>$X_5$ can be E, G.<br>$X_6$ can be K, R.<br>$X_7$ can be I, L. |
| HC-FR2 | WVRQA$X_1$GKGLEWV$X_2$<br>(SEQ ID NO: 22) | $X_1$ can be P. S.<br>$X_2$ can be A, G. |
| HC-FR3 | FT$X_1$SRD$X_2$SK$X_3X_4X_5$YLQM$X_6X_7$L$X_8X_9$<br>EDTA$X_{10}$YYC<br>(SEQ ID NO: 23) | $X_1$ can be F, I.<br>$X_2$ can be D, N.<br>$X_3$ can be S, T, N.<br>$X_4$ can be M, T.<br>$X_5$ can be V, L, A.<br>$X_6$ can be D, N.<br>$X_7$ can be N, S, I.<br>$X_8$ can be K, R.<br>$X_9$ can be T, A.<br>$X_{10}$ can be M, V. |

TABLE 5-continued

Framework region sequences of exemplary CXCL16 antibodies

| FR sequences | Sequence | Description |
|---|---|---|
| HC-FR4 | WGQGTX$_1$VTVSS (SEQ ID NO: 24) | X$_1$ can be L, T |
| LC-FR1 | DIX$_1$MTQSPX$_2$SLX$_3$X$_4$SX$_5$GX$_6$X$_7$X$_8$TIX$_9$C (SEQ ID NO: 25) | X$_1$ can be V, Q.<br>X$_2$ can be S. D.<br>X$_3$ can be A, S.<br>X$_4$ can be V, A.<br>X$_5$ can be A, L, V.<br>X$_6$ can be E, D.<br>X$_7$ can be T, R.<br>X$_8$ can be V, A.<br>X$_9$ can be N, T. |
| LC-FR2 | WYQQKPGQX$_1$PKLLIY (SEQ ID NO: 26) | X$_1$ can be S, P. |
| LC-FR3 | GVPX$_1$RFX$_2$GSGX$_3$GTDFTLTISSX$_4$QX$_5$ EDX$_6$AX$_7$YYC (SEQ ID NO: 27) | X$_1$ can be D, S.<br>X$_2$ can be I, S, T.<br>X$_3$ can be S. A.<br>X$_4$ can be V, L.<br>X$_5$ can be A, P.<br>X$_6$ can be L, V, F.<br>X$_7$ can be I, V, T. |
| LC-FR4 | GGGTKX$_1$EX$_2$K (SEQ ID NO: 28) | X$_1$ can be L, V.<br>X$_2$ can be L, I. |

For the purpose of this disclosure, HC-FR1 refers to the Framework 1 (FR1) region of the heavy chain variable region; HC-FR2 refers to the FR2 region of the heavy chain variable region; HC-FR3 refers to the FR3 region of the heavy chain variable region; LC-FR1 refers to the Framework 1 (FR1) region of the light chain variable region; LC-FR2 refers to the FR2 region of the light chain variable region; LC-FR3 refers to the FR3 region of the light chain variable region.

Variants

In some embodiments, variants of any CXCL16 antibodies disclosed herein can be generated by introducing mutations to the heavy chain and/or light chain sequences. In some embodiments, the mutation(s) are introduced into one or more of the CDRs of a CXCL16 antibody disclosed herein, e.g., any one of the antibodies HC4LC1, HC5LC1, HC5LC2, HC5LC3, and HC5LC5. In some embodiments, the mutation(s) are introduced in the framework regions. In some embodiments, a CXCL16 antibody provided herein comprises a VH region of any one of SEQ ID NO: 1-5, and/or a VL region of any one of SEQ ID NO: 6-10, or an antibody comprising a VH region with at least 80% identity to any one of SEQ ID NO: 1-5 and a VL region having at least 80% identity to any one of SEQ ID NO: 6-10, with variations to the corresponding VH or VL regions present only in Framework regions.

The antibodies disclosed herein bind specifically to tumor cells. In some embodiments, the antibody is added to a cancer cell line, and the binding is analyzed using bio-light interferometry (ForteBio). HC4LC1, HC5LC1, HC5LC2. HC5LC3, and HC5LC5 all showed strong binding to human CXCL16. See Table 6 and Example 1.

In some embodiments, the CXCL16 antibody provided herein comprises an HCDR1 of SEQ ID NO: 12, an HCDR2 of SEQ ID NO: 13, an HCDR3 of SEQ ID NO: 14, an LCDR1 of SEQ ID NO: 15, an LCDR2 of SEQ ID NO: 16, an LCDR3 of SEQ ID NO: 17; and the FW regions in the VH region are at least 80% identical to the FW regions present in the VH region of any one of SEQ ID NO: 1-5, and wherein the FW regions in the VL region are at least 80% identical to the FW regions present in the VL region of any one of SEQ ID NO: 6-10.

Tumor-Binding Activity

The CXCL16 antibodies described herein can bind to tumor cells, as assessed by assays well known in the art. Nonlimiting examples of suitable assays include surface plasmon resonance analysis using a biosensor system such as a BIACORE® system or a flow cytometry assay, or a bio-light interferometry assay, which are further described in the EXAMPLES section.

In some embodiments, binding assays to assess variant activity are performed on tumor tissues or tumor cells ex vivo, e.g., on tumor cells that were grown as a tumor graft in a syngeneic (immune-matched) mouse in vivo and then harvested and processed within 24-48 hrs. Binding can be assessed by any number of means, including flow cytometry.

In some embodiments, the binding of the antibodies to bind to tumor cells is assessed by immunofluorescence methods performed on fresh frozen human tumor samples or fixed tumor samples using standard immunostaining procedures.

The antibodies disclosed herein bind specifically to tumor cells. In some embodiments, the antibody is added to a cancer cell line, and the binding is analyzed using a bio-light interferometry assay. HC4LC1, HC5LC1, HC5LC2, HC5LC3, and HC5LC5 showed a strong binding to human CXCL16. See, for example, Table 6 and Example 1.

Tumor Inhibition Activity

The in vivo tumor inhibition activity of the CXCL16 antibodies disclosed herein may be assessed by using several assays, including but not limited to monitoring tumor growth and animal survival. In some embodiments, the CXCL16 antibodies described herein exhibit inhibitory effects on tumors, including decreasing rate of tumor growth, size, tumor invasion and/or metastasis. In one illustrative example, the CXCL16 antibodies inhibit tumor growth in mice carrying tumor derived from MDA-MB-231 cells, see Example 2. Such antibodies exhibit tumor-targeting effects in vivo. e.g., when administered to subjects that have a tumor expressing or overexpressing CXCL16.

Figure 8B:
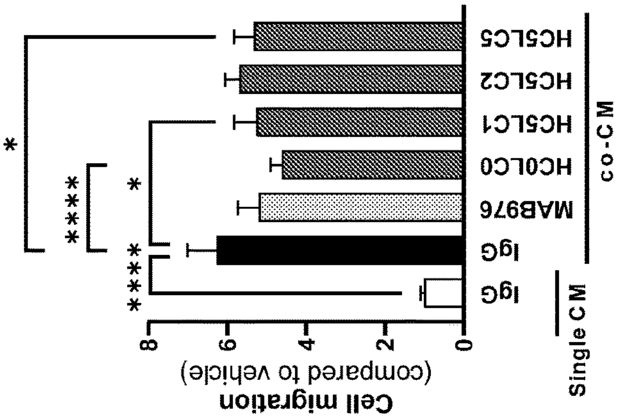
FIG. 8B shows that the effects of CXCL16 antibodies (HC4LC1, HC5LC1, HC5LC2, and HC5LC5) on the migration of CD11b+ cells.

In some embodiments, the CXCL16 antibodies disclosed herein inhibit cancer cell chemotaxis and migration. Cancer cell chemotaxis and migration can be assessed using methods well known in the art. These assays are typically designed since cells expressing CXCR6 have the tendency of migrating toward a medium containing the CXCL16 cytokine. One exemplary assay is the transwell migration assay. In brief, a vessel is divided into an upper chamber and a lower chamber, with cells expressing CXCR6 plated in the upper chamber and CXCL16 added to the medium contained in the lower chamber. The upper chamber is separated from the lower chamber with a polycarbonate membrane, which allows cells to pass through. After a period of time during which cells expressing the CXCR6 migrate to the media in the lower chamber containing CXCL16, the cells in the lower chamber are counted, which represents the number of cells that migrate to the lower chamber. When the CXCR6-expressing cells are treated with CXCL16 antibodies disclosed herein, the number of cells migrated to the lower chamber decreases, indicating the CXCL16 antibodies are capable of inhibiting chemotaxis migration. One exemplary assay is disclosed in Example 2. The results are shown in FIG. 8B, indicate that the various CXCL16 antibodies, including HC5LC1, HC5LC2, and HC5LC5, inhibits chemotaxis and migration.

In some embodiments, the CXCL16 antibodies disclosed herein inhibit bone metastasis of cancer cells. The antibodies activity in inhibiting bone metastasis is assessed with methods well-known in the art. One exemplary method uses a two-chamber system mimicking the metastatic niche of bone. In brief, an upper chamber, which is a mesh insert, is suspended within a lower chamber. The lower chamber contains cancer cells/whole marrow cell co-cultures and CXCL16 enriched fluid, mimicking the microenvironment of the metastatic niche of bone. The upper chamber harbors pre-osteoclasts from the bone marrow (for example, Human CD11b+ bone marrow myeloid cells). Typically, pre-osteoclasts differentiate into osteoclasts, which support tumor formation in the metastatic niche of the bone. Inhibiting pre-osteoclasts migration thus could effectively block tumor progression in the metastatic niche of the bone, i.e., inhibiting bone metastasis. After contacting the cells in the upper chamber with the CXCL16 antibody, cells retained in the upper chamber (aka, the mesh of the insert) are counted; the number of these cells positively correlates with the ability of the antibody to inhibiting cell recruitment into the metastatic niche:

Antibody Formats

In a further aspect of the invention, a CXCL16 antibody, in accordance with the disclosure, may be an antibody fragment, e.g., an Fv, Fab, Fab, scFv, diabody, or $F(ab')_2$ fragment. In another embodiment, the antibody is a substantially full-length antibody, e.g., an IgG antibody or other antibody class or isotype as defined herein. For a review of specific antibody fragments, see Hudson et al. Nat. Med. 9:129-134 (2003). Antibody fragments can be made by various techniques, including but not limited to proteolytic digestion of an intact antibody and production by recombinant host cells.

In some embodiments, a CXCL16 antibody, according to the present disclosure that is administered to a patient is an IgG of the IgG1 subclass. In some embodiments, such an antibody is an IgG of the IgG2, IgG3, or IgG4 subclass. In some embodiments, such an antibody is an IgM. In some embodiments, such an antibody has a lambda light chain constant region. In some embodiments, such an antibody has a kappa light chain constant region.

In some embodiments a CXCL16 antibody in accordance with the present disclosure, is in a monovalent format. In some embodiments, the tumor-targeting antibody is in a fragment format, e.g., an Fv, Fab, Fab, scFv, diabody, or $F(ab)_2$ fragment.

In some embodiments, CXCL16 antibodies disclosed herein, including antibody fragments, of the present disclosure comprises an Fc region that has effector function, e.g, exhibits antibody-dependent cellular cytotoxicity (ADCC), antibody-dependent cellular phagocytosis (ADCP), and/or complement-dependent cytotoxicity (CDC). In some embodiments, the Fc region may be an Fc region engineered to alter one or more functional properties of the antibody, such as serum half-life, complement fixation, Fc receptor binding, and/or ADCC. Accordingly, an Fc region can comprise additional mutations to increase or decrease effector functions, i.e., the ability to induce certain biological functions upon binding to an Fc receptor expressed on an immune cell. Immune cells include, but are not limited to, monocytes, macrophages, neutrophils, dendritic cells, eosinophils, mast cells, platelets, B cells, large granular lymphocytes, Langerhans' cells, natural killer (NK) cells, and cytotoxic T cells.

In some embodiments, an Fc region described herein can include additional modifications that modulate effector function. Examples of Fc region amino acid mutations that modulate an effector function include, but are not limited to, one or more substitutions at positions 228, 233, 234, 235, 236, 237, 238, 239, 243, 265, 269, 270, 297, 298, 318, 326, 327, 329, 330, 331, 332, 333, and 334 (EU numbering scheme) of an Fc region.

Illustrative substitutions that decrease effector functions include the following: position 329 may have a mutation in which proline is substituted with a glycine or arginine or an amino acid residue large enough to destroy the Fc/Fcγ receptor interface that is formed between proline 329 of the Fc and tryptophan residues Trp 87 and Trp 110 of FcγRIII. Additional illustrative substitutions that decrease effector functions include S228P, E233P, L235E, N297A, N297D, and P331S. Multiple substitutions may also be present, e.g., L234A and L235A of a human IgG1 Fc region; L234A. L235A. and P329G of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fe region; L235A, G237A, and E318A of a human IgG4 Fc region; and S228P and L236E of a human IgG4 Fc region, to decrease effectors functions. Examples of substitutions that increase effector functions include, e.g., E333A, K326W/E333S, S239D/1332E/G236A, S239D/A330L/1332E, G236A/S239D/A330L/1332E, F243L, G236A. and S298A/E333A/K334A. In some embodiments, the Fc mutations include P329G. L234A. L235A. or a combination thereof. Descriptions of amino acid mutations in an Fc region that can increase or decrease effector functions can be found in, e.g. Wang et al., Protein Cell. 9(1): 63-73, 2018; Saunders, Front Immunol. June 7, eCollection, 2019; Kellner et al., Transfus Med Hemother. 44(5): 327-336, 2017; and Lo et al., J Biol Chem. 292 (9): 3900-3908, 2017.

In some embodiments, an Fc region may have one or more amino acid substitutions that modulate ADCC. e.g., substitutions at positions 298, 333, and/or 334 of the Fc region according to the EU numbering scheme. Specifically, S298A, E333A, and K334A can be introduced to an Fc region to increase the affinity of the Fc region to FcγRIIIa and decrease the affinity of the Fc region to FcγRIIa and FcγRIIb.

An Fc region can also comprise additional mutations to increase serum half-life. Through enhanced binding to the neonatal Fe receptor (FcRn), such mutations in an Fc region can improve antibody pharmacokinetics. Examples of substitutions in an Fc region that increase the serum half-life of an antibody include, e.g., M252Y/S254T/T256E, T250Q/M428L, N434A, N434H. T307A/E380A/N434A. M428L/N434S, M252Y/M428L. D259I/V308F. N434S, V308W. V308Y. and V308F. Descriptions of amino acid mutations in an Fc region that can increase the serum half-life of an antibody can be found in, e.g., Dumet et al., MAbs. 26:1-10, 2019; Booth et al., MAbs. 10(7):1098-1110, 2018; and Dall'Acqua et al., J Biol Chem. 281(33):23514-24, 2006.

Furthermore, in some embodiments, an antibody of the disclosure may be chemically modified (e.g., one or more chemical moieties can be attached to the antibody) or be modified. e.g., produced in cell lines and/or in cell culture conditions to alter its glycosylation (e.g., hypofucosylation, afucosylation, or increased sialylation), to change one or more functional properties of the antibody. For example, the antibody can be linked to one of a variety of polymers, for example, polyethylene glycol. In some embodiments, an antibody may comprise mutations to facilitate linkage to a chemical moiety and/or to alter residues that are subject to post-translational modifications, e.g., glycosylation.

In some embodiments, a CXCL16 antibody described herein comprise an Fc region having altered glycosylation that increases the ability of the antibody to recruit NK cells and/or increase ADCC. In some embodiments, the Fc region comprises glycan containing no fucose (i.e., the Fe region is afucosylated). Afucosylated antibodies can be produced using cell lines that express a heterologous enzyme that depletes the fucose pool inside the cell (e.g., GLYMAXX® by ProBioGen AG. Berlin, Germany). Non-fucosylated antibodies can also be produced using a host cell line in which the endogenous α-1,6-fucosyltransferase (FUT8) gene is deleted. See Satoh, M. et al., "Non-fucosylated therapeutic antibodies as next-generation therapeutic antibodies," Expert Opinion on Biological Therapy, 6:11, 1161-1173, DOI: 10.1517/14712598.6.11.1161.

In some embodiments, a CXCL16 antibody is constructed as a multivalent antibody. In some embodiments, a CXCL16 antibody is constructed as a tetravalent molecule, comprising four CXCL16 binding arms per molecule. Such constructs exhibit increased ADCC activity, as well as increased binding to tumor cells a measured by flow cytometry.

In some embodiments, a CXCL16 antibody of the present disclosure is employed in a bispecific or multi-specific format, e.g., a tri-specific format. For example, in some embodiments, the antibody may be incorporated into a bispecific or multi-specific antibody that comprises a further binding domain that binds to the same or a different antigen.

There are a variety of possible formats that can be used in bispecific or multi-specific antibodies. The formats can vary elements such as the number of binding arms, the format of each binding arm (e.g., Fab, scFv, scFab, or VH-only), the number of antigen binding domains present on the binding arms, the connectivity and geometry of each arm with respect to each other, the presence or absence of an Fc domain, the Ig class (e.g., IgG or IgM), the Fc subclass (e.g., hIgG1, hIgG2, or hIgG4), and any mutations to the Fe (e.g., mutations to reduce or increase effector function or extend serum half-life). Also see Speiss et al., Alternative Molecular Formats and Therapeutic Applications for Bispecific Antibodies. Mol Immunol, 67, 95-106 (2015), FIG. 1, for examples of bispecific and multispecific formats.

CXCL16 Antibody Conjugates/Co-Stimulatory Agents

In a further aspect, a CXCL16 antibody of the present invention may be conjugated or linked to therapeutic, imaging/detectable moieties, or enzymes. For example, the tumor-targeting antibody may be conjugated to a detectable marker, a cytotoxic agent, an immunomodulating agent, an imaging agent, a therapeutic agent, an oligonucleotide, or an enzyme. Methods for conjugating or linking antibodies to a desired molecule are well known in the art. The moiety may be linked to the antibody covalently or by non-covalent linkages.

In some embodiments, the antibody is conjugated, either directly or via a cleavable or non-cleavable linker, to a cytotoxic moiety or other moiety that exerts their effects on critical cellular processes required for survival ("payload"). In some embodiments, the payloads are microtubule inhibitors that induce apoptosis in cells undergoing mitosis by, for example, causing cell cycle arrest at G2/M. Nonlimiting examples of microtubule inhibitors that can be used include maytansine derivatives (DM1/DM4), or auristatins (MMAE/MMAF) and variants thereof, such as monomethyl auristatin D, PF-06380101, duostatin5, AS269, Tap 18Hr1, AGD-0182, HPA-Auristatin F. In some embodiments, the payload is a tubulin-targeting agent, for example, hemiasterlin, tubulysin, or eribulin. In some embodiments, the payloads are DNA-damaging payloads, which include enediynes (calicheamicin), duocarmycin derivatives, pyrrolobenzodiazepine dimers (PBD dimers), and indolinobenzodiazepine pseudo-dimers.

In some embodiments, the antibody is conjugated to a cytotoxic agent including, but not limited to, e.g., auristatin, ricin A chain, doxorubicin, daunorubicin, a maytansinoid, taxol, ethidium bromide, mitomycin, etoposide, tenoposide, vincristine, vinblastine, colchicine, dihydroxy anthracin dione, methotrexact, actinomycin, a diphtheria toxin, extotoxin A from *Pseudomonas, Pseudomonas* exotoxin40, abrin, abrin A chain, modeccin A chain, alpha sarcin, gelonin, mitogellin, restrictocin, cobran venom factor, a ribonuclease, engineered Shiga toxin, phenomycin, enomycin, curicin, crotin, calicheamicin. *Saponaria officinalis* inhibitor, glucocorticoid, auristatin, auromycin, yttrium, bismuth, combrestatin, duocarmycins, dolastatin, cc1065, or a cisplatin. In some embodiments, the antibody may be linked to an agent such as an enzyme inhibitor, a proliferation inhibitor, a lytic agent, a DNA or RNA synthesis inhibitor, a membrane permeability modifier, a DNA metabolite, a dichloroethylsulfide derivative, a protein production inhibitor, a ribosome inhibitor, or an inducer of apoptosis. In some embodiments, the antibody is conjugated to a drug such as a topoisomeriase inhibitor, e.g., a topoisomeraise I inhibitor. Topoisomeraise I inhibitors include but are not limited to quinoline alkaloids (SN-38, DXd).

In some embodiments, a CXCL16 antibody as described herein is joined to a molecule that facilitates the transport of the antibody across a biological membrane, e.g., by enhancing penetration of the membrane, facilitating protein translocation across membranes. Thus, for example, the antibody may be linked to a cell penetration agent, such as a cell-penetrating peptide. Examples of cell-penetrating peptides include TAT, penetrating, polyarginine molecules, Kunitz domain-derived peptides, e.g., angiopep-2. SynB, buforin, transportan, amphiphathic peptides, and others. In some embodiments, the antibody may be conjugated with a cationic molecule such as a polyamine. In some embodiments, the antibody may be conjugated to an agent that facilitates transport across the blood-brain barrier, e.g., transcytosis. Thus, for example, the antibody may be conjugated to an agent that binds to internalized endothelial cell receptors, e.g., CXCR6 receptor, insulin receptor, insulin-like growth factor receptor, or a low-density lipoprotein receptor, and the like. In some embodiments, the antibody may be conjugated to a toxin facilitating the entry of the antibody into the cytoplasm, e.g., Shiga toxin. In some embodiments, a CXCL16 antibody, as described herein, can be conjugated to an engineered toxin body (ETBs) to facilitate the internalization of the antibody into a cell.

In some embodiments, a CXCL16 antibody described herein is conjugated or administered with a polypeptide immunomodulating agent, e.g., an adjuvant. Examples of immunomodulating agents include, but are not limited to, cytokines (e.g., transforming growth factor-β (TGFβ)), growth factors, lymphotoxins, tumor necrosis factor (TNF), hematopoietic factors, interleukins (e.g., interleukin-1 (IL-1), IL-2. IL-3, IL-6, IL-10, IL-12, IL-15, an IL-15/IL-15Rα, e.g., sushi domain, complex. IL-18, and IL-21), colony stimulating factors (e.g., granulocyte-colony stimulating factor (G-CSF) and granulocyte macrophage-colony stimulating factor (GM-CSF), interferons (e.g., interferon-α, -β or -γ, erythropoietin and thrombopoietin, or a combination thereof. In some embodiments, the antibody is linked or administered with a compound that stimulates the innate immune system, such as an adjuvant, a Toll-like receptor (TLR) agonist, a C-type lectin receptor (CLR) agonist, a retinoic acid-inducible gene I-like receptor (RLR) agonist, a saponin, a polysaccharide such as chitin, chitosan, β-glucan, an ISCOM, QS-21, a stimulator of interferon genes (STING) agonist, or another immunopotentiating agent.

In some embodiments, a CXCL16 antibody described herein is conjugated to or administered with an IL-15 receptor agonist, such as an IL-15 fusion construct, an IL-15:IL-15Rα fusion construct or a single-chain IL-15:IL-15Ra (sushi) fusion construct. In one embodiment, the tumor-targeting antibody conjugated to an IL-15 receptor agonist is a bispecific or multispecific antibody. In some embodiments, the antibody is a bispecific or multispecific antibody comprising an antigen binding domain described herein that further comprises an IL-15 receptor agonist.

In one embodiment, a CXCL16 antibody described herein is administered with a single-chain IL-15:IL-15Rα (sushi) fusion construct. In some embodiments, a CXCL16 antibody is administered with a polymer-conjugated IL-15 construct, such as NKTR-255.

The IL-15:IL-15Rα single chain constructs can be administered to a subject comprising a therapeutically effective dose, for example, in the range of less than 0.01 mg/kg body weight to about 25 mg/kg body weight, or 0.1-10 mg/kg, or in the range 1 mg-2 g per patient, or approximately 50 mg-1000 mg/patient.

Figure 9A:
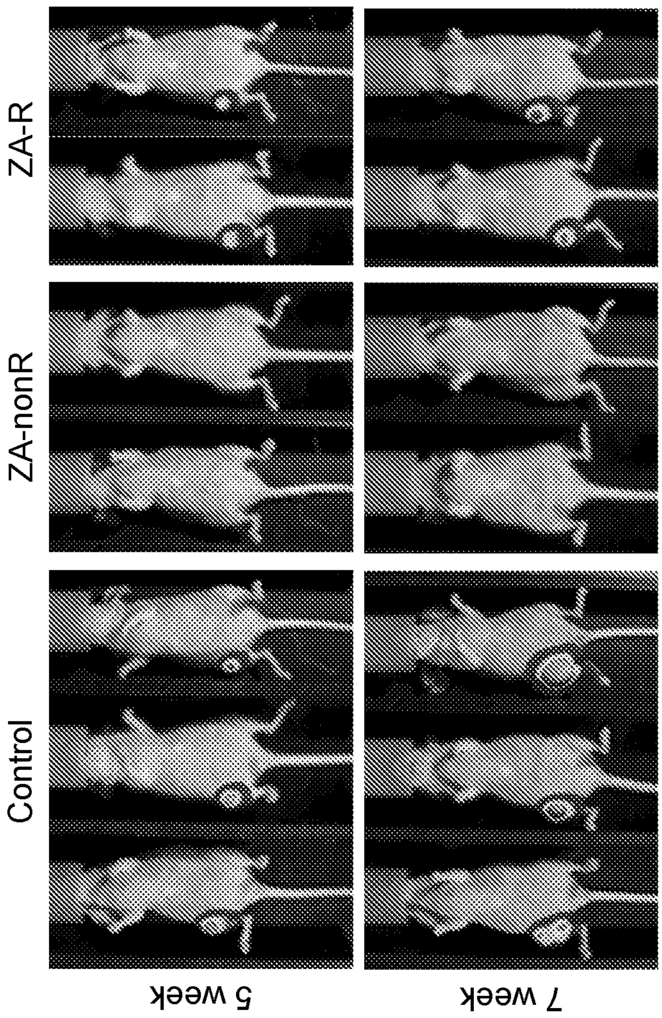
FIGS. 9A, 9B, and 9C show higher CXCL16 concentration was detected in bone marrow serum of zolendronic acid (ZA)-resistant bone metastasis.
Figure 9C:
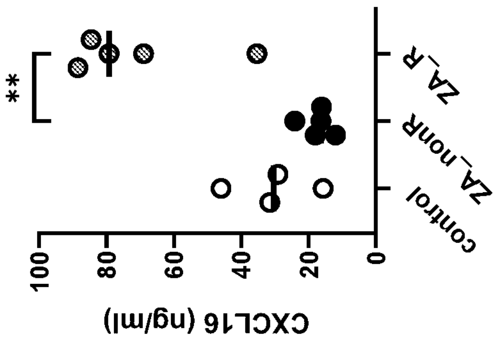
Figure 9B:
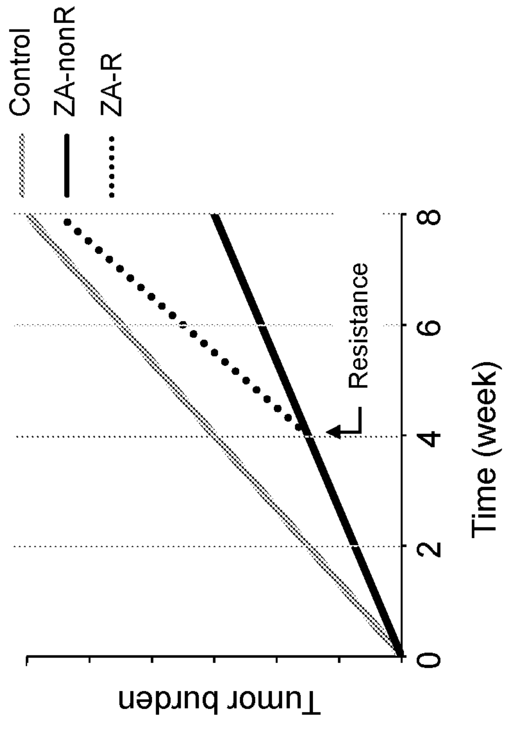

In one embodiment, the single-chain IL-15 fusion construct comprises IL-15 joined to IL-15Rα (sushi) with a polypeptide linker. In one embodiment, the single-chain IL-15 fusion construct is joined via a polypeptide linker to another protein, such as an Fc for long half-life. See, for example. FIG. 9B in WO2018071919A1 (corresponding to U.S. patent Ser. No. 10/550,185). In one embodiment, the IL-15 is joined or fused to the N-terminus of the heavy chain of an Fc, and IL-15Rx (sushi) is joined or fused to the other Fc heavy chain N-terminus, using a heavy chain heterodimerization technology to form the desired hybrid Fc. See, for example, FIG. 9A in WO2018071919A1.

In some embodiments, the antibody may be linked to a radionuclide, an iron-related compound, a dye, a fluorescent agent, or an imaging agent. In some embodiments, an antibody may be linked to agents, such as, but not limited to, metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores.

In one embodiment of any of the above constructs, the CXCL16 antibody is any one of HC4LC1, HC5LC1, HC5LC2, HC5LC3, and HC5LC5. In one embodiment of any of the above constructs, the tumor-targeting binding domain comprises the VH and VL sequences of HC4LC1, HC5LC1, HC5LC2. HCSLC3, and HC5LC5.

Generation of Antibodies

The antibodies disclosed are commonly produced using vectors and recombinant methodology well known in the art (see, e.g., Sambrook & Russell, Molecular Cloning: A Laboratory Manual, Cold Spring Harbor Laboratory Press; Ausubel, Current Protocols in Molecular Biology). Reagents, cloning vectors, and kits for genetic manipulation are available from commercial vendors. Accordingly, in a further aspect of the invention, provided herein are isolated nucleic acids encoding a $V_H$ and/or $V_L$ region, or fragment thereof, of any of the tumor-targeting antibodies as described herein; vectors comprising such nucleic acids and host cells into which the nucleic acids are introduced that are used to replicate the antibody-encoding nucleic acids and/or to express the antibodies. Such nucleic acids may encode an amino acid sequence containing the $V_L$ and/or an amino acid sequence containing the $V_H$ of the tumor-targeting antibody (e.g., the light and/or heavy chains of the antibody). In some embodiments, the host cell contains (1) a vector containing a polynucleotide that encodes the VL amino acid sequence and a polynucleotide that encodes the $V_H$ amino acid sequence, or (2) a first vector containing a polynucleotide that encodes the $V_L$ amino acid sequence and a second vector containing a polynucleotide that encodes the $V_H$ amino acid sequence.

In a further aspect, the invention provides a method of making a CXCL16 antibody as described herein. In some embodiments, the method includes culturing a host cell as described in the preceding paragraph under conditions suitable for expression of the antibody. In some embodiments, the antibody is subsequently recovered from the host cell (or host cell culture medium).

Suitable vectors containing polynucleotides encoding antibodies of the present disclosure, or fragments thereof, include cloning vectors and expression vectors. While the cloning vector selected may vary according to the host cell intended to be used, useful cloning vectors generally can self-replicate, may possess a single target for a particular restriction endonuclease, and/or may carry genes for a marker that can be used in selecting clones containing the vector. Examples include plasmids and bacterial viruses, e.g., pUC18, pUC19. Bluescript (e.g., pBS SK+) and its derivatives, mp18, mpl9, pBR322, pMB9, ColE1 plasmids, pCR1. RP4, phage DNAs, and shuttle vectors. These and many other cloning vectors are available from commercial vendors, such as pFUSE, pTRIOZ, pETEv2, TGEX-HC-hG1, TGEX-LC-hk, pOpti VEC, pCDNA3.3, pTRIOz, pFUSECHig, pFUSE-CLig or pOptiVEC.

Expression vectors generally are replicable polynucleotide constructs that contain a nucleic acid of the present disclosure. The expression vector can be replicable in the host cells either as episomes or as an integral part of the chromosomal DNA. Suitable expression vectors include but are not limited to plasmids and viral vectors, including adenoviruses, adeno-associated viruses, retroviruses, and any other vector.

Suitable host cells for expressing an antibody as described herein include both prokaryotic or eukaryotic cells. For example, an CXCL16 antibody may be produced in bacteria, when glycosylation and Fe effector function are not needed. After expression, the antibody may be isolated from the bacterial cell paste in a soluble fraction and can be further purified. Alternatively, the host cell may be a eukaryotic host cell, including eukaryotic microorganisms, such as filamentous fungi or yeast, including fungi and yeast strains whose glycosylation pathways have been "humanized," resulting in the production of an antibody with a partially or fully human glycosylation pattern, vertebrate, invertebrate, and plant cells. Examples of invertebrate cells include insect cells. Numerous baculoviral strains have been identified which may be used in conjunction with insect cells. Plant cell cultures can also be utilized as host cells.

In some embodiments, vertebrate host cells are used for producing an antibody of the present disclosure. For example, mammalian cell lines such as a monkey kidney CV1 line transformed by SV40 (COS-7); human embryonic kidney line (293 or 293 cells as described, e.g., in Graham et al., *J. Gen Virol.* 36:59, 1977; baby hamster kidney cells (BHK); mouse sertoli cells (TM4 cells as described, e.g., in Mather, *Biol. Reprod.* 23:243-251, 1980 monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described. e.g., in Mather et al., Annals N.Y. Acad. Sci. 383:44-68, 1982; MRC 5 cells; and FS4 cells may be used to express an tumor-targeting antibodies. Other useful mammalian host cell lines include Chinese hamster ovary (CHO) cells, including DHFR-CHO cells (Urlaub et al., *Proc. Natl. Acad. Sci. USA* 77:4216, 1980); and myeloma cell lines such as Y0, NS0 and Sp2/0. Host cells of the present disclosure also include, without limitation, isolated cells, in vitro cultured cells, and ex vivo cultured cells. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268, 2003.

In some embodiments, a CXCL16 antibody of the present invention is produced by a CHO cell line, e.g., the CHO-K1 cell line. One or more expression plasmids can be introduced that encode heavy and light chain sequences. For example, in one embodiment, an expression plasmid encoding a heavy chain and an expression plasmid encoding a light chain are transfected into host cells as linearized plasmids at a ratio of 1:1 in the CHO-K1 host cell line using reagents such as Freestyle Max reagent. Fluorescence-activated cell sorting (FACS) coupled with single cell imaging can be used as a cloning method to obtain a production cell line.

A host cell transfected with an expression vector encoding a CXCL16 antibody of the present disclosure, or fragment thereof, can be cultured under appropriate conditions to allow expression of the polypeptide to occur. The polypeptides may be secreted and isolated from a mixture of cells and medium containing the polypeptides. Alternatively, the polypeptide may be retained in the cytoplasm or in a membrane fraction and the cells harvested, lysed, and the polypeptide isolated using a desired method.

In some embodiments, an antibody of the present disclosure can be produced by in vitro synthesis (see, e.g., Sutro Biopharma biochemical protein synthesis platform).

In some embodiments, provided herein is a method of generating variants of a CXCL16 antibody as disclosed herein. Thus, for example, a construct encoding a variant of a $V_H$ CDR3 as described herein can be modified and the $V_H$ region encoded by the modified construct can be tested for binding activity to target cells (for example, breast cancer cells) and/or in vivo tumor-targeting activity in the context of a $V_H$ region as described herein, that is paired with a $V_L$ region or variant region as described herein. Similarly, a construct encoding a variant of a $V_L$ CDR3 as described herein can be modified and the $V_L$ region encoded by the modified construct can be tested for binding to target cells, or other tumor cells, and/or in vivo tumor-targeting activity efficacy. Such an analysis can also be performed with other CDRs or framework regions and an antibody having the desired activity can then be selected.

Treatment of Cancer

In a further aspect, a CXCL16 antibody as provided herein, or a variant thereof as described herein, can be used and a therapeutic agent to treat cancer.

In some aspects, the disclosure provides methods of identifying subjects who are candidates for treatment with a CXCL16 antibody having tumor-targeting effects. Thus, in one embodiment, the invention provides a method of identifying a patient who can benefit from treatment with a CXCL16 antibody of the present disclosure. In one embodiment, the patient has cancer that overexpresses CXCL16, i.e., expresses CXCL16 at a level that is at least 10%, at least 20%, at least 30%, at least 40%, at least 50%, at least 80%, or at 100% higher than the normal tissue. In some embodiments, the cancer sample is from a primary tumor. In alternative embodiments, the cancer sample is a metastatic lesion. Binding of antibody to cancer cells through a binding interaction with the CXCL16 can be measured using any assay, such as bio-light interferometry (ForteBio), immunohistochemistry or flow cytometry. In some embodiments, binding of antibody to at least 0.2%, 0.5%, or 1%, or at least 5% or 10%, or at least 20%, 30%, or 50%, of the tumor cells in a sample may be used as a selection criterion for determining a patient to be treated with a CXCL16 as described herein.

A CXCL16 antibody disclosed herein can be used to treat cancer. In general, a tumor refers to an abnormally grown mass due to the autonomous overgrowth of body tissues, and tumors can be divided into benign tumors and malignant tumors. Malignant tumors grow very rapidly compared to benign tumors, and metastasis occurs while infiltrating the surrounding tissues, threatening life. Such malignant tumors are commonly referred to as "cancer". Thus, the term "cancer" refers to a disease related to the regulation of cell death or a disease caused by excessive cell proliferation when the balance of normal apoptosis is disrupted. In some cases, these abnormal hyperproliferative cells may invade surrounding tissues and organs to form a mass, and the invasion can cause destruction or deformation of the structure, and this condition is collectively called cancer.

In some embodiments, the cancer that can benefit from the treatment of a CXCL16 antibody disclosed herein is cervical cancer, lung cancer, pancreatic cancer, non-small cell lung cancer, liver cancer, colon cancer, colorectal cancer, bone cancer, skin cancer, head cancer, cervical cancer, skin melanoma, intraocular melanoma, uterine cancer, ovarian cancer, rectal cancer, liver cancer, brain tumor, bladder cancer, blood cancer, stomach cancer, perianal cancer, breast cancer, fallopian tube carcinoma, endometrial carcinoma, vaginal cancer, vulvar carcinoma. Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, bladder cancer, kidney cancer, ureter cancer, renal cell carcinoma, renal pelvic carcinoma, central nervous system tumor, primary CNS lymphoma, spinal cord tumor, brain. In some embodiment, the cancer is a glioma and pituitary adenoma.

In some embodiments, the thyroid cancer that can be treated by the CXCL16 antibody disclosed herein is an anaplastic thyroid cancer. Anaplastic thyroid cancer, also called undifferentiated thyroid cancer, has the worst prognosis among thyroid cancers. Distant metastasis to the lung or bone is often found from the beginning, and if confirmed, it is considered stage IV. The average survival period is about 3 to 6 months, an the survival rate is close to 0%.

In some embodiments, the breast cancer that can be treated with the CXCL16 antibody disclosed herein is a triple-negative breast cancer. Triple-negative breast cancer is known to lack estrogen and progesterone receptors (ER−/PR−), and HER2 gene is not expressed. Therefore, TNBC is resistant to estrogen receptor modulator (tamoxifen) and HER2 inhibitor (trastuzumab). Triple-negative breast cancer accounts for about 12-17% of all breast cancer patients in the United States, and about 15.9% of all breast cancer patients in Koreans. It is reported that the 5-year survival rate of triple-negative breast cancer patients is about 77%, which is lower than about 93% of patients with other types of breast cancer. These cancer patients may benefit from the treatment of a CXCL16 antibody disclosed herein.

Combination Therapy

In some embodiments, a CXCL16 antibody disclosed herein may be administered with one or more additional therapeutic agents, also referred to as the combination agents in this application. In some embodiments, a CXCL16 antibody disclosed herein can be administered in combination with one or more of the targeted anti-cancer agent. In some embodiments, the targeted anti-cancer agent is a therapeutic antibody, such as targeting a tumor cell antigen. Nonlimiting examples of targeted anticancer agent include cetuximab, trastuzumab, ibritumomab, rituximab, brentuximab, alemtuzumab, imatinib, nilotinib, radotinib, gefitinib, erlotinib. Afatinib, olmutinib, osimertinib, ceritinib, lapatinib, ruxoritinib, tofacitinib, vemuratinib, sunitinib, axitinib, vandetanib, dasatinib, crizotinib, zopanib, regorafenib, bevacizumab, paclitaxel, gemcitabine, docetaxel, axitinib, nintedanib, and Lenvatinib.

In some embodiments, the immune checkpoint inhibitor is selected from the group consisting of a PD-1 inhibitor, a PD-L1 inhibitor, and a CTLA-4 inhibitor, but is not limited thereto.

In some embodiments, the combination agent is a PD-L1 inhibitor. Nonlimiting examples of PD-L1 inhibitors include atezolizumab, avelumab, duvalumab, envafolimab, cosibelimab, AUNP12, CA-170, BMS-986189, nivolumab, pembrolizumab, semiplimab, spartalizumab, camrelizumab, sintilimab), may be one or more selected from the group consisting of tislelizumab, toripalimab, dostarlimab, INCMGA00012, AMP-224, and AMP-514.

In some embodiments, the combination agent is a CTLA-4 inhibitor. Nonlimiting examples of CTLA-4 inhibitors include ipilimumab and tremelimumab.

In some embodiments, the CXCL16 antibody and the combination agent may be administered simultaneously, separately, or sequentially.

In some embodiments, the CXCL16 antibody inhibits succinate metabolism.

In some embodiments, the targeted anticancer agent may be administered orally. In some embodiments, the immune checkpoint inhibitor may be administered by injection.

In some embodiments, the CXCL16 antibody and the combination agent may be provided in a single dosage form or in a single dose, respectively.

In some embodiments, the pharmaceutical composition may be to reduce the size of the tumor or inhibit tumor metastasis.

A pharmaceutical composition disclosed herein may also include a pharmaceutically acceptable salt. The term "pharmaceutically acceptable salt" herein includes salts derived from pharmaceutically acceptable inorganic acids, organic acids, or bases.

Examples of suitable acids include hydrochloric acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, gluconic acid, naphthalene-2-sulfonic acid, benzenesulfonic acid, and the like. Acid addition salts can be prepared by conventional methods, for example, by dissolving the compound in an aqueous solution of an excess of acid and precipitating the salt using a water-miscible organic solvent such as methanol, ethanol, acetone, or acetonitrile. It can also be prepared by heating an equimolar amount of the compound and an acid or alcohol in water and then evaporating the mixture to dryness, or by suction filtration of the precipitated salt.

Salts derived from suitable bases may include, but are not limited to, alkali metals such as sodium and potassium, alkaline earth metals such as magnesium, and ammonium. The alkali metal or alkaline earth metal salt can be obtained, for example, by dissolving the compound in an excess alkali metal hydroxide or alkaline earth metal hydroxide solution, filtering the undissolved compound salt, and then evaporating and drying the filtrate. In this case, it is pharmaceutically suitable to prepare a sodium, potassium or calcium salt as the metal salt, and the corresponding silver salt can be obtained by reacting an alkali metal or alkaline earth metal salt with a suitable silver salt (for example, silver nitrate).

The CXCL16 antibody and/or one or more combination agents (for example, a targeted anticancer agent, an immune checkpoint inhibitor) can be appropriately adjusted in the pharmaceutical composition according to the symptoms of the disease, the degree of progression of the symptoms, the condition of the patient, and the like, for example, from 0.0001 to 0.0001 to the total weight of the composition It may be 99.9% by weight, or 0.001 to 50% by weight, but is not limited thereto. The content ratio is based on the dry amount from which the solvent is removed.

The pharmaceutical composition of the present invention may vary the content of the active ingredient according to the disease's degree and/or purpose. In some embodiments, it is in an effective dose of 0.01 μg to 10000 mg, preferably 0.1 μg to 1000 mg when administered once. It can be administered repeatedly several times a day. However, the dosage of the pharmaceutical composition is determined by considering various factors such as the formulation method, administration route and number of treatments, as well as the patient's age, weight, health status, sex, severity of disease, diet and excretion rate, etc., the effective dosage for the patient is determined. Therefore, considering this point, those of ordinary skill in the art will be able to determine an appropriate, effective dosage of the composition of the present invention. The pharmaceutical composition according to the present invention is not particularly limited in its formulation, administration route and administration method as long as the effect of the present invention is exhibited.

The pharmaceutical composition according to the present invention may further include suitable carriers, excipients and diluents commonly used in the preparation of pharmaceutical compositions. The excipient may be, for example, at least one selected from the group consisting of a diluent, a binder, a disintegrant, a lubricant, an adsorbent, a humectant, a film-coating material, and a controlled-release additive.

The pharmaceutical composition according to the present invention can be prepared according to a conventional method, respectively, in powders, granules, sustained-release granules, enteric granules, liquids, eye drops, elixirs, emulsions, suspensions, spirits, troches, fragrances, and limonades, tablets, sustained release tablets, enteric tablets, sublingual tablets, hard capsules, soft capsules, sustained release capsules, enteric capsules, pills, tinctures, soft extracts, dry extracts, fluid extracts, injections, capsules, perfusates, plaster, lotions, pasta, sprays, inhalants, patches, sterile injection solutions, or external preparations such as aerosols can be formulated and used. The external preparations may be creams, gels, patches, sprays, ointments, warning agents, lotion, liniment, pasta, or cataplasma.

Carriers, excipients, and diluents that may be included in the pharmaceutical composition according to the present invention include lactose, dextrose, sucrose, oligosaccharide, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil.

In the case of a formulation, it is prepared using diluents or excipients such as fillers, extenders, binders, wetting agents, disintegrants, and surfactants that are usually used.

As additives for tablets, powders, granules, capsules, pills, and troches according to the present invention, corn starch, potato starch, wheat starch, lactose, sucrose, glucose, fructose, di-mannitol, precipitated calcium carbonate, synthetic aluminum silicate, phosphoric acid Calcium monohydrogen, calcium sulfate, sodium chloride, sodium hydrogen carbonate, purified lanolin, microcrystalline cellulose, dextrin, sodium alginate, methylcellulose, sodium carboxymethylcellulose, kaolin, urea, colloidal silica gel, hydroxypropyl starch, hydroxypropylmethyl excipients such as cellulose (HPMC), HPMC 1928, HPMC 2208, HPMC 2906, HPMC 2910, propylene glycol, casein, calcium lactate, and Primogel; Gelatin, gum arabic, ethanol, agar powder, cellulose phthalate acetate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch powder, hydroxypropylcellulose, hydroxypropylmethylcellulose, polyvinyl alcohol, polyvinylpyrrolidone, etc. Hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxy Propylcellulose, dextran, ion exchange resin, polyvinyl acetate, formaldehyde treated casein and gelatin, alginic acid, amylose, guar gum, sodium bicarbonate, polyvinylpyrrolidone, calcium phosphate, gelled starch, gum arabic, disintegrants such as amylopectin, pectin, sodium polyphosphate, ethyl cellulose, sucrose, magnesium aluminum silicate, di-sorbitol solution, light anhydrous silicic acid; Calcium stearate, magnesium stearate, stearic acid, hydrogenated vegetable oil, talc, Limestone, kaolin, petrolatum, sodium stearate, cacao butter, sodium salicylate, magnesium salicylate, polyethylene glycol 4000, 6000, liquid paraffin, hydrogenated soybean oil (Lubri wax), aluminum stearate, zinc stearate, sodium lauryl sulfate, magnesium oxide, macrogol (Macrogol), synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, light silicic anhydride and the like lubricants; can be used.

As additives for the liquid formulation according to the present invention, water, diluted hydrochloric acid, diluted sulfuric acid, sodium citrate, monostearate sucrose, polyoxyethylene sorbitol fatty acid esters (Twinester), polyoxyethylene monoalkyl ethers, lanolin ethers. Lanolin esters, acetic acid, hydrochloric acid, aqueous ammonia, ammonium carbonate, potassium hydroxide, sodium hydroxide, prolamine, polyvinylpyrrolidone, ethyl cellulose, sodium carboxymethyl cellulose, etc. can be used.

In the syrup, according to the present invention, a sucrose solution, other sugars or sweeteners may be used, and if necessary, a fragrance, colorant, preservative, stabilizer, suspending agent, emulsifier, thickening agent, etc. may be used.

Purified water may be used in the emulsion according to the present invention, and if necessary, an emulsifier, preservative, stabilizer, fragrance, and the like, may be used.

Suspending agents such as acacia, tragacantha, methylcellulose, carboxymethylcellulose, sodium carboxymethylcellulose, microcrystalline cellulose, sodium alginate, hydroxypropylmethylcellulose, HPMC 1828, HPMC 2906, HPMC 2910 may be used in the suspending agent according to the present invention. If necessary, surfactants, preservatives, stabilizers, colorants, and fragrances may be used.

The injection according to the present invention includes distilled water for injection, 0.9% sodium chloride injection, ring gel injection, dextrose injection, dextrose+sodium chloride injection. PEG (PEG), lactated ring gel injection, ethanol, propylene glycol, non-volatile oil-sesame oil, solvents such as cottonseed oil, peanut oil, soybean oil, corn oil, ethyl oleate, isopropyl myristate, and benzene benzoate; Solubilizing aids such as sodium benzoate, sodium salicylate, sodium acetate, urea, urethane, monoethylacetamide, butazolidine, propylene glycol, tweens, nijeongtinamide, hexamine, and dimethylacetamide; Weak acids and their salts (acetic acid and sodium acetate), weak bases and their salts (ammonia and ammonium acetate), organic compounds, proteins, buffers such as albumin. peptone, gum; isotonic agents such as sodium chloride; Stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), ethylenediaminetetraacetic acid; sulphating agents such as sodium bisulfide 0.1%, sodium formaldehyde sulfoxylate, thiourea, disodium ethylenediaminetetraacetate, acetone sodium bisulfite; analgesic agents such as benzyl alcohol, chlorobutanol, procaine hydrochloride, glucose, and calcium gluconate; suspending agents such as SiMC sodium, sodium alginate, Tween 80, and aluminum monostearate.

The suppository according to the present invention includes cacao fat, lanolin, witepsol, polyethylene glycol, glycerogelatin, methyl cellulose, carboxymethyl cellulose, a mixture of stearic acid and oleic acid, Subanal, cottonseed oil, peanut oil, palm oil, cacao butter+Cholesterol, Lecithin, Lanet Wax, Glycerol Monostearate, Tween or Span, Imhausen, Monolene (Propylene Glycol Monostearate), Glycerin, Adeps Solidus, Butyrum Tego-G), Cebes Pharma 16, Hexalide Base 95, Cotomar, Hydroxote SP, S-70-XXA, S-70-XX75 (S-70-XX95), Hydro Hydrokote 25, Hydrokote 711, Idropostal, Massa estrarium, A, AS, B, C, D, E, I, T, Massa-MF, Masupol, Masupol-15, Neosupostal-N, Paramound-B, Suposhiro (OSI, OSIX, A, B, C, D, H, L), Suppository IV type (AB, B, A, BC, BBG, E, BGF, C, D, 299), supostal (N, Es), Wecobi (W, R, S, M, Fs), tester triglyceride base (TG-95, MA, 57) and the like.

Solid preparations for oral administration include tablets, pills, powders, granules, capsules, and the like, such preparations include at least one excipient in the extract, for example, starch, calcium carbonate, sucrose) or lactose, gelatin, and the like. In addition to simple excipients, lubricants such as magnesium stearate talc can also be used.

Liquid formulations for oral administration include suspensions, internal solutions, emulsions, syrups, and the like. In addition to water and liquid paraffin, which are commonly used simple diluents, various excipients such as wetting agents, sweeteners, fragrances, and preservatives may be included. Formulations for parenteral administration include sterile aqueous solutions, non-aqueous solutions, suspensions, emulsions, freeze-dried preparations, and suppositories. Non-aqueous solvents and suspending agents include propylene glycol, polyethylene glycol, vegetable oils such as olive oil, and injectable esters such as ethyl oleate.

The pharmaceutical composition, according to the present invention, is administered in a pharmaceutically effective amount. In the present invention. "pharmaceutically effective amount" means an amount sufficient to treat a disease with a reasonable benefit/risk ratio applicable to medical treatment, and the effective dose level is determined by the type, severity, drug activity, and type of the patient's disease; Sensitivity to the drug, administration time, administration route and excretion rate, treatment period, factors including concurrent drugs and other factors well known in the medical field may be determined. In exemplary embodiments, a CXCL16 antibody is administered 100 mcg/20 g/day, twice a week, via intraperitoneal injection; or 50 mcg/20 g/day, three times a week, via intravenous injection; the PD-L1 peptide is administered 0.1 mg/20 g/day, five times a week, via intraperitoneal injection; Lenvatinib is administered 30 m/kg/day, via oral administration; paclitaxel is administered 10 mg/kg, twice a week, via intraperitoneal injection or 10 mg/kg/day, once a week, via intraperitoneal injection.

The pharmaceutical composition according to the present invention may be administered as an individual therapeutic agent or in combination with other therapeutic agents, may be administered sequentially or simultaneously with conventional therapeutic agents.

The pharmaceutical composition and the other therapeutic agents may be administered single or multiple. One of ordinary skill in the art may consider all the factors above and determine an amount capable of obtaining the maximum effect with a minimum amount or no side effects.

The pharmaceutical composition of the present invention may be administered to an individual via various routes. All modes of administration can be envisaged, for example, oral administration, subcutaneous injection, intraperitoneal administration, intravenous injection, intramuscular injection, paraspinal (intrathecal) injection, sublingual administration, buccal administration, rectal insertion, vaginal It can be administered according to internal insertion, ocular administration, ear administration, nasal administration, inhalation, spraying through the mouth or nose, skin administration, transdermal administration, and the like.

The pharmaceutical composition of the present invention is determined according to the type of drug as the active ingredient along with various related factors such as the disease to be treated, the route of administration, the patient's age, sex, weight, and the severity of the disease.

In some embodiments, the present disclosure provides a CXCL16 antibody; and one or more combination agents selected from the group consisting of a targeted anticancer agent and an immune checkpoint inhibitor as an active ingredient, wherein the CXCL16 antibody; And the combination agent is administered simultaneously, separately or sequentially, it provides a pharmaceutical combination formulation for the prevention or treatment of cancer.

The CXCL16 antibody, targeted anticancer agent, and immune checkpoint inhibitor, which are components of the pharmaceutical combination preparation of the present invention, may be used as such or in the form of a salt, preferably a pharmaceutically acceptable salt.

The pharmaceutical combination formulation of the present invention may include a CXCL16 antibody as a component according to the administration method and route of administration. In some embodiments, one or more combination agents selected from the group consisting of a targeted anticancer agent and an immune checkpoint inhibitor may also be included in one formulation with the CXCL16 antibody at the same time. In some embodiments, the combination agents and the CXCL16 antibody may be individually formulated and contained in one package depending on a daily or once-daily dosage unit. The specific formulation method of the pharmaceutical combination disclosed herein will be known or apparent to those skilled in the art and described in for example. Remington's Pharmaceutical Sciences, 19th ed., Mack Publishing Company, Easton, PA, 1995). A CXCL16 antibody, a component of the pharmaceutical combination formulation according to the present invention and one or more combination agents selected from the group consisting of a targeted anti-cancer agent and an immune checkpoint inhibitor may be administered simultaneously or separately or according to a predetermined sequence. As used herein, the term "simultaneous administration" means the CXCL16 antibody and the combination are taken together or at substantially the same time (eg, 15 minutes or less between administrations), so that in the case of oral administration, the two components are present in the stomach simultaneously. When administered concurrently, the combination may be formulated to be included simultaneously in one formulation. In the case of oral administration, it may be preferably formulated so that the daily dose is all included in a single dose; however, it may also be formulated to be administered in divided doses such as 2, 3, 4 times a day.

EXEMPLARY EMBODIMENTS

Embodiment 1. A pharmaceutical composition for preventing or treating cancer, comprising a CXCL16 antibody as an active ingredient.

Embodiment 2. A method of preventing or treating cancer in a subject, comprising administering the pharmaceutical composition of Embodiment 1 and one or more combination agents selected from the group consisting of chemotherapeutic agents, targeted anticancer agents and immune checkpoint inhibitors.

Embodiment 3: The method of Embodiment(s) 2, wherein the targeted anticancer agent is cetuximab, trastuzumab, ibritumomab, rituximab, brentuximab, alemtuzumab, imatinib, nilotinib, radotinib, gefitinib, erlotinib, afatinib, olmutinib, osimertinib, ceritinib, lapatinib, ruxoritinib, tofacitinib, vemuratinib, sunitinib, axitinib, vandetanib, dasatinib, crizotinib, pazopanib, lego A pharmaceutical composition, characterized in that at least one selected from the group consisting of lafenib, bevacizumab, paclitaxel, gemcitabine, docetaxel, axitinib, nintedanib, and lenvatinib.

Embodiment 4: The method of Embodiment(s) 2, wherein the immune checkpoint inhibitor is one selected from the group consisting of a PD-1 inhibitor, a PD-L1 inhibitor, and a CTLA-4 inhibitor.

Embodiment 5: The method of embodiment(s) 4, wherein the PD-L1 inhibitor is one of atezolizumab, avelumab, duvalumab, envafolimab, cosibelimab, AUNP12, CA-170 or BMS-986189.

Embodiment 6: The method of embodiment(s) 4, wherein the PD-1 inhibitor is nivolumab, pembrolizumab, semiplimab, spartalizumab, camrelizumab, sintilimab, tisrelizumab (tislelizumab), toripalimab, dostarlimab, INCMGA00012, AMP-224, or AMP-514.

Embodiment 7: The method of embodiment(s) 4, wherein the CTLA-4 inhibitor is ipilimumab, or tremelimumab.

Embodiment 8: The method of embodiment(s) 2, wherein the CXCL16 antibody and the combination agents are administered simultaneously, separately or sequentially.

Embodiment 9: The method of embodiment(s) 2, wherein the CXCL16 antibody is characterized in that it inhibits succinate metabolism, a pharmaceutical composition.

Embodiment 10: The method of embodiment(s) 2, wherein the cancer is cervical cancer, lung cancer, pancreatic cancer, non-small cell lung cancer, liver cancer, colon cancer, colorectal cancer, bone cancer, skin cancer, head cancer, cervical cancer, skin melanoma, intraocular melanoma, uterine cancer, ovarian cancer, rectal cancer, liver cancer, brain tumor, bladder cancer, blood cancer, stomach cancer, perianal cancer, breast cancer, fallopian tube carcinoma, endometrial carcinoma, vaginal cancer, vulvar carcinoma, Hodgkin's disease, esophageal cancer, small intestine cancer, endocrine adenocarcinoma, thyroid cancer, parathyroid cancer, adrenal cancer, Soft tissue sarcoma, urethral cancer, penile cancer, prostate cancer, bladder cancer, kidney cancer, ureter cancer, renal cell carcinoma, renal pelvic carcinoma, CNS central nervous system tumor, primary CNS lymphoma, spinal cord tumor, brainstem glioma, and pituitary gland tumor.

Embodiment 11: The method of embodiment(s) 2, wherein the targeted anticancer agent is administered orally.

Embodiment 12: The method of embodiment(s) 2, wherein the CXCL16 antibody and the combination agent are provided in a single dosage form or in a single dose, respectively.

Embodiment 13: The method of embodiment(s) 1 or 2, wherein the pharmaceutical composition reduces the size of the tumor or inhibits tumor metastasis.

Embodiment 14. A pharmaceutical combination formulation for the prevention or treatment of cancer comprising a CXCL16 antibody and one or more combination agents selected from the group consisting of chemotherapeutic agents, targeted anticancer agents, and immune checkpoint inhibitors as an active ingredient, wherein the CXCL16 antibody and the combination agent is administered simultaneously, separately, or sequentially.

Embodiment 15: A pharmaceutical composition for inhibiting cancer metastasis, wherein the pharmaceutical composition comprises a CXCL16 antibody as an active ingredient.

Embodiment 16: A pharmaceutical composition comprising a CXCL16 antibody for inhibiting cancer metastasis as an active ingredient, and one or more combination agents selected from the group consisting of chemotherapeutic agents, targeted anticancer agents, and immune checkpoint inhibitors.

Embodiment 17: A composition for diagnosing cancer comprising a CXCL16 antibody as an active ingredient.

Embodiment 18: A kit for diagnosing cancer comprising the composition of embodiment(s) 17.

All documents mentioned herein are incorporated herein by reference as if their contents were set forth herein. When introducing an element of the present invention or preferred aspect(s) thereof, the articles "a," "an," "the," and "said" refer to one or more of the elements. The terms "comprising," "including," and "having," are intended to be inclusive and mean that there may be additional elements other than the listed elements. Although the invention has been described with respect to specific aspects or aspects, it should not be construed as limiting the details of these aspects.

Hereinafter, preferred examples are presented to help the understanding of the present invention. However, the following examples are only provided for easier understanding of the present invention, and the contents of the present invention are not limited by the following examples.

Informal Sequence Listing:

```
SEQ ID NO: 1: Heavy chain variable region of HC1
QVQLVESGGGVVQPGGSLRLSCAASGFTFSNAVMNWVRQAPGKGLEWVARIRTKPNNYATFY

ADSVKGRFTFSRDNSKTMLYLQMNSLRAEDTAVYYCTAWTTEGIYWGQGTLVTVSS

SEQ ID NO: 2: Heavy chain variable region of HC2
AVQLVESGGGLVQPGGSLKISCAASGFTFSNAVMNWVRQASGKGLEWVGRIRTKPNNYATFYA

DSVKGRFTISRDDSKNTAYLQMNSLKTEDTAMYYCTAWTTEGIYWGQGTLVTVSS

SEQ ID NO: 3: Heavy chain variable region of HC3
EVQLVESGGGLVQPGGSLKLSCAASGFTFSNAVMNWVRQAPGKGLEWVGRIRTKPNNYATFYA

DSVKGRFTFSRDDSKNTAYLQMNILKTEDTAMYYCTAWTTEGIYWGQGTTVTVSS

SEQ ID NO: 4: Heavy chain variable region of HC4
EVQLVESGGGLVKPGGSLRLSCAASGFTFSNAVMNWVRQAPGKGLEWVARIRTKPNNYATFYA

DSVKGRFTFSRDDSKNTLYLQMNSLKTEDTAVYYCTAWTTEGIYWGQGTTVTVSS
```

-continued

SEQ ID NO: 5: Heavy chain variable region of HC5
EVQLVESGGGLVQPGGSLKLSCAASGFTFSNAVMNWVRQASGKGLEWVARIRTKPNNYATFYA

DSVKGRFTFSRDDSKNTAYLQMNSLKTEDTAMYYCTAWTTEGIYWGQGTLVTVSS

SEQ ID NO: 6: Light chain variable region of LC1
DIVMTQSPDSLAVSAGFTVTINCKSSQSLLYSGNQKNYLAWYQQKPGQSPKLLIYWASTRQSGV

PDRFSGSGSGTDFTLTISSVQAEDVAVYYCQQYYDTPWTFGGGTKVEIK

SEQ ID NO: 7: Light chain variable region of LC2
DIVMTQSPSSLAVSLGFTATINCKSSQSLLYSGNQKNYLAWYQQKPGQPPKLLIYWASTRQSGVP

DRFTGSGAGTDFTLTISSVQAEDLAIYYCQQYYDTPWTFGGGTKVEIK

SEQ ID NO: 8: Light chain variable region of LC3
DIQMTQSPSSLSASVGDRVTITCKSSQSLLYSGNQKNYLAWYQQKPGQSPKLLIYWASTRQSGVP

DRFSGSGSGTDFTLTISSLQAEDFATYYCQQYYDTPWTFGGGTKVEIK

SEQ ID NO: 9: Light chain variable region of LC4
DIQMTQSPSSLSASVGDRVTITCKSSQSLLYSGNQKNYLAWYQQKPGQSPKLLIYWASTRQSGVP

SRFSGSGSGTDFTLTISSLQPEDLAIYYCQQYYDTPWTFGGGTKLELK

SEQ ID NO: 10: Light chain variable region of LC5
DIVMTQSPSSLAVSAGERATINCKSSQSLLYSGNQKNYLAWYQQKPGQSPKLLIYWASTRQSGV

PDRFIGSGSGTDFTLTISSLQAEDVAIYYCQQYYDTPWTFGGGTKLELK

SEQ ID NO: 11: human CXCL16
MGRDLRPGSRVLLLLLLLLLVYLTQPGNGNEGSVTGSCYCGKRISSDSPPSVQFMNRLRKHLRA

YHRCLYYTRFQLLSWSVCGGNKDPWVQELMSCLDLKECGHAYSGIVAHQKHLLPTSPPISQASE

GASSDIHTPAQMLLSTLQSTQRPTLPVGSLSSDKELTRPNETTIHTAGHSLAAGPEAGENQKQPEK

NAGPTARTSATVPVLCLLAIIFILTAALSYVLCKRRRGQSPQSSPDLPVHYIPVAPDSNT

SEQ ID NO: 12: HCDR1
GFTFSNAVMN

SEQ ID NO: 13: HCDR2
RIRTKPNNYATFYADSVKG

SEQ ID NO: 14: HCDR3
TAWTTEGIY

SEQ ID NO: 15: LCDR1
KSSQSLLYSGNQKNYLA

SEQ ID NO: 16: LCDR2
WASTRQS

SEQ ID NO: 17: LCDR3
QQYYDTPWT

SEQ ID NO: 18: Heavy chain signal peptide
MGWTLVFLFLLSVTAGVHS

SEQ ID NO: 19: Light chain signal peptide
MVSSAQFLGLLLLCFQGTRC

SEQ ID NO: 20: CXCR6
MAEHDYHEDYGFSSFNDSSQEEHQDFLQFSKVFLPCMYLVVFVCGLVGNSLVLVISIFYHKLQSL

TDVFLVNLPLADLVFVCTLPFWAYAGIHEWVFGQVMCKSLLGIYTINFYTSMLILTCITVDRFIVV

VKATKAYNQQAKRMTWGKVTSLLIWVISLLVSLPQIIYGNVFNLDKLICGYHDEAISTVVLATQ

MTLGFFLPLLTMIVCYSVIIKTLLHAGGFQKHRSLKIIFLVMAVFLLTQMPFNLMKFIRSTHWEYY

AMTSFHYTIMVTEAIAYLRACLNPVLYAFVSLKFRKNFWKLVKDIGCLPYLGVSHQWKSSEDNS

KTFSASHNVEATSMFQL

SEQ ID NO: 21: HC-FR1
$X_1$VQLVESGGG$X_2$V$X_3$P$X_4$$X_5$SL$X_6$$X_7$SCAAS; wherein $X_1$ can be A or Q, or E; $X_2$ can be L or V; $X_3$ can be Q or K; $X_4$ can be K or G; $X_5$ can be E or G; $X_6$ can be K or R; $X_7$ can be I or L -continued SEQ ID NO: 22: HC-FR2
WVRQA$X_1$GKGLEWV$X_2$; wherein $X_1$ can be P or S; $X_2$ can be A or G.

SEQ ID NO: 23: HC-FR3
FT$X_1$SRD$X_2$SK$X_3X_4X_5$YLQM$X_6X_7$L$X_8X_9$EDTA$X_{10}$YYC; wherein $X_1$ can be F or I; $X_2$ can be D or N; $X_3$ can be S, T, or N; $X_4$ can be M or T; $X_5$ can be V, L, or A; $X_6$ can be D or N; $X_7$ can be N, S, or I; $X_8$ can be K or R; $X_9$ can be T or A; $X_{10}$ can be M or V.

SEQ ID NO: 24: HC-FR4
WGQGT$X_1$VTVSS; wherein $X_1$ can be L or T

SEQ ID NO: 25: LC-FR1
DI$X_1$MTQSP$X_2$SL$X_3X_4$S$X_5$G$X_6X_7X_8$TI$X_9$C; wherein $X_1$ can be V, Q; $X_2$ can be S. D; $X_3$ can be A, S; $X_4$ can be V, A; $X_5$ can be A, L, V; $X_6$ can be E, D; $X_7$ can be T, R; $X_8$ can be V, A; $X_9$ can be N, T.

SEQ ID NO: 26: LC-FR2
WYQQKPGQ$X_1$PKLLIY; $X_1$ can be S or P.

SEQ ID NO: 27: LC-FR3
GVP$X_1$RF$X_2$GSG$X_3$GTDFTLTISS$X_4$Q$X_5$ED$X_6$A$X_7$YYC; $X_1$ can be D, S; $X_2$ can be I, S, or T; $X_3$ can be S or A; $X_4$ can be V or L; $X_5$ can be A, P; $X_6$ can be L, V, or F; $X_7$ can be I, V, or T.

SEQ ID NO: 28: LC-FR4
GGGTK$X_1$E$X_2$K; wherein $X_1$ can be L or V; and $X_2$ can be L or I.

SEQ ID NO: 29: Chimeric antibody CLS-A1HC0LC0 heavy chain sequence
AVQLVESGGGLVQPKESLKISCAASGFTFSNAVMNWVRQAPGKGLEWVARIRTKPNNYATFYA

DSVKGRFTFSRDDSKSMVYLQMDNLKTEDTAMYYCTAWTTEGIYWGQGTLVTVS

SEQ ID NO: 30: Chimeric antibody CLS-A1HC0LC0 light chain sequence
DIVMTQSPSSLAVSAGFTVTINCKSSQSLLYSGNQKNYLAWYQQKPGQSPKLLIYWASTRQSGV

PDRFIGSGSGTDFTLTISSVQAEDLAIYYCQQYYDTPWTFGGGTKLELK

SEQ ID NO: 31: mouse CXCL16 sequence
MRRGFGPLSLAFFLFLLALLTLPGDGNQGSVAGSCSCDRTISSGTQIPQGTLDHIRKYLKAFHRCP

FFIRFQLQSKSVCGGSQDQWVRELVDCFERKECGTGHGKSFHHQKHLPQASTQTPEAAEGTPSD

TSTPAHSQSTQHSTLPSGALSLNKEHTQPWEMTTLPSGYGLEARPEAEANEKQQDDRQQEAPGA

GASTPAWVPVLSLLAIVFFLTAAMAYVLCNRRATQQNSAGLQLWYTPVEPRP

SEQ ID NO: 32 The amino acid sequence of the heavy chain of the chimeric antibody (HC0)
ACCMGWTLVFLFLLSVTAGVHSAVQLVESGGGLVQPKESLKISCAASGFTFSNAVMNWVRQAP

GKGLEWVARIRTKPNNYATFYADSVKGRFTFSRDDSKSMVYLQMDNLKTEDTAMYYCTAWTT

EGIYWGQGTLVTVSSAETTAPSVYPLAPGTALKSNSMVTLGCLVKGYFPEPVTVTWNSGALSSG

VHTFPAVLQSGLYTLTSSVTVPSSTWSSQAVTCNVAHPASSTKVDKKIVPRECNPCGCTGSEVSS

VFIFPPKTKDVLTITLTPKVTCVVVDISQNDPEVRFSWFIDDVEVHTAQTHAPEKQSNSTLRSVSE

LPIVHRDWLNGKTFKCKVNSGAFPAPIEKSISKPEGTPRGPQVYTMAPPKEEMTQSQVSITCMVK

GFYPPDIYTEWKMNGQPQENYKNTPPTMDTDGSYFLYSKLNVKKETWQQGNTFTCSVLHEGLH

NHHTEKSLSHSPGK

SEQ ID NO: 33: The Optimized coding sequence (for *Cricetulus griseus* (CHO)) of the heavy chain of the chimeric antibody (HC0)
ACCATGGGCTGGACCCTGGTGTTCCTGTTCCTGCTAAGCGTGACGGCGGGCGTCCACTCCGC

TGTGCAACTCGTGGAGAGCGGCGGCGGCCTGGTGCAGCCTAAGGAGAGCCTGAAGATCAGC

TGCGCCGCTAGCGGCTTCACATTCAGCAACGCCGTGATGAACTGGGTGAGACAAGCCCCTGG

CAAGGGCCTGGAGTGGGTGGCTAGAATCAGAACCAAGCCTAACAACTACGCCACCTTCTAC

GCCGACAGCGTGAAGGGCAGATTTACGTTCAGCAGAGATGACAGCAAGAGCATGGTGTACC

TGCAGATGGACAACCTGAAGACCGAGGACACCGCCATGTACTACTGCACCGCCTGGACCAC

CGAGGGCATCTACTGGGGCCAAGGCACCCTGGTGACCGTGAGCAGCGCCGAGACCACCGCC

CCTAGCGTGTACCCTCTGGCCCCTGGCACCGCCCTGAAAAGCAATAGCATGGTGACCCTGGG

CTGCCTTGTGAAGGGCTATTTCCCTGAGCCTGTGACCGTGACCTGGAACTCCGGCGCCCTGA

-continued

GCAGCGGCGTGCACACCTTCCCTGCCGTGCTGCAGAGCGGCCTGTACACCCTGACAAGCAGC

GTGACCGTGCCTAGCAGCACCTGGAGCAGCCAAGCCGTGACCTGCAACGTGGCCCACCCTG

CTAGCAGCACCAAGGTGGACAAGAAGATCGTGCCTAGAGAGTGCAACCCTTGCGGCTGCAC

CGGCAGCGAGGTGAGCAGCGTGTTCATCTTCCCTCCTAAGACCAAGGACGTGCTGACCATCA

CCCTGACCCCTAAGGTGACCTGCGTGGTGGTGGACATCTCTCAGAACGACCCTGAGGTGAGA

TTCAGCTGGTTCATCGACGACGTGGAGGTGCACACCGCTCAGACCCACGCCCCTGAGAAGCA

AAGCAACAGCACCCTTAGAAGCGTGAGCGAGCTGCCTATCGTGCACAGAGACTGGCTGAAC

GGCAAGACCTTCAAGTGCAAGGTGAACAGCGGCGCCTTCCCTGCCCCTATCGAGAAGAGCA

TCAGCAAGCCTGAGGGCACCCCTAGAGGCCCTCAAGTGTACACCATGGCCCCTCCTAAGGA

GGAGATGACACAGAGCCAAGTGAGCATCACCTGCATGGTGAAAGGCTTCTACCCTCCTGAC

ATCTACACCGAGTGGAAGATGAACGGACAGCCTCAAGAGAACTACAAGAACACCCCTCCTA

CCATGGACACCGACGGCAGCTACTTCCTGTACAGCAAGCTGAACGTGAAGAAGGAGACCTG

GCAGCAAGGCAACACCTTCACCTGCAGCGTGCTGCACGAGGGCCTGCACAACCACCACACC

GAGAAGAGCCTGAGCCACAGCCCTGGCAAG

SEQ ID NO: 34: The amino acid sequence of the light chain of the chimeric antibody (LC0)
ACCMVSSAQFLGLLLLCFQGTRCDIVMTQSPSSLAVSAGFTVTINCKSSQSLLYSGNQKNYLAW

YQQKPGQSPKLLIYWASTRQSGVPDRFIGSGSGTDFTLTISSVQAEDLAIYYCQQYYDTPWTFGG

GTKLELKRADAAPTVSIFPPSTEQLATGGASVVCLMNNFYPRDISVKWKIDGTERRDGVLDSVTD

QDSKDSTYSMSSTLSLTKADYESHNLYTCEVVHKTSSSPVVKSFNRNEC

SEQ ID NO: 35: The Optimized coding sequence (for *Cricetulus griseus* (CHO)) sequence of the light chain of the chimeric antibody_LC (LC0)
ACCATGGTGAGCAGCGCTCAGTTCCTGGGCCTGCTGCTGCTGTGCTTCCAAGGCACAAGATG

CGACATCGTGATGACACAGAGCCCTAGCAGCCTGGCCGTGAGCGCCGGCGAGACCGTGACC

ATCAACTGCAAGAGCTCTCAGAGCCTGCTGTACAGCGGCAATCAGAAGAACTACCTGGCCT

GGTATCAGCAGAAGCCTGGACAGAGCCCTAAGCTGCTGATCTACTGGGCTAGCACAAGACA

GAGCGGCGTGCCTGACAGATTCATCGGCAGCGGCAGCGGCACCGACTTCACCCTGACCATC

AGCAGCGTGCAAGCCGAGGACCTGGCCATCTACTACTGTCAGCAGTACTACGACACCCCTTG

GACCTTCGGCGGCGGCACCAAGCTGGAGCTGAAGAGAGCCGACGCCGCCCCTACCGTGAGC

ATCTTCCCTCCTAGCACCGAGCAGCTGGCCACCGGCGGCGCTAGCGTGGTGTGCCTGATGAA

CAACTTCTACCCTAGAGACATCAGCGTGAAGTGGAAGATCGACGGCACCGAGAGAAGAGAC

GGCGTGCTGGACAGCGTGACCGACCAAGACAGCAAGGACAGCACCTACAGCATGAGCAGCA

CCCTGAGCCTGACCAAGGCCGACTACGAGAGCCACAACCTGTACACCTGCGAGGTGGTGCA

CAAGACAAGCAGCAGCCCTGTGGTGAAGAGCTTCAACAGAAACGAGTGC

SEQ ID NO: 36: The chimeric antibody HC0LC0 VH domain had the sequence
AVQLVESGGGLVQGPKESLKISCAASGFTFSNAVMNWVRGAPGKGLEWVARIRTKPNNYATFY

ADSVKGRFTFSRDDSKSMVYLQMDNLKTEDTAMYYCTAWTTEGIYWGQGTLVTVSS (SEQ ID

NO: 36) (The CDR residues are underlined).

SEQ ID NO: 37: The closest human germline gene V-region is *Homo sapiens* IGHV3-73*01
EVQLVESGGGLVQPGGSLKLSCAASGFTFSGSAMHWVRQGASGKGLEWVGRIRSKANSYATAY

AASVKGRFTISRDDSKNTAYLQMNSLKTEDTAVYYCTR

SEQ ID NO: 38: Heavy chain HC1
QVQLVESGGGVVQPGGSLRLSCAASGFTFSNAVMNWVRQAPGKGLEWVARIRTKPNNYATFY

ADSVKGRFTFSRDNSKTMLYLQMNSLRAEDTAVYYCTAWTTEGIYWGQGTLVTVSSASTKGPS

VFPLAPSSKSTSGGTAALGCLVKDYFPEPVTVSWNSGALTSGVHTFPAVLQSSGLYSLSSVVTVP

-continued

SSSLGTQTYICNVNHKPSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK

SEQ ID NO: 39: Heavy chain HC2
AVQLVESGGGLVQPGGSLKISCAASGFTFSNAVMNWVRQASGKGLEWVGRIRTKPNNYATFYA

DSVKGRFTISRDDSKNTAYLQMNSLKTEDTAMYYCTAWTTEGIYWGQGTLVTVSSASTKGPSV

FPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK

SEQ ID NO: 40: Heavy chain HC3
EVQLVESGGGLVQPGGSLKLSCAASGFTFSNAVMNWVRQAPGKGLEWVGRIRTKPNNYATFYA

DSVKGRFTFSRDDSKNTAYLQMNILKTEDTAMYYCTAWTTEGIYWGQGTTVTVSSASTKGPSV

FPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK

SEQ ID NO: 41: Heavy chain HC4
EVQLVESGGGLVKPGGSLRLSCAASGFTFSNAVMNWVRQAPGKGLEWVARIRTKPNNYATFYA

DSVKGRFTFSRDDSKNTLYLQMNSLKTEDTAVYYCTAWTTEGIYWGQGTTVTVSSASTKGPSVF

PLAPSSKSTSGGTAALGCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK

SEQ ID NO: 42: Heavy chain HC5
EVQLVESGGGLVQPGGSLKLSCAASGFTFSNAVMNWVRQASGKGLEWVARIRTKPNNYATFYA

DSVKGRFTFSRDDSKNTAYLQMNSLKTEDTAMYYCTAWTTEGIYWGQGTLVTVSSASTKGPSV

FPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK

SEQ ID NO: 43: Light chain LC1
DIVMTQSPDSLAVSAGFTVTINCKSSQSLLYSGNQKNYLAWYQQKPGQSPKLLIYWASTRQSGV

PDRFSGSGSGTDFTLTISSVQAEDVAVYYCQQYYDTPWTFGGGTKVEIKRTVAAPSVFIFPPSDEQ

LKSGTASVVCLLNNFYPREAKVQWKVDNALQSGNSQESVTEQDSKDSTYSLSSTLTLSKADYEK

HKVYACEVTHQGLSSPVTKSFNRGEC

-continued

SEQ ID NO: 44: Light chain LC2
DIVMTQSPSSLAVSLGFTATINCKSSQSLLYSGNQKNYLAWYQQKPGQPPKLLIYWASTRQSGVP

DRFTGSGAGTDFTLTISSVQAEDLAIYYCQQYYDTPWTFGGGTKVEIKRTVAAPSVFIFPPSDEQL

KSGTASVVCLLNNFYPREAKVQWKVDNALQSGNSQESVTEQDSKDSTYSLSSTLTLSKADYEKH

KVYACEVTHQGLSSPVTKSFNRGEC

SEQ ID NO: 45: Light chain LC3
DIQMTQSPSSLSASVGDRVTITCKSSQSLLYSGNQKNYLAWYQQKPGQSPKLLIYWASTRQSGVP

DRFSGSGSGTDFTLTISSLQAEDFATYYCQQYYDTPWTFGGGTKVEIKRTVAAPSVFIFPPSDEQL

KSGTASVVCLLNNFYPREAKVQWKVDNALQSGNSQESVTEQDSKDSTYSLSSTLTLSKADYEKH

KVYACEVTHQGLSSPVTKSFNRGEC

SEQ ID NO: 46: Light chain LC4
DIQMTQSPSSLSASVGDRVTITCKSSQSLLYSGNQKNYLAWYQQKPGQSPKLLIYWASTRQSGVP

SRFSGSGSGTDFTLTISSLQPEDLAIYYCQQYYDTPWTFGGGTKLELKRTVAAPSVFIFPPSDEQLK

SGTASVVCLLNNFYPREAKVQWKVDNALQSGNSQESVTEQDSKDSTYSLSSTLTLSKADYEKHK

VYACEVTHQGLSSPVTKSFNRGEC

SEQ ID NO: 47: Light chain LC5
DIVMTQSPSSLAVSAGERATINCKSSQSLLYSGNQKNYLAWYQQKPGQSPKLLIYWASTRQSGV

PDRFIGSGSGTDFTLTISSLQAEDVAIYYCQQYYDTPWTFGGGTKLELKRTVAAPSVFIFPPSDEQ

LKSGTASVVCLLNNFYPREAKVQWKVDNALQSGNSQESVTEQDSKDSTYSLSSTLTLSKADYEK

HKVYACEVTHQGLSSPVTKSFNRGEC

SEQ ID NO: 48: human IgG1 isotype constant domain
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSR

WQQGNVFSCSVMHEALHNHYTQKSLSLSPGK

SEQ ID NO: 49: human IgK isotype constant domain
RTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

EXAMPLES

Example 1. Binding of Huma CXCL16 to CXCL16

The binding characteristics of 25 CXCL16 antibodies were analyzed using the bio-light interferometry (ForteBio). All antibodies were diluted in freshly prepared running buffer. Antibodies were immobilized onto the surface of a series of biosensors using the capture methods at 0.3 μg/mL. Recombinant human CXCL16 (rhCXCL16) protein (100 nM) was passed over the surface to generate a binding response for 10 minutes. Binding data for the antibody and antigen interactions were collected at 25 °C on the biosensors. Then, the running buffer was passed for 10 minutes to dissociate them. The association constant ($k_a$) and the dissociation constant ($k_d$) were observed, and the equilibrium binding constant ($K_D$) was calculated. Of 25 antibodies made, 5 antibodies showed significant binding affinity ($K_D<1\times10^{-8}$ M). $R^2$: The value indicating how well the fit and experimental data correlate; $X^2$: The measure of error between the experimental data and fitted line.

To further characterize the binding affinity of selected 6 of CXCL16 antibodies, the protein-based ELISA was performed. The recombinant human CXCL16 antigen (976-CX, R&D systems, USA) was immobilized onto 96-well plates and incubated for 2 hours at room temperature. Non-specific binding sites were blocked by incubating with 1% BSA in PBS overnight at 4 °C Plates were then washed with PBS. Humanized CXCL16 antibodies at various concentrations (0.001~10 nM) were incubated with the immobilized antigen for 2 hours at room temperature. After the incubation, the plates were washed, incubated with HRP-labeled anti-human IgG antibody (W4031, Promega, USA) for 0.5 hours, and developed using the substrate solution (DY008B, R&D systems). The results are shown in FIG. 1A, indicates that the binding affinity of humanized antibodies, HC4LC1, HC5LC1, HC5LC2, HC5LC3, and HC5LC5, were significantly higher than a control IgG antibody.

Figure 1B:
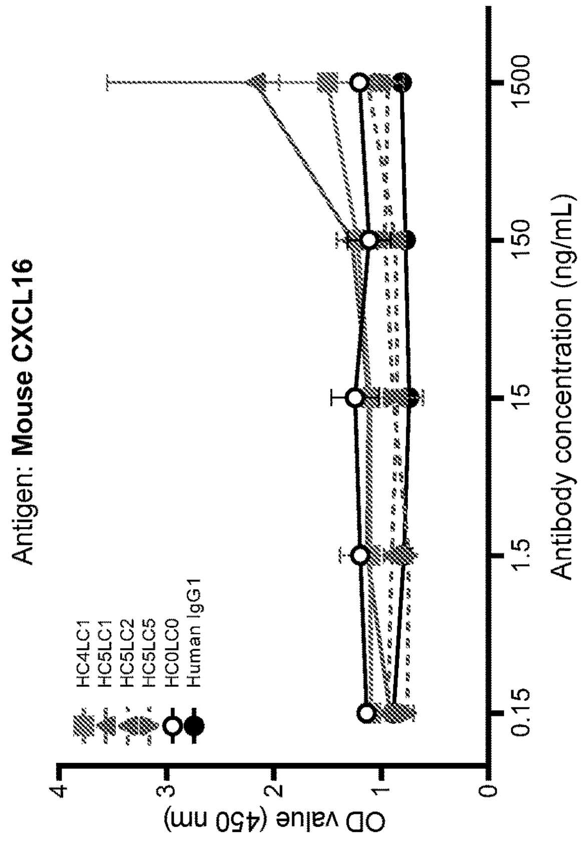

To evaluate the cross-reactivity with mouse CXCL16 antigen, the same ELISA experiment was performed with recombinant mouse CXCL16 antigen (503-CX, R&D systems). The mouse CXCL16 antigen was immobilized onto 96-well plates by incubation for 2 hours at room temperature. Non-specific binding sites were blocked by incubating with 1% BSA in PBS overnight at 4 °C. After coating, the plates were washed with PBS. Humanized CXCL16 antibodies at various concentration (0.001~10 nM) were incubated with the immobilized antigen for 2 hours at room temperature. After binding, the plates were washed, incubated with HRP-labeled anti-human IgG antibody (W4031, Promega, USA) for 0.5 hours, and developed using the substrate solution (DY008B, R&D systems). The results are shown in FIG. 1B. The binding affinity of humanized antibodies was similar to that of IgG antibody. The results indicate that humanized CXCL16 antibodies specifically bind to human CXCL16. See Table 6.

TABLE 6

Binding analysis of humanized CXCL16 antibody and CXCL16 antigen (ForteBio).

| Antibody | Capture Level (nm) | $k_a$ ($m^{-1}s^{-1}$) | $k_d$ ($s^{-1}$) | $K_D$ (M) | $R^2$ | $X^2$ | Res@ 3.7 nM |
|---|---|---|---|---|---|---|---|
| HC0LC0 | 0.79 | 2.72E−11 | <1.0E−07 | <1.0E−12 | 0.986 | 0.583 | 0.130 |
| HC1LC1 | ND | ND | ND | ND | ND | ND | ND |
| HC1LC2 | ND | ND | ND | ND | ND | ND | ND |
| HC1LC3 | ND | ND | ND | ND | ND | ND | ND |
| HC1LC4 | ND | ND | ND | ND | ND | ND | ND |
| HC1LC5 | ND | ND | ND | ND | ND | ND | ND |
| HC2LC1 | ND | ND | ND | ND | ND | ND | ND |
| HC2LC2 | ND | ND | ND | ND | ND | ND | ND |
| HC2LC3 | ND | ND | ND | ND | ND | ND | ND |
| HC2LC4 | ND | ND | ND | ND | ND | ND | ND |
| HC2LC5 | ND | ND | ND | ND | ND | ND | ND |
| HC3LC1 | ND | ND | ND | ND | ND | ND | ND |
| HC3LC2 | ND | ND | ND | ND | ND | ND | ND |
| HC3LC3 | ND | ND | ND | ND | ND | ND | ND |
| HC3LC4 | ND | ND | ND | ND | ND | ND | ND |
| HC3LC5 | ND | ND | ND | ND | ND | ND | ND |
| HC4LC1 | 0.82 | 1.74E+04 | 1.90E−05 | 1.09E−09 | 0.995 | 0.184 | 0.113 |
| HC4LC2 | ND | ND | ND | ND | ND | ND | ND |
| HC4LC3 | ND | ND | ND | ND | ND | ND | ND |
| HC4LC4 | ND | ND | ND | ND | ND | ND | ND |
| HC4LC5 | ND | ND | ND | ND | ND | ND | ND |
| HC5LC1 | 0.74 | 1.83E+04 | 5.97E−05 | 3.26E−09 | 0.996 | 0.079 | 0.080 |
| HC5LC2 | 0.7 | 2.43E+04 | 6.07E−05 | 2.50E−09 | 0.997 | 0.170 | 0.152 |
| HCSLC3 | 0.55 | 2.64E+04 | 6.35E−04 | 1.44E−09 | 0.994 | 0.114 | 0.078 |
| HC5LC4 | ND | ND | ND | ND | ND | ND | ND |
| HC5LC5 | 0.88 | 1.82E+04 | <1.0E−07 | <1.0E−12 | 0.997 | 0.419 | 0.231 |

Note:
HC0LC0 is a chimeric antibody that binds to human CXCL16; see relevant disclosure in Example 7. ND refers to that the signal was not detectable. "Res@3.7 nM" means resolution at 3.7 nM.

Figure 2A:
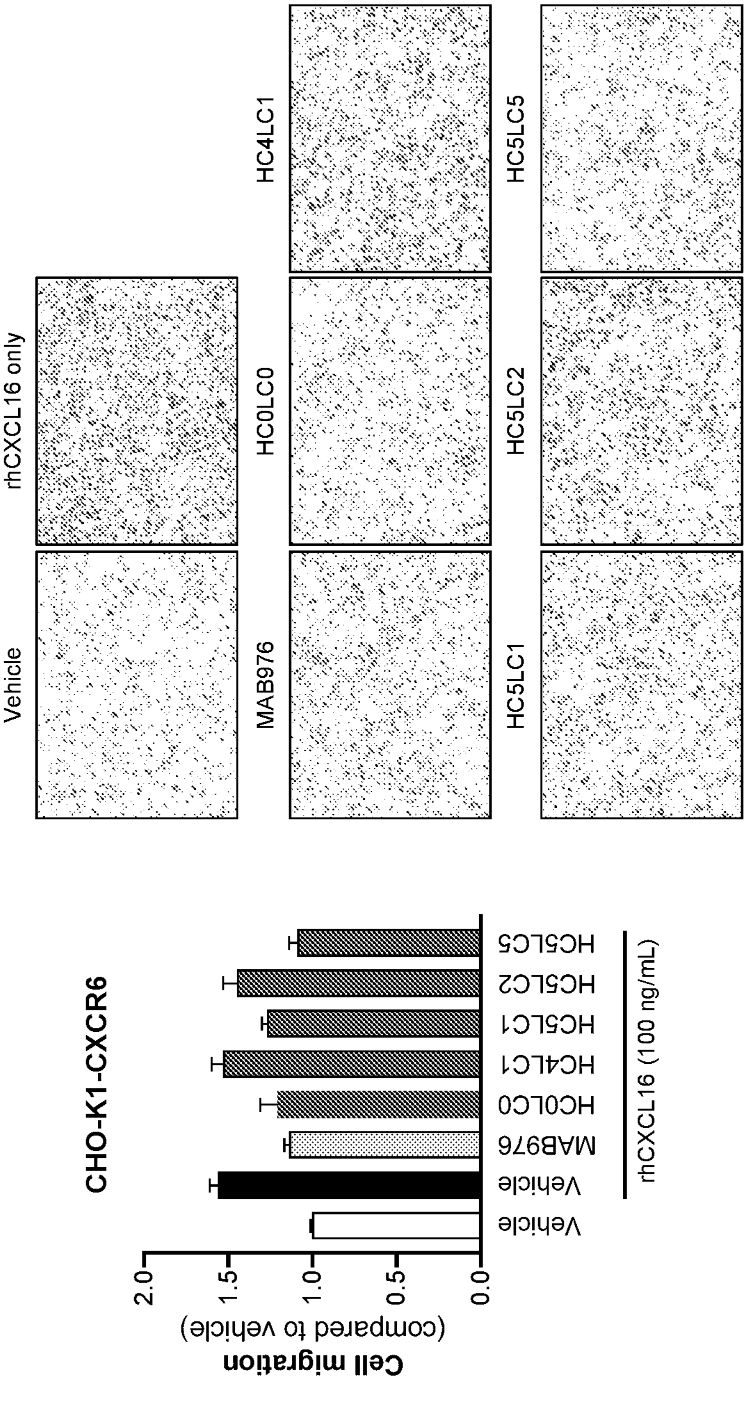
FIGS. 2A, 2B, 2C, and 2D show the results of the effect of humanized CXCL16 antibodies (HC4LC1. HC5LC1, HC5LC2, and HC5LC5) on cancer cell chemotaxis and migration analysis. The ability of humanized CXCL16 antibodies to inhibit cancer cell chemotaxis and migration were assessed in several cell lines; CXCR6-overexpressed CHO-K1 cells (FIG. 2A), Thyroid cancer cell line BHP10-3M (FIG. 2B), breast cancer cell line MDA-MB-231 (FIG. 2C), and monocyte cell line THP-1 (FIG. 2D).

Example 2 Functional Assays a. Inhibition of Cancer Cell Chemotaxis and Migration CXCR6 is a receptor for chemokine CXCL16 and cells harboring CXCR6 migrate in response to CXCL16. Therefore, to evaluate the activity of CXCL16 antibody in inhibiting cell migration induced by CXCL16 and CXCR6 interaction, transwell migration assays were performed. A polycarbonate membrane with a pore size of 8 μm (Corning, NY, USA) was pre-coated with gelatin, and the membrane was placed into a 24-well plate. The membrane separated each well into an upper chamber and a lower chamber. The upper chamber was plated with CXCR6-overexpressed CHO-K1 cells. The lower chamber was filled with media containing 100 ng/mL rhCXCL16. After 4-5 h, the lower chamber was stained with 1% crystal violet solutions and the numbers of migrated cells on the lower chamber were counted. The results show that humanized CXCL16 antibodies HC4LC1, HC5LC1, HC5LC2, HC5LC3, and HC5LC5 inhibited the migration of CXCR6-overexpressed CHO-K1 cell from upper chamber to the lower chamber. The results show treatment of rhCXCL16 increased cell migration into the lower chamber of CXCR6-overexpressed CHO-K1 cells, while treatment of the humanized CXCL16 antibodies decreased the migration. See FIG. 2A.

To evaluate that blockage of CXCL16 could lead to inhibit cancer cell migration, transwell migration assay was performed. For assay, 8 μm pore-size polycarbonate membrane (Corning, NY, USA) was used. A polycarbonate membrane with a pore size of 8 μm (Corning, NY, USA) was pre-coated with gelatin, and the membrane was placed into a 24-well plate. The membrane separated each well into an upper chamber and a lower chamber. CXCL16 antibody (at 10-100 μg/mL) was preincubated in the upper and lower chamber for 0.5 hours. The upper and lower chamber were plated with thyroid cancer cell BHP10-3M ($1\times10^5$/100 μL) and co-culture conditioned medium (0.5× co-CM), respectively.

Figure 2B:
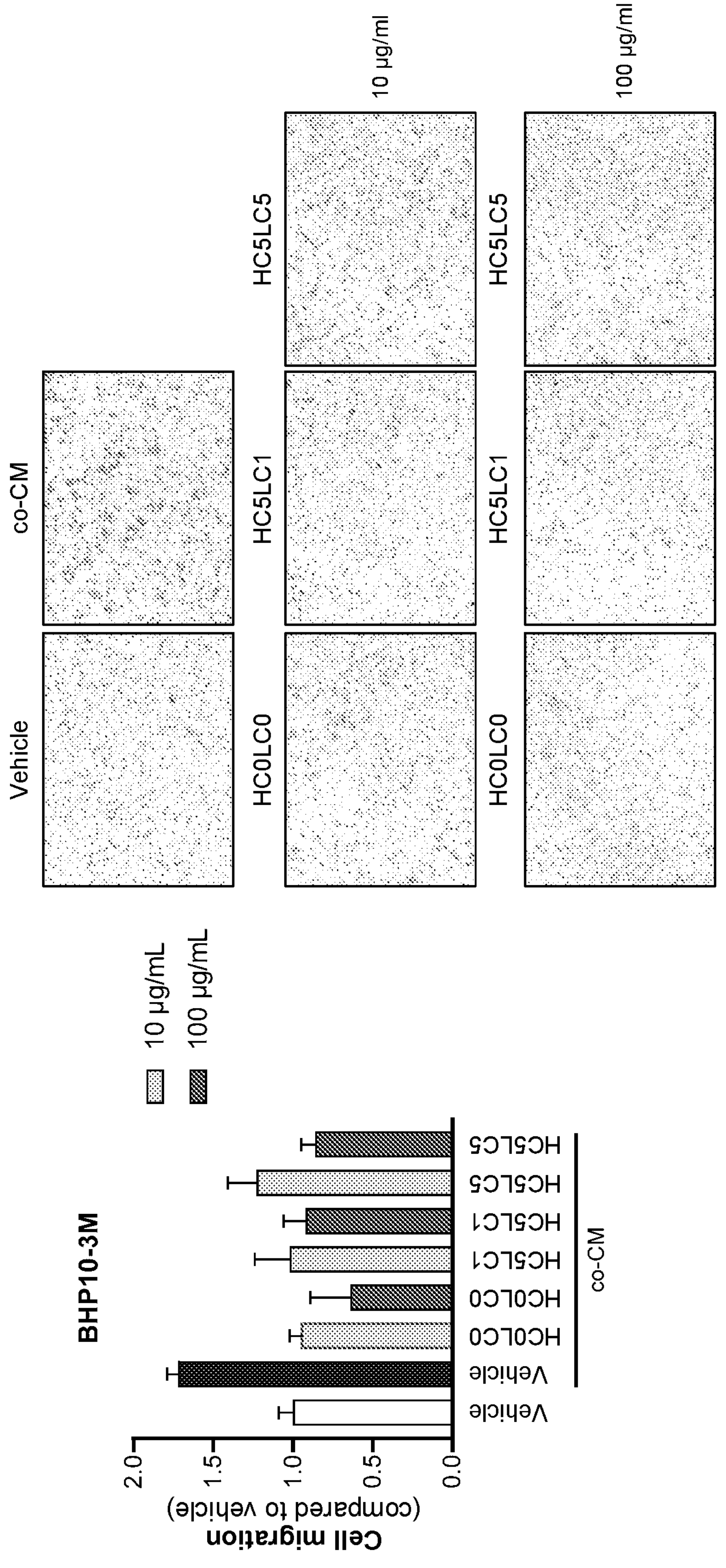

The co-CM is the conditioned medium obtained from co-culture of BHP 10-3M and THP-1 cells. The BHP10-3M cells were seeded on 100 mm culture dishes with $3\times10^6$ cells in 10 ml of RPMI1640 medium. After 24 hours incubation, THP-1 cells were seeded additionally with $6\times10^6$ cells. After then, 10 μL of 5 mM PMA stock solution (V1171, Promega) to 10 mL of RPMI medium to make 5 μM PMA. It induced the macrophage differentiation. After 24 hours incubation, the conditioned medium obtained from the co-culture of thyroid cancer cells and macrophages (co-CM) were collected, and it was rich in CXCL16. After 6 hours of incubation of thyroid cancer cells in the upper chamber and co-CM in the lower chamber, the lower chamber was stained with 1% crystal violet solutions and the numbers of migrated cells were counted. Co-CM increased cell migration into the lower chamber of BHP10-3M cells, and humanized CXCL16 antibodies HC4LC1, HC5LC1, HC5LC2, HC5LC3, and HC5LC5 decreased the migration. Sec FIG. 2B.

To evaluate that blockage of CXCL16 could lead to inhibit cancer cell migration, transwell migration assay was performed. For assay, 8 μm pore-size polycarbonate membrane (Corning, NY. USA) was used. Membrane was pre-coated with gelatin, and the inserts were placed into a 24-well plate. CXCL16 antibody at 10-100 μg/mL was preincubated in the upper and lower chamber for 30 minutes. The upper and lower chamber were plated with breast cancer cell MDA-MB-231 ($1\times10^5$/100 μL) and co-culture conditioned medium (0.5× co-CM), respectively.

Figure 2C:
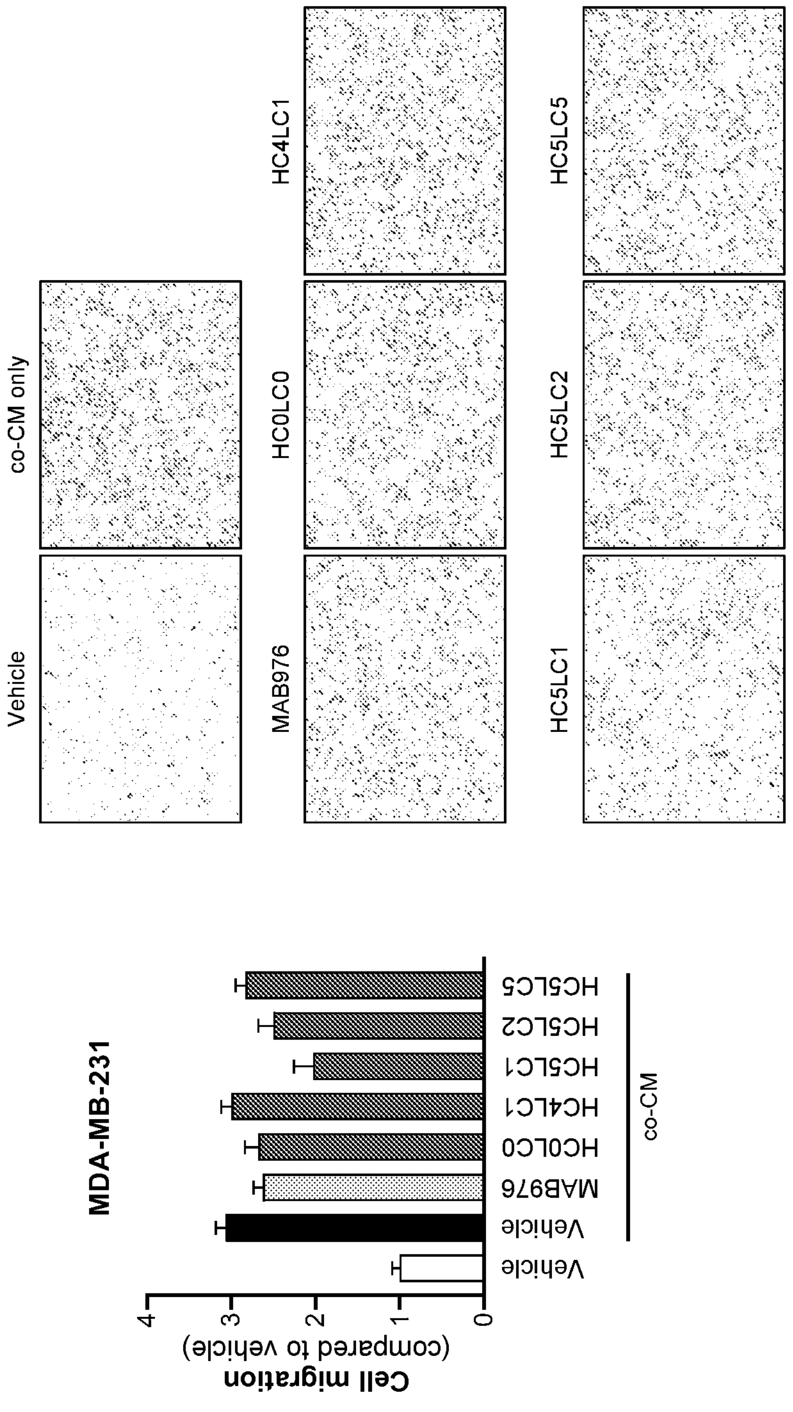

The co-CM is the conditioned medium obtained from co-culture of MDA-MB-231 and THP-1 cells. The BHP10-3M cells were seeded on 100 mm culture dishes with $3\times10^6$ cell in 10 ml of RPMI1640 medium. After 24 hours incubation, THP-1 cells were seeded additionally with $6\times10^6$ cells. After then, 10 μL of 5 mM PMA stock solution (V1171, Promega) to 10 mL of RPMI medium to make 5 μM PMA. It induced the macrophage differentiation. After 24 hours incubation, the conditioned medium obtained from the co-culture of thyroid cancer cells and macrophages (co-CM) were collected, and it was rich in CXCL16. After 6 hours of incubation of breast cancer cells in the upper chamber and co-CM in the lower chamber, the lower chamber was stained with 1% crystal violet solutions and the numbers of migrated cells were counted. Co-CM increased cell migration into the lower chamber of MDA-MB-231 cells, and humanized CXCL16 antibodies decreased it. See FIG. 2C.

Figure 2D:
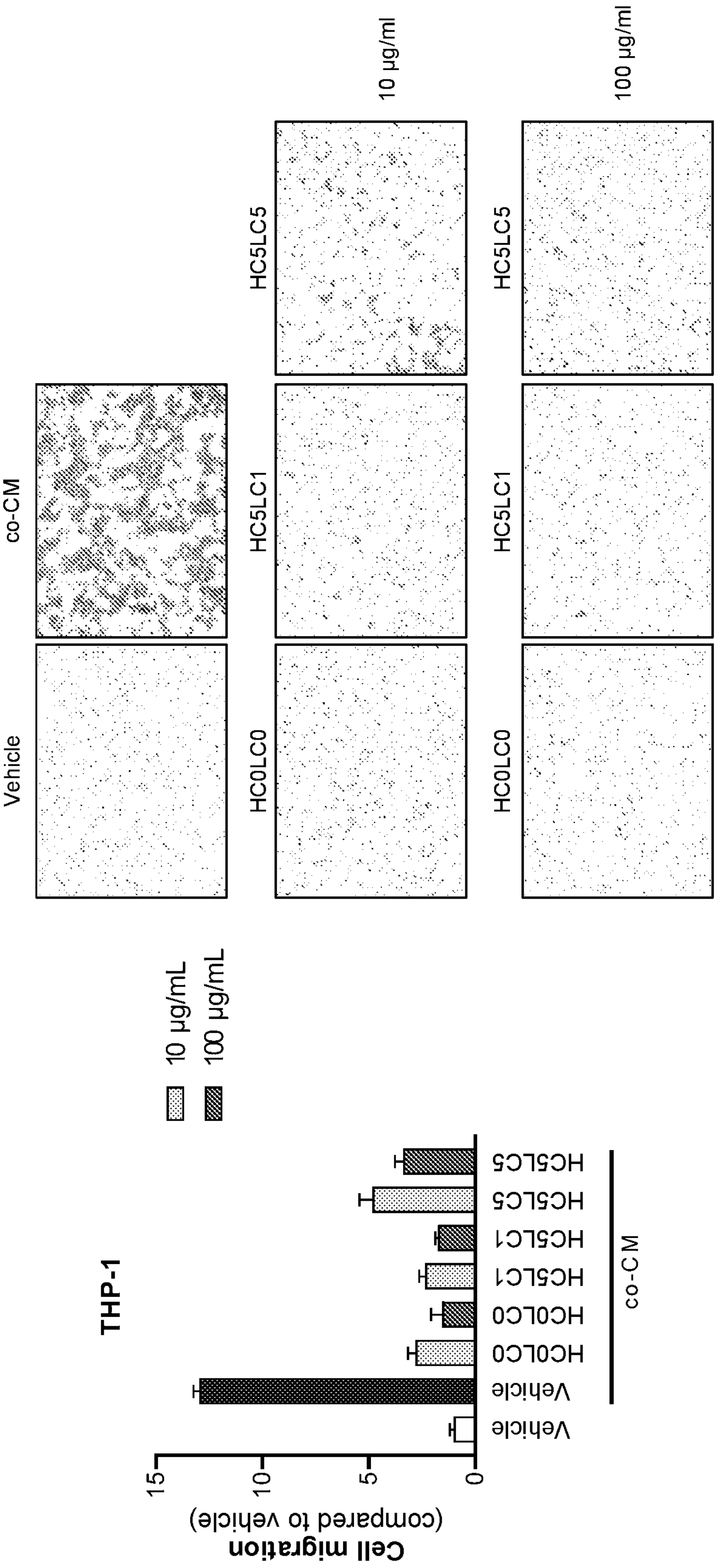
Figure 3A:
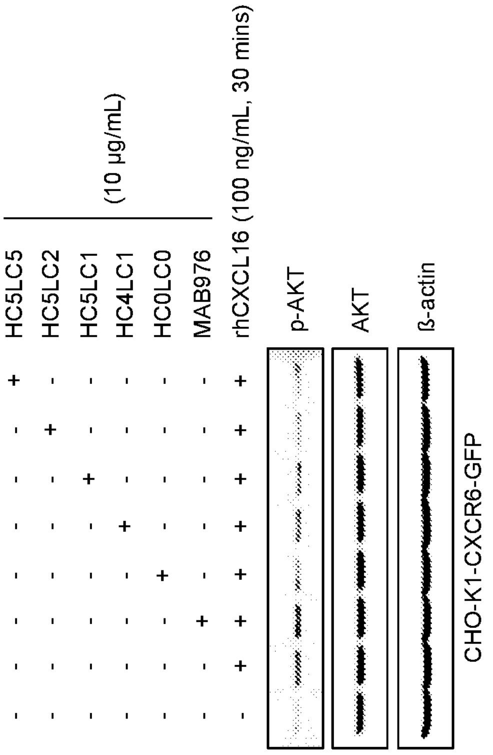
FIGS. 3A, 3B, 3C, and 3D show the results of effects of humanized CXCL16 antibodies (HC4LC1, HC5LC1, HC5LC2, and HC5LC5) on Akt activation. The ability of humanized CXCL16 antibodies in to inhibit CL16-induced Akt activation in cancer cells were assessed in several cell lines: CXCR6-overexpressed CHO-K1 cells (FIG. 3A), Thyroid cancer cell line BHP10-3M (FIG. 3B), breast cancer cell line MDA-MB-157 (FIG. 3C), and prostate cancer cell line PC3 (FIG. 3D).
Figure 3B:
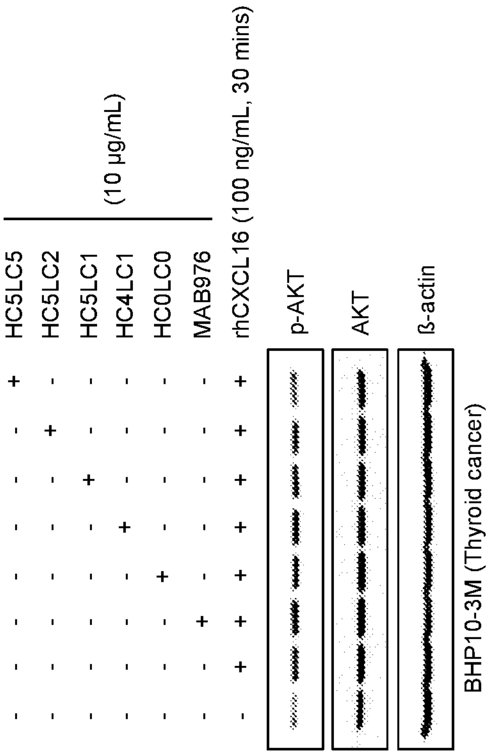
Figure 3C:
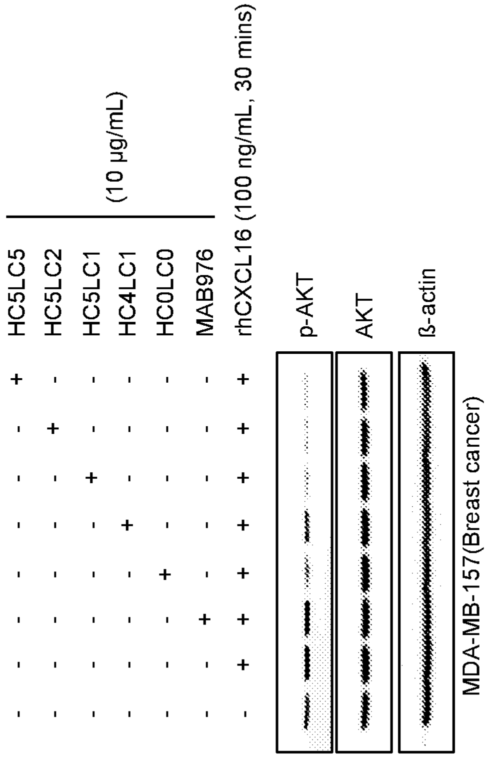
Figure 3D:
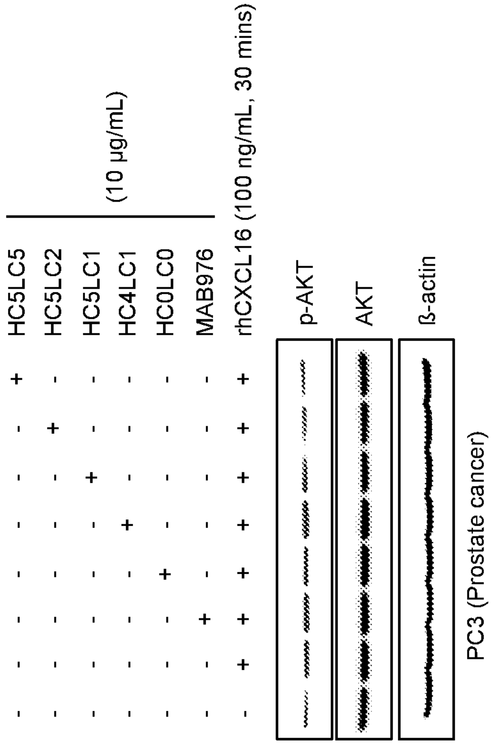

To evaluate that blockage of CXCL16 could lead to inhibit monocyte/macrophage migration, transwell migration assay was performed. For assay, 5 μm pore-size polycarbonate membrane (Corning, NY, USA) was used. Membrane was pre-coated with gelatin, and the inserts were placed into a 24-well plate. Humanized CXCL16 antibody at 10-100 μg/mL was preincubated in the upper and lower chamber for 30 minutes. The upper and lower chamber were plated with monocyte cell THP-1 and co-culture conditioned medium. After 4 h, the lower chamber was stained with 1% crystal violet solutions and the numbers of migrated cells were counted. Co-CM increased cell migration into the lower chamber of THP-1 cells, and humanized CXCL16 antibodies decreased it. The results suggested that humanized CXCL16 antibodies inhibit cell migration induced by CXCL16 and CXCR6 interaction. Humanized CXCL16 antibodies inhibit cancer cell migration, including thyroid and breast cancer cells Inhibition of cancer cell migration by humanized CXCL16 antibodies indicated an anti-cancer effect. See FIG. 2D.

b. Activation of Intracellular Akt Signaling Pathway, and CXCL16-Akt Signaling Mediates Cell Migration The CXCL16-CXCR6 interaction activates intracellular Akt signaling pathway, which promote cell migration. This experiment was designed to evaluate the ability of CXCL16 antibodies in blocking the Akt signaling induced by the CXCL16-CXCR6 interaction. Cancer cells were treated with 100 ng/ml of rhCXCL16 (976-CX, R&D systems) for 30 minutes in the presence of 10 μg/mL of humanized CXCL16 antibody (HC4LC1, HC5LC1. HC5LC2. HC5LC3, or HC5LC5) or control antibody (MAB976. R&D Systems, Minneapolis, MN). Cell lysates were harvested. Anti-pAkt (dilution ratio 1:1000, #9102; Cell Signaling), anti-Akt (dilution ratio 1:1000, #4370; Cell Signaling), and anti-β actin antibodies (dilution ratio 1:10,000, STJ91464, St John's laboratory, UK) were used. The results show that rhCXCL16 activates Akt phosphorylation in various cancer cells, including thyroid (FIG. 3B), breast (FIG. 3C), and prostate cancer cells (FIG. 3D), while the CXCL16 antibodies, HC4LC1, HCSLC1. HCSLC2. HC5LC3, and HC5LC5, abrogate the Akt phosphorylation.

c. Inhibition of Cell Migration in an In Vitro Model of Bone Metastasis

Figure 8A:
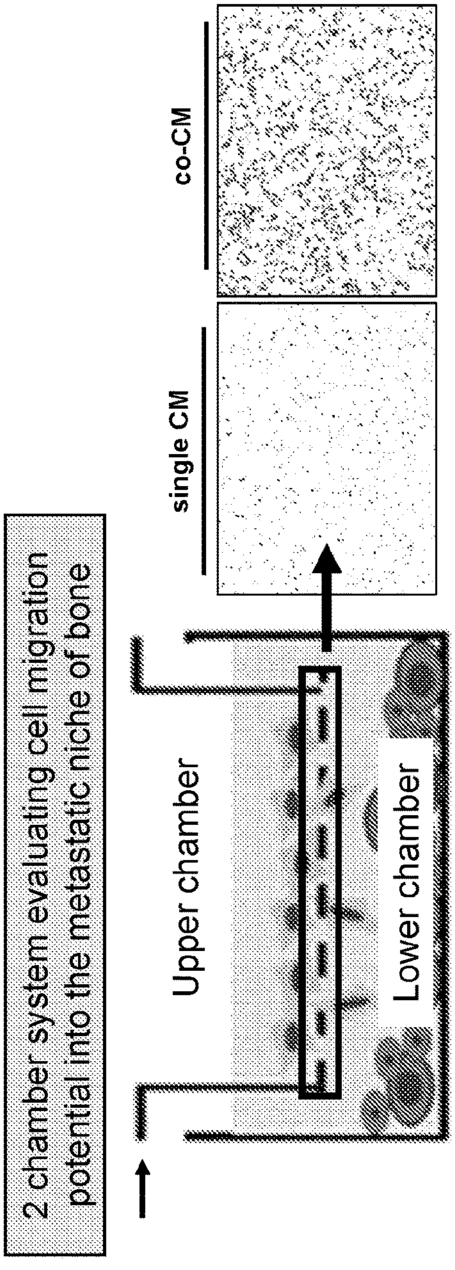
FIG. 8A illustrates a two-chamber system that resembles metastatic niche of bone.

A two-chamber system was set up to resemble the metastatic niche of bone. A lower chamber contains a conditioned medium (CM) of cancer cells/whole marrow cell co-cultures (called co-CM), which is CXCL16 enriched. CM from cancer cell cultures alone is used for control, referred to as single-CM. Single-CM contains negligible concentrations of CXCL16. An upper chamber (using insert) harboring cells that can be recruited into the metastatic chambers. Human CD11b+ bone marrow myeloid cells were treated with the CXCL16 antibodies for one hour, and the treated cells were added to upper chamber. After 4 hr, the insert (aka. the upper chamber) was harvested and cells in the insert were stained and the ability of the CXCL16 antibody in inhibiting cell recruitment into the metastatic niche were assessed. As shown in FIGS. 8A and 8B, co-CM (high conc. of sCXCL16) showed enhanced cell migration potential relative to the single-CM group.

d. Inhibition of Tumor Growth in an Orthotropic Xenograft Model, Alone or in Combination with Paclitaxel (PTX)

Figure 4A:
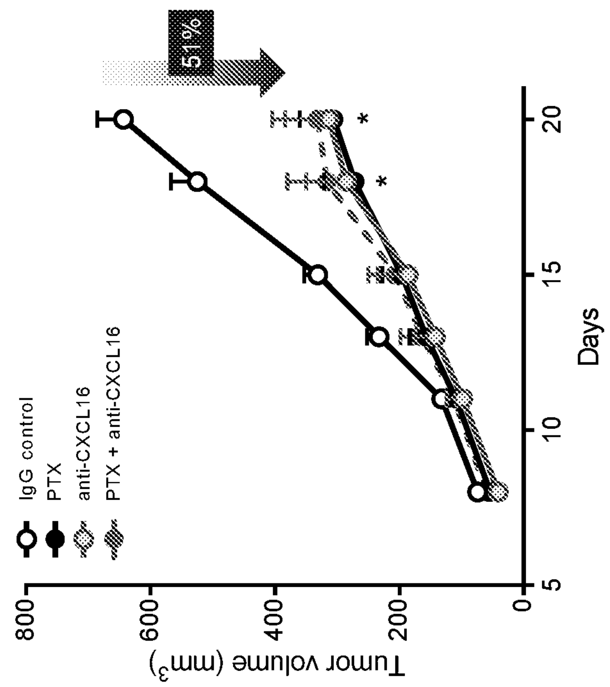
FIGS. 4A and 4B shows the results of tumor growth (FIG. 4A) or tumor weight (FIG. 4B) in mice carrying tumors derived from the triple-negative breast cancer cell line MDA-MB-231. These mice were treated with either anti-mouse CXCL16 antibody alone or anti-mouse CXCL16 antibody in combination with paclitaxel (PTX). The results show that anti-mouse CXCL16 antibody significantly reduced tumor volume and weight in a breast cancer mouse model.
Figure 4B:
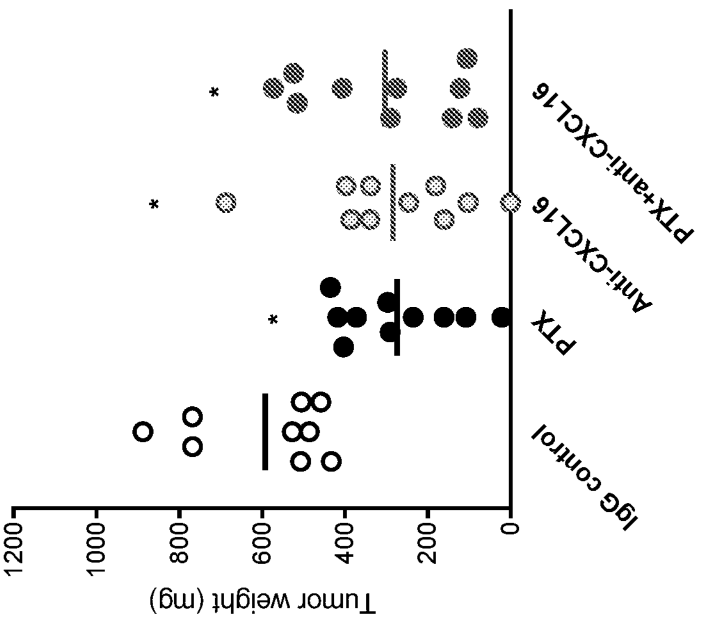

This example shows the humanized CXCL16 inhibits tumor growth in orthotropic xenograft model, alone or in combination with paclitaxel (PTX). To generate a breast cancer mouse model, the triple negative breast cancer cell line MDA-MB-231 ($6.5\times10^5$ cells) were transplanted into the back of BALB/c nude mice lacking T cells. The anticancer drugs were administered to each experimental group from the 5th day after cell transplantation. The "IgG Control" group received IgG antibody. IgG antibody (MAB006, R&D system), was administered intravenously at 50 mcg/20 g/day 3 times a week. The "PTX" group received paclitaxel. Paclitaxel (S1150, Selleckchem) was administered intraperitoneally at 10 mg/kg/mouse once a week. The "anti-CXCL16" group received an anti-CXCL16 antibody. An anti-mouse CXCL16 antibody (MAB503, R&D Systems, Minneapolis, MN) was administered intravenously at 50 mcg/20 g/day three times a week. The "PTX+anti-CXCL16" group received both paclitaxel and anti-CXCL16 antibody. Tumor size was measured on day 7, 11, 13, 15, 18, and 20. We measured tumor size with a caliper and calculated tumor volume by using the following equation; volume=½×a×b2, where a=long tumor diameter and b=short tumor diameter. Mice were sacrificed on day 20, tumor was removed, and the tumor weight was measured. The results show that the mouse CXCL16 antibody significantly reduced tumor volume and weight in the mouse tumor model. The reduction in tumor volume and weight in the CXCL16 group was comparable to those in the PTX group. It suggests that humanized CXCL16 antibodies may inhibit tumor growth and have an anti-cancer effect in vivo. See FIG. 4A and FIG. 4B.

Example 3. Combination Effect with Targeted Anticancer Agent for Thyroid Cancer Mouse Model $2\times10^6$ cells of the anaplastic thyroid cancer cell line FRO were injected into the back of nu/nu mice lacking T cells, and anticancer drugs were administered to each experimental group from the 5th day when the tumor was formed. The control group did not receive anticancer drugs, and to experimental group 1, lenvatinib (LENVIMA®), an anti- VEGF targeted anticancer drug, was orally administered at 30 mg/kg/day five times a week, and lenvatinib was administered to experimental group 2 and anti-CXCL16 therapeutic antibody were administered intraperitoneally at 100 meg/20 g/day twice a week. We measured tumor size with a caliper and calculated tumor volume using the following equation: volume=½× a×b2, where a=long tumor diameter and b=short tumor diameter.

Figure 5:
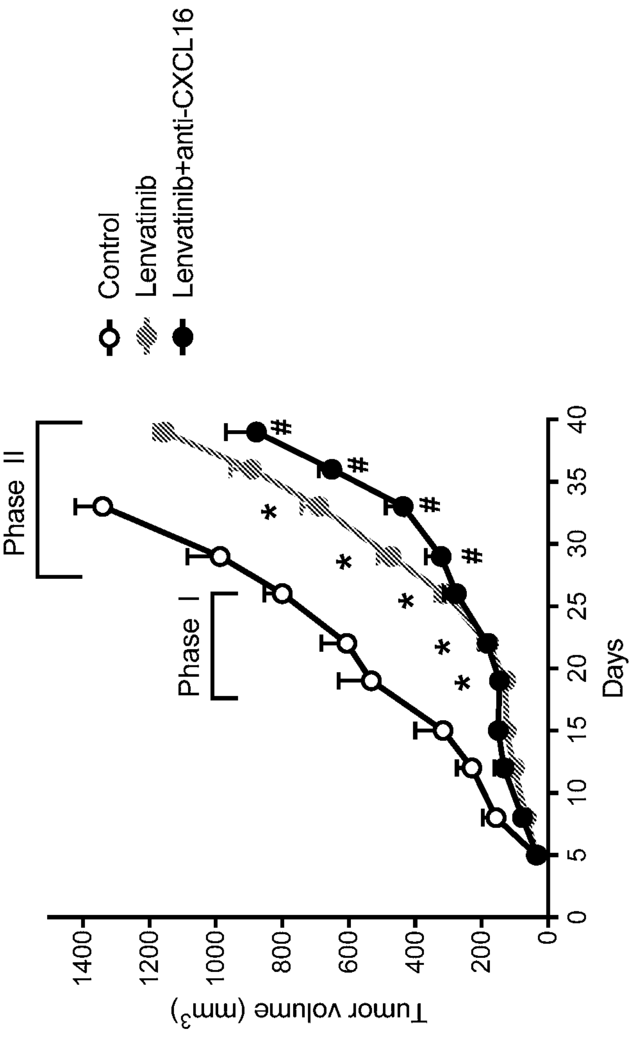
FIG. 5 shows tumor growth in mice carrying thyroid cancer treated by a combination therapy of Lenvatinib (targeted anticancer agent) and the anti-mouse CXCL16 antibody. The results show that the combination therapy of Lenvatinib and anti-mouse CXCL16 antibody significantly reduced tumor volume in a thyroid cancer mouse model.

As shown in FIG. 5, in phase 1 (up to day 22), in which the therapeutic effect of lenvatinib was maintained, the tumor growth rates of experimental group 1 and experimental group 2 were similar. Still, the therapeutic effect of lenvatinib was lowered, so the rate was the same as that of the control group. In phase 2 (after 22 days), the period when tumors start to grow again, the growth rate of the tumor was significantly reduced in Experimental Group 2, the group that was administered with the CXCL16 therapeutic antibody (anti-CXCL16), compared to Experimental Group 1, indicating the synergistic effect of the combination treatment.

Example 4. Combination Effect with Targeted Anticancer Agent and/or PD-L1 Inhibitor for Thyroid Cancer Mouse Model $5\times10^6$ cells of the anaplastic thyroid cancer cell line TBP3743 were injected into the back of C57Bl/6 mice, and anticancer drugs were administered to each experimental group from the 5th day when the tumor was formed. No anticancer drug was administered to the control group. The targeted anticancer drug lenvatinib was orally administered at 30 mg/kg to experimental Group One 5 times a week, lenvatinib oral administration and an anti-mouse CXCL16 antibody were injected at 100 mcg/20 g/day to experimental group 2 twice a week, and lenvatinib was administered to experimental group 3 Oral administration of lenvatinib and injection of a peptide PD-L1 inhibitor (as described in KR-20190072466-A, the entire disclosure of which is herein incorporated by reference) 5 times a week, oral administration of lenvatinib in experimental group 4, injection of a PD-L1 inhibitor (peptide) 5 times a week, and injection of anti-CXCL16 therapeutic antibody twice a week were used together.

Figure 6:
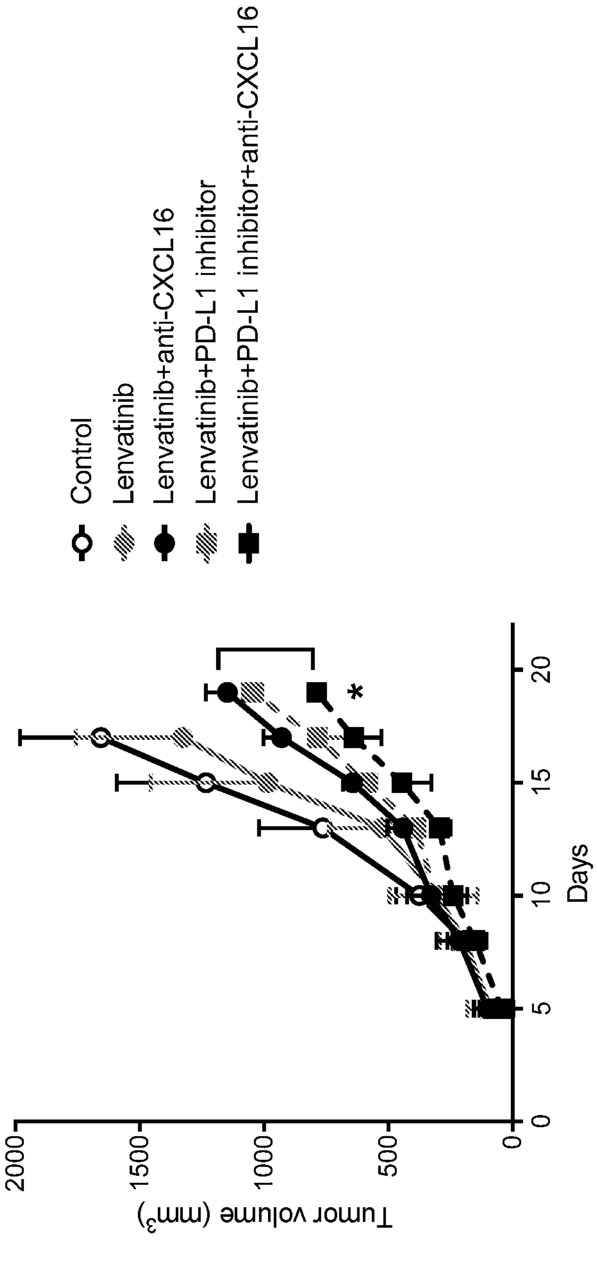
FIG. 6 shows the tumor growth in mice carrying thyroid cancer treated by a combination therapy of Lenvatinib (targeted anticancer agent), a PD-L1 inhibitor (immune checkpoint inhibitor), and an anti-mouse CXCL16 antibody.

From the $15^{th}$ day of the experiment, compared to lenvatinib alone (experimental group 1), lenvatinib+anti-CXCL16 therapeutic antibody (experimental group 2), or lenvatinib+PD-L1 inhibitor (experimental group 3)), the treatment effect was better in the combination administration group. On the 19th day of the experiment, it was confirmed that the three-agent therapy group of lenvatinib+PD-L1 inhibitor+anti-CXCL16 therapeutic antibody (experimental group 4) showed the best therapeutic effect. See FIG. 6.

Example 5. Combination Effect with Targeted Anticancer Agent and/or PD-L1 Inhibitor for Breast Cancer Mouse Model $2\times10^6$ pieces of 4T1, a breast cancer cell line, were injected into the back of C3H mice, and anticancer drugs were administered to each experimental group from the 5th day when the tumor was formed. No anticancer agent was administered to the control group, the targeted anticancer drug paclitaxel (Taxol) was administered intraperitoneally at 10 mg/kg/day twice a week to experimental group, paclitaxel administration and anti-CXCL16 therapeutic antibody were administered intraperitoneally at 100 meg/20 g/day twice a week to experimental group two, and paclitaxel was injected to experimental group 3 Administration, and PD-L1 inhibitor (peptide) were administered intraperitoneally at 0.1 mg/20 g/day 5 times a week, paclitaxel was injected to experimental group 4, PD-L1 inhibitor (peptide) was injected 5 times a week, and anti-CXCL16 therapeutic antibody was injected twice a week.

Figure 7:
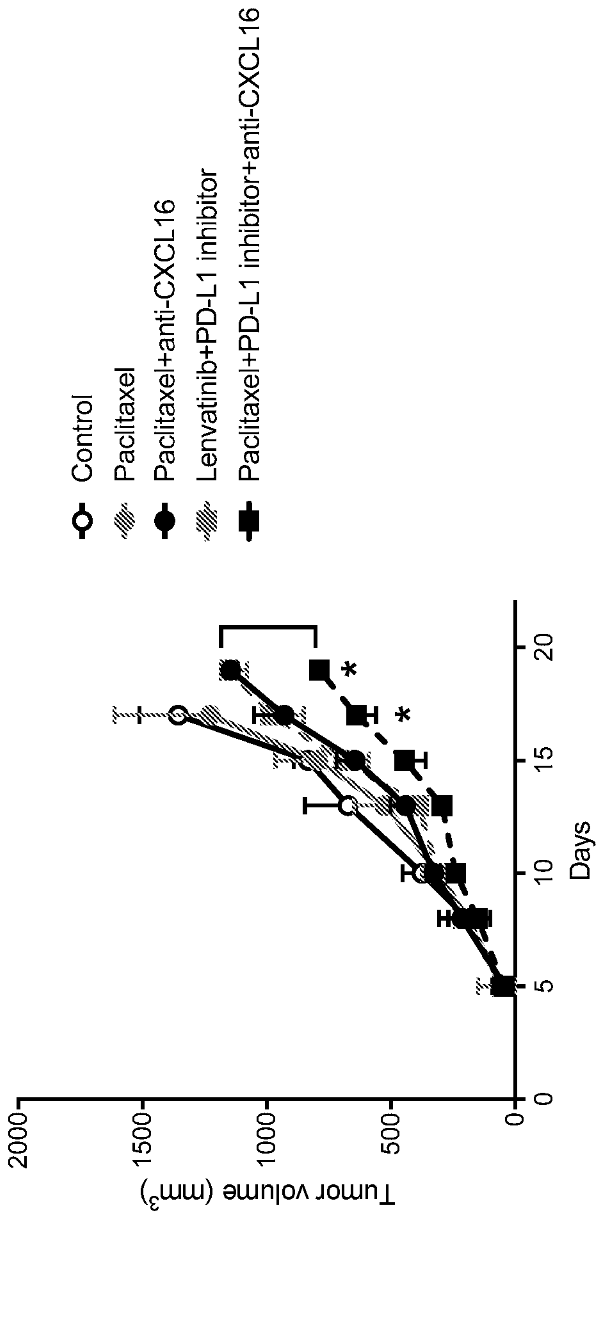
FIG. 7 shows the tumor growth in mice carrying breast cancer treated by a combination therapy of paclitaxel, the PD-L1 inhibitor (immune checkpoint inhibitor), and the anti-mouse CXCL16 antibody.

As shown in FIG. 7, experimental group 1 (Taxol alone) and experimental groups 2 and 3 (two-drug therapy) did not have a clear therapeutic effect, but on the 17th and 19th days of the experiment, paclitaxel+PD-L1 inhibitor+anti-CXCL16 therapeutic antibody (Experimental group 4) showed the best therapeutic effect in the three-drug regimen.

Thus, CXCL16 antibody will show a synergistic effect when combined with a targeted anticancer agent and/or a PD-L1 inhibitor. Therefore, it is expected that the CXCL16 antibody of the present invention, a targeted anticancer agent and/or an immune checkpoint inhibitor can be used in combination to prevent or treat cancer.

Example 6. CXCL16 Antibodies can Inhibit Bone Metastasis in a Mouse Model

1. Higher CXCL16 concentration in bone marrow serum of zolendronic acid (ZA)-resistant bone metastasis The anaplastic thyroid cancer cell line FRO ($2\times10^5$ cells/10 μL PBS) were transplanted into the right tibia of six-week-old female BALB/c nude mice. The mice were divided into a control group and a zoledronic acid (ZA)-treated group. Zoledronic acid is an agent that is known to be effective for treatment of bone metastases. In the ZA-treated group, zolendronic acid (ZA) were injected intravenously at 4 μg/mouse once a week from day 3. Bioluminescence imaging (BLI) were evaluated every week. When observing BLI at 4-5 weeks after cell transplantation, the treatment response to ZA varies. Bone tumor was observed in 7 out of 16 ZA-treated mice. The 9 mice that did not have bone tumor was defined as the "ZA non-resistance (ZA_nonR)" group and the 7 mice that had bone tumor were designated as the "ZA-resistance (ZA-R)" group. ZA_nonR group showed negligible BLI signal in tibia bone till week 7, while ZA-R showed tumor growth from 4-5 to 7 weeks.

Five (5) weeks since the cell transplantation, the initial phase of ZA-R, mice were sacrificed. The bone marrow serum was harvested and CXCL16 concentration was measured using ELISA. The results show that the CXCL16 concentration in ZA_R was significantly higher than that in the ZA_nonR group and the control group. The CXCL16 concentration in the ZA_nonR was lower than that in control group. See FIG. 9B-9C. The results indicate that ZA-resistance in bone metastasis is associated with high CXCL16 concentration.

2. Anti-CXCL16 antibody reduced tumor growth of bone metastasis

Figure 10A:
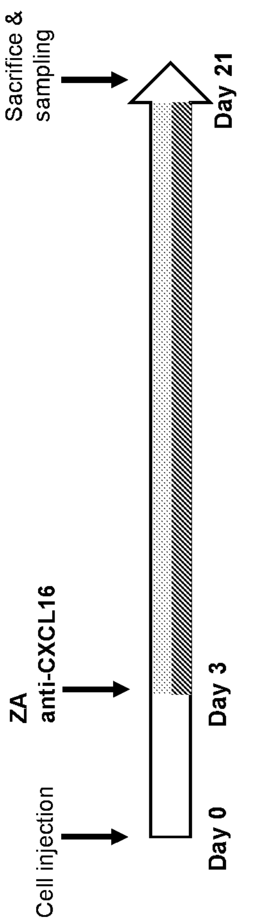
FIGS. 10A, 10B, and 10C show that anti-CXCL16 antibody reduced tumor growth of bone metastasis.
Figure 10B:
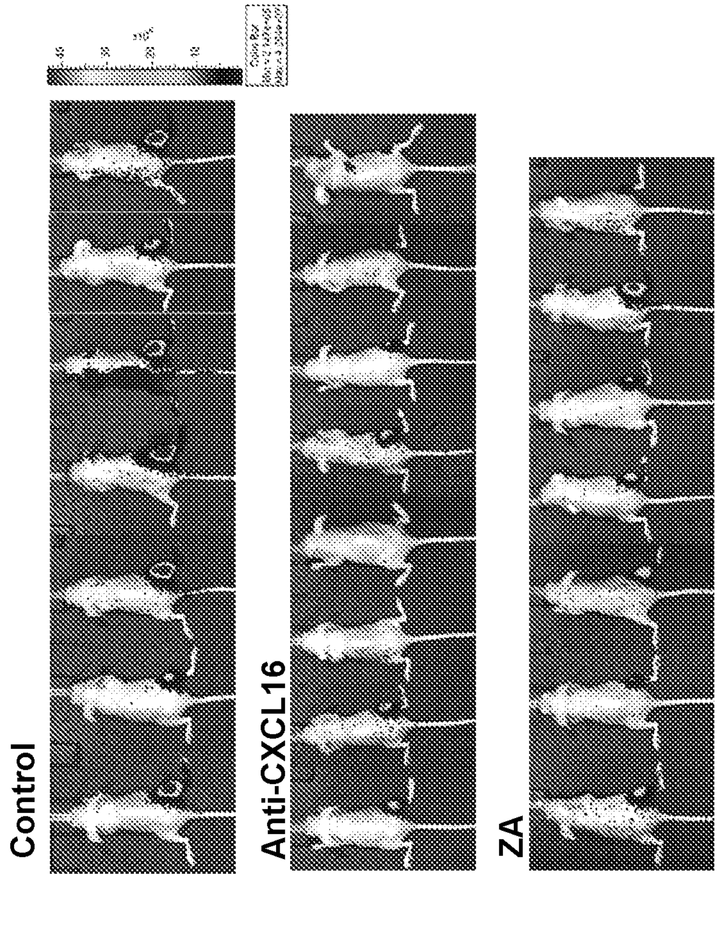
Figure 10C:
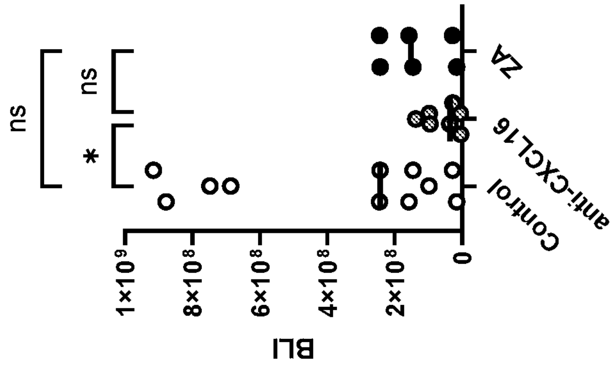

The anaplastic thyroid cancer cell line FRO ($2\times10^5$ cells/10 μL PBS) were transplanted into the right tibia of six-week-old female BALB/c nude mice. At day 3, the mice were divided into the control group, the CXCL16 antibody (aCXCL16) group, and the zoledronic acid (ZA) group. In the CXCL16 group, anti-CXCL16 antibody (a rat IgG against the human CXCL16 protein and the rat IgG with the CDRs of SEQ ID NOs: 12-17) was injected intraperitoneally at 25 μg/mouse once a week. In the ZA-treated group, zolendronic acid (ZA) was injected intravenously at 4 μg/mouse once a week. Bioluminescence imaging (BLI) was evaluated every week. As shown in FIGS. 10B and 10C, at day 21. BLI signals the in the CXCL16 group were significantly lower than that of the control group but were comparable to the that of ZA group. These results indicated that anti-CXCL16 antibody reduced tumor growth of bone metastasis. The results also suggest that the CXCL16 antibody inhibits bone metastasis progression to the extent similar to ZA and CXCL16 antibody has potential therapeutic effects in inhibiting bone metastasis.

3. Treatment of aCXCL16 Reduced Tumor Growth of ZA-Resistant Bone Metastasis

Figure 11A:
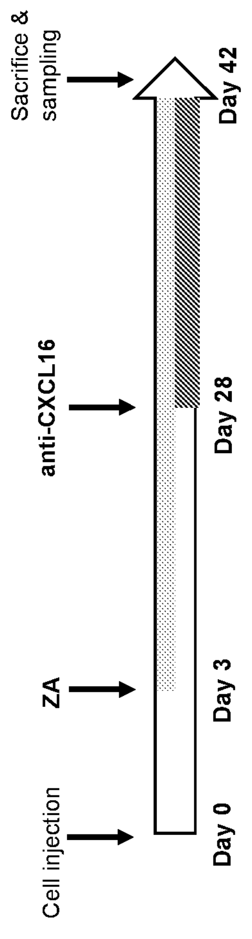
FIGS. 11A, 11B, and 11C shows the results of the treatment of anti-CXCL16 antibodies reduced tumor growth of ZA-resistant bone metastasis.
Figure 11B:
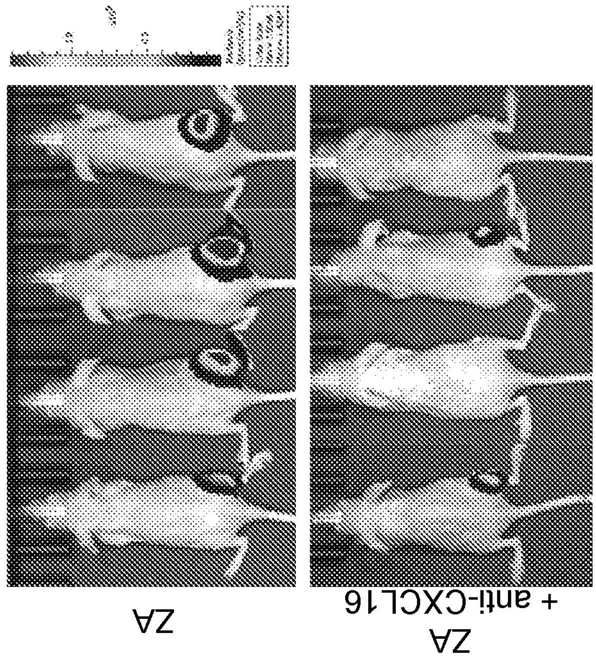
Figure 11C:
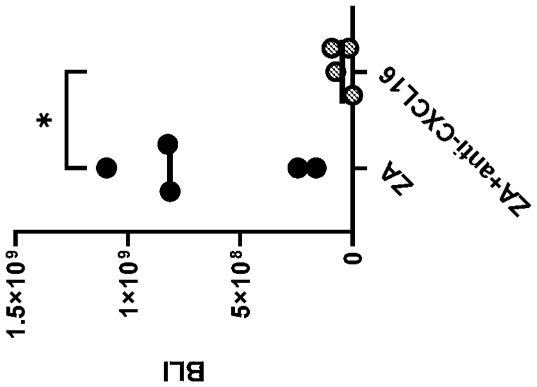

The anaplastic thyroid cancer cell line FRO ($2\times10^5$ cells/10 μL PBS) were transplanted into the right tibia of six-week-old female BALB/c nude mice. At day 3, ZA was injected intravenously at 4 μg/mouse once a week. At day 28, ZA-resistant mice, mice with bone tumor despite ZA treatment, were selected. They were divided into the ZA group and the ZA+aCXCL16 group. In the ZA group, ZA was injected alone, whereas in the ZA+aCXCL16 group, both ZA and anti-human CXCL16 antibody (a rat IgG with the CDRs of SEQ ID NOs 12-17) were injected. The anti-CXCL16 antibody was injected intraperitoneally at 25 μg/mouse once a week from day 28 to day 42 for 2 weeks. Biolumiencence imaging (BLI) were evaluated every week. As shown in FIG. 11A-11C, at day 42, the BLI signals in the ZA+aCXCL16 group were significantly lower than that of the ZA group. These results indicated that anti-CXCL16 antibody reduced ZA-resistant bone tumor growth.

Example 7. Producing Humanized CXCL16 Antibodies

1. Production of Chimeric Antibody HC0LC0

An anti-human CXCL16 antibody raised in rats was obtained. The antibody was sequenced using Mass-Spectrometry and determined to have CDR sequences as disclosed in SEQ ID NOs 12-17. The sequences of a variant of the rat antibody were designed by replacing the constant region sequences of the rat antibody with the constant region sequence of a human IgG1 antibody as further described below. The chimeric antibody is designated as HC0LC0.

DNA sequences (SEQ ID NO: 33 and SEQ ID NO: 35) encoding for the heavy chain and the light chain of the variant antibody (SEQ ID NO: 32 and SEQ ID NO: 34, respectively) were synthesized and cloned into the mammalian transient expression plasmid pETEv2 (TGEX-HC-hG1, TGEX-LC-hk, pOpti VEC, pCDNA3.3, pTRIOz, pFUSECHig, pFUSE-CLig can also be used) (Murine antibody signal peptides MGWTLVFLFLLSVTAGVHS (SEQ ID NO: 18) and MVSSAQFLGLLLLCFQGTRC (SEQ ID NO: 19) were used for the expression of the heavy chain and light chain of the chimeric antibody, respectively, because they can result in higher levels of expression in CHO cells.

The variant antibodies were expressed using CHO cells based transient expression system and the resulting antibody containing cell culture supernatants were collected by centrifugation and filtration. These variant antibodies were purified (using state-of-the-art AKTA chromatography equipment) from cell culture supernatants via affinity chromatography. The purified antibody was buffer exchanged into phosphate buffered saline solution. Finally, chimeric antibody HC0LC0 was purified.

2. Humanization of Chimeric Antibody HC0LC0

The chimeric antibody HC0LC0 variable domains were sequenced and CDRs were identified using a combined IMGT and Kabat antibody numbering systems for optimal retention of CDR-loop conformation. IMGT and Kabat antibody numbering systems are well known, see, for example, Lefranc, M.-P. et al., "IMGT unique numbering for immunoglobulin and T cell receptor variable domains and Ig superfamily V-like domains". Dev. Comp. Immunol., 27, 55-77 (2003) PMID: 12477501 LIGM: 268; and Dunbar J and Deane C M. ANARCI: Antigen receptor numbering and receptor classification. Bioinformatics (2016).

The chimeric antibody HC0LC0 VH domain had the sequence below, which does not include the signal peptide sequence.

```
                                            (SEQ ID NO: 36)
AVQLVESGGGLVQGPKESLKISCAASGFTFSNAVMNWVRGAPGKGLEWVA
RIRTKPNNYATFYADSVKGRFTFSRDDSKSMVYLQMDNLKTEDTAMYYCT
AWTTEGIYWGQGTLVTVSS
(The CDR residues are underlined).
```

The closest human germline gene V-region is *Homo sapiens* IGHV3-73*01:

```
                                            (SEQ ID NO: 37)
EVQLVESGGGLVQPGGSLKLSCAASGFTFSGSAMHWVRQGASGKGLEWVG
RIRSKANSYATAYAASVKGRFTISRDDSKNTAYLQMNSLKTEDTAVYYCT
R
_(the CDR residues are underlined)
```

Databases of Human IgG sequences were searched for comparison to the rodent VH domain using BLAST search algorithms, and candidate human variable domains selected from the top 200 BLAST results. Three human variable domains were selected based on a combination of framework homology, maintaining key framework residues and canonical loop structure, and they are used as acceptor framework. The CDRs of the HC0LC0 VH are then grafted into these acceptor frameworks to generate humanized VH variants. In some cases, back mutations were made to make the antibody more similar to the parental antibody (the rat CXCL16 antibody) while maintaining close similarity to the germline sequence. The CDR residues are underlined.

```
>VH1
                                            (SEQ ID NO: 1)
QVQLVESGGGVVQPGGSLRLSCAASGFTFSNAVMNWVRQAPGKGLEWVA
RIRTKPNNYATFYADSVKGRFTFSRDNSKTMLYLQMNSLRAEDTAVYYC
TAWTTEGIYWGQGTLVTVSS
>VH2
                                            (SEQ ID NO: 2)
AVQLVESGGGLVQPGGSLKISCAASGFTFSNAVMNWVRQASGKGLEWVG
RIRTKPNNYATFYADSVKGRFTISRDDSKNTAYLQMNSLKTEDTAMYYC
TAWTTEGIYWGQGTLVTVSS
>VH3
                                            (SEQ ID NO: 3)
EVQLVESGGGLVQPGGSLKLSCAASGFTFSNAVMNWVRQAPGKGLEWVG
RIRTKPNNYATFYADSVKGRFTFSRDDSKNTAYLQMNILKTEDTAMYYC
TAWTTEGIYWGQGTTVTVSS
>VH4
                                            (SEQ ID NO: 4)
EVQLVESGGGLVKPGGSLRLSCAASGFTFSNAVMNWVRQAPGKGLEWVA
RIRTKPNNYATFYADSVKGRFTFSRDDSKNTLYLQMNSLKTEDTAVYYC
TAWTTEGIYWGQGTTVTVSS
```

-continued

```
>VH5
                                    (SEQ ID NO: 5)
EVQLVESGGGLVQPGGSLKLSCAASGFTFSNAVMNWVRQASGKGLEWVA

RIRTKPNNYATFYADSVKGRFTFSRDDSKNTAYLQMNSLKTEDTAMYYC

TAWTTEGIYWGQGTLVTVSS
```

Similarly, the variable domain of the light chain of the chimeric antibody HC0LC0 was determined using the combined IMGT and Kabat antibody numbering systems for optimal retention of CDR-loop conformation.

The chimeric antibody HC0LC0 VL domain had the sequence below, which does not include the signal peptide sequence.

```
DIVMTQSPSSLAVSAGFTVTINCKSSQSLLYSGNQKNYLAWYQQKPGQSP

KLLIYWASTRQSGVPDRFIGSGSGTDFTLTISSVQAEDLAIYYCQQYYDT

PWTFGGGTKLELK
```

The CDR residues highlighted in yellow were identified using the IMGT numbering system and the CDR residues highlighted in red were identified using the Kabat numbering system.

The closest human germline gene V-region is *Homo sapiens* IGKV4-1*01:

```
DIVMTQSPDSLAVSLGERATINCKSSQSVLYSSNNKNYLAWYQQKPGQPP

KLLIYWASTRESGVPDRFSGSGSGTDFTLTISSLQAEDCVAVYYCQQYYS

TP
```

Databases of Human IgK sequences were searched for comparison to the rat VL domain using BLAST search algorithms, and candidate human variable domains selected from the top 200 BLAST results. These were reduced to two candidates based on a combination of framework homology, maintaining key framework residues and canonical loop structure. With the CDRs of the HC0LC0 VL grafted into these acceptor frameworks they become the humanized variants. VH1-5 contain back mutations to make the antibody more similar to the parental antibody (the rat CXCL16 antibody) while maintaining close similarity to the human germline sequence.

```
>VL1
                                    (SEQ ID NO: 6)
DIVMTQSPDSLAVSAGFTVTINCKSSQSLLYSGNQKNYLAWYQQKPGQS

PKLLIYWASTRQSGVPDRFSGSGSGTDFTLTISSVQAEDVAVYYCQQYY

DTPWTFGGGTKVEIK

>VL2
                                    (SEQ ID NO: 7)
DIVMTQSPSSLAVSLGFTATINCKSSQSLLYSGNQKNYLAWYQQKPGQP

PKLLIYWASTRQSGVPDRFTGSGAGTDFTLTISSVQAEDLAIYYCQQYY

DTPWTFGGGTKVEIK

>VL3
                                    (SEQ ID NO: 8)
DIQMTQSPSSLSASVGDRVTITCKSSQSLLYSGNQKNYLAWYQQKPGQS

PKLLIYWASTRQSGVPDRFSGSGSGTDFTLTISSLQAEDFATYYCQQYY

DTPWTFGGGTKVEIK

>VL4
                                    (SEQ ID NO: 9)
DIQMTQSPSSLSASVGDRVTITCKSSQSLLYSGNQKNYLAWYQQKPGQS

PKLLIYWASTRQSGVPSRFSGSGSGTDFTLTISSLQPEDLAIYYCQQYY

DTPWTFGGGTKLELK

>VL5
                                   (SEQ ID NO: 10)
DIVMTQSPSSLAVSAGERATINCKSSQSLLYSGNQKNYLAWYQQKPGQS

PKLLIYWASTRQSGVPDRFIGSGSGTDFTLTISSLQAEDVAIYYCQQYY

DTPWTFGGGTKLELK
```

3. Humanization Verification

The humanized variants were checked to determine whether they had been humanized in accordance with WHO's definition of humanized antibodies. See, Ehrenmann F., Kaas Q. and Lefranc M.-P. 2010 IMGT/3Dstructure-DB and IMGT/DomainGapAlign: a database and a tool for immunoglobulins or antibodies, T cell receptors, MHC, IgSF and MhcSF Nucleic Acids Res. 38, D301-307. The variable domain of a humanized chain has a V region amino acid sequence which, analyzed as a whole, is closer to human than to other species (assessed using the IMMUNOGENETICS INFORMATION SYSTEM® (IMGT®) DomainGapAlign tool). See Table 7.

TABLE 7

WHO's assigned antibody INN for the HC0LC0 and humanized variants

| Sequence Name | Species | Gene and Allele | Domain Label | Identity (%) | Overlap | WHO INN Designation |
|---|---|---|---|---|---|---|
| VH0 | *Rattus norvegicus* | IGHV10-5*01 | VH | 96.0 | 100 | Rat |
| VH1 | *Homo sapiens* | IGHV3-30*02 | VH | 83.7 | 98 | Humanized |
| VH2 | *Homo sapiens* | IGHV3-73*01 | VH | 88.8 | 98 | Humanized |
| VH3 | *Homo sapiens* | IGHV3-73*01 | VH | 86.9 | 99 | Humanized |
| VH4 | *Homo sapiens* | IGHV3-15*07 | VH | 86.9 | 99 | Humanized |
| VH5 | *Homo sapiens* | IGHV3-73*01 | VH | 87.9 | 99 | Humanized |
| VL0 | *Rattus norvegicus* | IGKV8S6*01 | V-Kappa | 93.1 | 98 | Rat |
| VL1 | *Homo sapiens* | IGKV4-1*01 | V-Kappa | 90.1 | 101 | Humanized |
| VL2 | *Homo sapiens* | IGKV4-1*01 | V-Kappa | 88.1 | 101 | Humanized |
| VL3 | *Homo sapiens* | IGKV4-1*01 | V-Kappa | 84.2 | 101 | Humanized |
| VL4 | *Homo sapiens* | IGKV4-1*01 | V-Kappa | 82.2 | 101 | Humanized |
| VL5 | *Homo sapiens* | IGKV4-1*01 | V-Kappa | 90.1 | 101 | Humanized |

4. T-Cell Epitope Screen

Presentation of peptide sequences in the groove of MHC Class II molecules leads to the activation of CD4+ T-cells and an immunogenic response. To reduce this response, therapeutic proteins can be designed to avoid the incorporation of "T-cell epitopes" that can activate T-cells by lowering the binding affinity to the MHC Class II molecules.

The original rat antibody VH and VL and the humanized variant sequences were screened for MHC II binding peptides to determine that the humanization process had removed peptide sequences with high affinity using in silico algorithms. The following 8 alleles represent over 99% of the world's population and are the standard allele set used for prediction of MHC Class II epitopes: DRB1*01:01; DRB1*03:01; DRB1*04:01; DRB1*07:01; DRB1*08:02; DRB1*11:01; DRB1*13:02; DRB1*15:01. See Wang et al., Peptide binding predictions for HLA DR, DP and DQ molecules. BMC Bioinformatics. 11:568; Gonzalez-Galarza F F, Nucleic Acid Research, 39 (2011), D913-D919; Greenbaum J, et al., Immunogenetics 63 (6): 325-35.

The foregoing description of the present invention is for illustration, and those of ordinary skill in the art to which the present invention pertains can understand that it can be easily modified into other specific forms without changing the technical spirit or essential features of the present invention. Therefore, the embodiments described above are illustrative in all respects but not restrictive.

What is claimed is:

1. An antibody or antigen-binding fragment thereof that binds to CXCL16, comprising:

a heavy chain variable region comprising HCDR1 of SEQ ID NO: 12, HCDR2 of SEQ ID NO: 13, and HCDR3 of SEQ ID NO: 14; and a light chain variable region comprising LCDR1 of SEQ ID NO: 15, LCDR2 of SEQ ID NO: 16, and LCDR3 of SEQ ID NO: 17.

2. The antibody or the antigen-binding fragment of claim 1, wherein the antibody or the antigen-binding fragment competes with CXCR6 (SEQ ID NO: 20) for binding to the CXCL16.

3. The antibody or the antigen-binding fragment of claim 1, wherein the antibody or the antigen-binding fragment further comprises any one selected from a group consisting of following (i) to (v):

(i) a VH region of SEQ ID NO: 4 and a VL region of SEQ ID NO: 6;

(ii) a VH region of SEQ ID NO: 5 and a VL region of SEQ ID NO: 6;

(iii) a VH region of SEQ ID NO: 5 and a VL region of SEQ ID NO: 7;

(iv) a VH region of SEQ ID NO: 5 and a VL region of SEQ ID NO: 8; and (v) a VH region of SEQ ID NO: 5 and a VL region of SEQ ID NO: 10.

4. The antibody or the antigen-binding fragment of claim 1, wherein the antibody is a humanized antibody, a chimeric antibody, a multispecific antibody, or a bispecific antibody.

5. An immunoconjugate comprising the antibody or the antigen-binding fragment of claim 1, and a cytotoxic agent.

6. A polynucleotide encoding the antibody or the antigen-binding fragment of claim 1.

7. An expression vector comprising the polynucleotide of claim 6.

8. A host cell that comprises the expression vector of claim 7.

9. A pharmaceutical composition comprising the antibody or the antigen-binding fragment of claim 1.

10. A method of inducing an immune response and/or treating cancer, the method comprising administering the antibody or the antigen-binding fragment of claim 1.

11. A method for inhibiting tumor metastasis, the method comprising administering the antibody or the antigen-binding fragment of claim 1.

12. The method for inhibiting the tumor metastasis of claim 11, wherein the tumor metastasis is bone metastasis.

13. The method of claim 10, wherein the antibody or the antigen-binding fragment is administered intravenously.

14. A method of treating a cancer patient having a tumor tissue that can be bound by an antibody or the antigen-binding fragment that binds CXCL16, the method comprising administering the antibody or the antigen-binding fragment of claim 1 to the patient.

15. The method of claim 10, wherein the cancer is thyroid cancer or breast cancer.

16. The method of claim 15, wherein the breast cancer is triple-negative breast cancer.

17. The method of claim 11, wherein the antibody is administered intravenously.

18. The method of claim 10, further comprising administering chemotherapy and/or radiation therapy.

19. The method of claim 18, wherein the administering chemotherapy comprises administering paclitaxel.

20. The method of claim 10, further comprising administering an agent that targets an immunological checkpoint antigen.

21. The method of claim 20, wherein the agent is a monoclonal antibody.

22. The method of claim 21, wherein the monoclonal antibody is configured to block PD-1 ligand binding to PD-1.

23. The method of claim 22, wherein the monoclonal antibody is an anti-PD-1 antibody.

24. A method of identifying a patient having a tumor suitable for treatment with an antibody or the antigen-binding fragment thereof that binds CXCL16, wherein the method comprises contacting a tumor sample from the patient with the antibody or the antigen-binding fragment of claim 1, and detecting binding of the antibody to the tumor sample, wherein detection of the binding indicates the patient having a tumor suitable for treatment with the antibody or the antigen-binding fragment thereof that binds CXCL16.

25. A method of producing an antibody, the method comprising culturing the host cell of claim 8 under conditions in which a polynucleotide encoding a heavy chain and a polynucleotide encoding a light chain are expressed.

26. The method of claim 10, wherein the cancer is breast cancer, thyroid cancer, cervical cancer, lung cancer, pancreatic cancer, non-small cell lung cancer, liver cancer, colon cancer, colorectal cancer, bone cancer, skin cancer, skin melanoma, intraocular melanoma, uterine cancer, ovarian cancer, rectal cancer, brain tumor, bladder cancer, blood cancer, stomach cancer, perianal cancer, breast cancer, fallopian tube carcinoma, endometrial carcinoma, vaginal cancer, vulvar carcinoma, Hodgkin's disease, esophageal cancer, small intestine cancer, endocrine adenocarcinoma, parathyroid cancer, adrenal cancer, Soft tissue sarcoma, urethral cancer, penile cancer, prostate cancer, kidney cancer, ureter cancer, renal cell carcinoma, renal pelvic carcinoma, CNS central nervous system tumor, primary CNS lymphoma, spinal cord tumor, or brainstem glioma.

27. The antibody or the antigen-binding fragment of claim 1, wherein the antigen-binding fragment is selected from a group consisting of Fv, Fab, Fab', $F(ab')_2$, scFv, and diabody.

28. The antibody or the antigen-binding fragment of claim 1, wherein the antibody comprises an Fc region.

29. The antibody or the antigen-binding fragment of claim 28, wherein the Fc region comprises at least one mutation that increases serum half-life.

30. The antibody or the antigen-binding fragment of claim 29, wherein the at least one mutation is selected from a group consisting of M252Y/S254T/T256E, T250Q/M428L, N434A, N434H, T307A/E380A/N434A, M428L/N434S, M252Y/M428L, D259I/V308F, N434S, V308W, V308Y, and V308F.

* * * * *

SEQUENCE LISTING

```
Sequence total quantity: 52
SEQ ID NO: 1            moltype = AA  length = 118
FEATURE                 Location/Qualifiers
source                  1..118
                        mol_type = protein
                        organism = synthetic construct
SEQUENCE: 1
QVQLVESGGG VVQPGGSLRL SCAASGFTFS NAVMNWVRQA PGKGLEWVAR IRTKPNNYAT  60
FYADSVKGRF TFSRDNSKTM LYLQMNSLRA EDTAVYYCTA WTTEGIYWGQ GTLVTVSS    118

SEQ ID NO: 2            moltype = AA  length = 118
FEATURE                 Location/Qualifiers
source                  1..118
                        mol_type = protein
                        organism = synthetic construct
SEQUENCE: 2
AVQLVESGGG LVQPGGSLKI SCAASGFTFS NAVMNWVRQA SGKGLEWVGR IRTKPNNYAT  60
FYADSVKGRF TISRDDSKNT AYLQMNSLKT EDTAMYYCTA WTTEGIYWGQ GTLVTVSS    118

SEQ ID NO: 3            moltype = AA  length = 118
FEATURE                 Location/Qualifiers
source                  1..118
                        mol_type = protein
                        organism = synthetic construct
SEQUENCE: 3
EVQLVESGGG LVQPGGSLKL SCAASGFTFS NAVMNWVRQA PGKGLEWVGR IRTKPNNYAT  60
FYADSVKGRF TFSRDDSKNT AYLQMNILKT EDTAMYYCTA WTTEGIYWGQ GTTVTVSS    118

SEQ ID NO: 4            moltype = AA  length = 118
FEATURE                 Location/Qualifiers
source                  1..118
                        mol_type = protein
                        organism = synthetic construct
SEQUENCE: 4
EVQLVESGGG LVKPGGSLRL SCAASGFTFS NAVMNWVRQA PGKGLEWVAR IRTKPNNYAT  60
FYADSVKGRF TFSRDDSKNT LYLQMNSLKT EDTAVYYCTA WTTEGIYWGQ GTTVTVSS    118

SEQ ID NO: 5            moltype = AA  length = 118
FEATURE                 Location/Qualifiers
source                  1..118
                        mol_type = protein
                        organism = synthetic construct
SEQUENCE: 5
EVQLVESGGG LVQPGGSLKL SCAASGFTFS NAVMNWVRQA SGKGLEWVAR IRTKPNNYAT  60
FYADSVKGRF TFSRDDSKNT AYLQMNSLKT EDTAMYYCTA WTTEGIYWGQ GTLVTVSS    118

SEQ ID NO: 6            moltype = AA  length = 113
FEATURE                 Location/Qualifiers
source                  1..113
                        mol_type = protein
                        organism = synthetic construct
SEQUENCE: 6
DIVMTQSPDS LAVSAGETVT INCKSSQSLL YSGNQKNYLA WYQQKPGQSP KLLIYWASTR  60
QSGVPDRFSG SGSGTDFTLT ISSVQAEDVA VYYCQQYYDT PWTFGGGTKV EIK         113

SEQ ID NO: 7            moltype = AA  length = 113
FEATURE                 Location/Qualifiers
source                  1..113
                        mol_type = protein
                        organism = synthetic construct
```

```
SEQUENCE: 7
DIVMTQSPSS LAVSLGETAT INCKSSQSLL YSGNQKNYLA WYQQKPGQPP KLLIYWASTR  60
QSGVPDRFTG SGAGTDFTLT ISSVQAEDLA IYYCQQYYDT PWTFGGGTKV EIK         113

SEQ ID NO: 8           moltype = AA  length = 113
FEATURE                Location/Qualifiers
source                 1..113
                       mol_type = protein
                       organism = synthetic construct
SEQUENCE: 8
DIQMTQSPSS LSASVGDRVT ITCKSSQSLL YSGNQKNYLA WYQQKPGQSP KLLIYWASTR  60
QSGVPDRFSG SGSGTDFTLT ISSLQAEDFA TYYCQQYYDT PWTFGGGTKV EIK         113

SEQ ID NO: 9           moltype = AA  length = 113
FEATURE                Location/Qualifiers
source                 1..113
                       mol_type = protein
                       organism = synthetic construct
SEQUENCE: 9
DIQMTQSPSS LSASVGDRVT ITCKSSQSLL YSGNQKNYLA WYQQKPGQSP KLLIYWASTR  60
QSGVPSRFSG SGSGTDFTLT ISSLQPEDLA IYYCQQYYDT PWTFGGGTKL ELK         113

SEQ ID NO: 10          moltype = AA  length = 113
FEATURE                Location/Qualifiers
source                 1..113
                       mol_type = protein
                       organism = synthetic construct
SEQUENCE: 10
DIVMTQSPSS LAVSAGERAT INCKSSQSLL YSGNQKNYLA WYQQKPGQSP KLLIYWASTR  60
QSGVPDRFIG SGSGTDFTLT ISSLQAEDVA IYYCQQYYDT PWTFGGGTKL ELK         113

SEQ ID NO: 11          moltype = AA  length = 254
FEATURE                Location/Qualifiers
source                 1..254
                       mol_type = protein
                       organism = Homo sapiens
SEQUENCE: 11
MGRDLRPGSR VLLLLLLLLL VYLTQPGNGN EGSVTGSCYC GKRISSDSPP SVQFMNRLRK  60
HLRAYHRCLY YTRFQLLSWS VCGGNKDPWV QELMSCLDLK ECGHAYSGIV AHQKHLLPTS  120
PPISQASEGA SSDIHTPAQM LLSTLQSTQR PTLPVGSLSS DKELTRPNET TIHTAGHSLA  180
AGPEAGENQK QPEKNAGPTA RTSATVPVLC LLAIIFILTA ALSYVLCKRR RGQSPQSSPD  240
LPVHYIPVAP DSNT                                                    254

SEQ ID NO: 12          moltype = AA  length = 10
FEATURE                Location/Qualifiers
source                 1..10
                       mol_type = protein
                       organism = synthetic construct
SEQUENCE: 12
GFTFSNAVMN                                                         10

SEQ ID NO: 13          moltype = AA  length = 19
FEATURE                Location/Qualifiers
source                 1..19
                       mol_type = protein
                       organism = synthetic construct
SEQUENCE: 13
RIRTKPNNYA TFYADSVKG                                               19

SEQ ID NO: 14          moltype = AA  length = 9
FEATURE                Location/Qualifiers
source                 1..9
                       mol_type = protein
                       organism = synthetic construct
SEQUENCE: 14
TAWTTEGIY                                                          9

SEQ ID NO: 15          moltype = AA  length = 17
FEATURE                Location/Qualifiers
source                 1..17
                       mol_type = protein
                       organism = synthetic construct
SEQUENCE: 15
KSSQSLLYSG NQKNYLA                                                 17

SEQ ID NO: 16          moltype = AA  length = 7
FEATURE                Location/Qualifiers
source                 1..7
                       mol_type = protein
```

```
                      organism = synthetic construct
SEQUENCE: 16
WASTRQS                                                    7

SEQ ID NO: 17         moltype = AA  length = 9
FEATURE               Location/Qualifiers
source                1..9
                      mol_type = protein
                      organism = synthetic construct
SEQUENCE: 17
QQYYDTPWT                                                  9

SEQ ID NO: 18         moltype = AA  length = 19
FEATURE               Location/Qualifiers
source                1..19
                      mol_type = protein
                      organism = synthetic construct
SEQUENCE: 18
MGWTLVFLFL LSVTAGVHS                                       19

SEQ ID NO: 19         moltype = AA  length = 20
FEATURE               Location/Qualifiers
source                1..20
                      mol_type = protein
                      organism = synthetic construct
SEQUENCE: 19
MVSSAQFLGL LLLCFQGTRC                                      20

SEQ ID NO: 20         moltype = AA  length = 342
FEATURE               Location/Qualifiers
source                1..342
                      mol_type = protein
                      organism = Homo sapiens
SEQUENCE: 20
MAEHDYHEDY GFSSFNDSSQ EEHQDFLQFS KVFLPCMYLV VFVCGLVGNS LVLVISIFYH  60
KLQSLTDVFL VNLPLADLVF VCTLPFWAYA GIHEWVFGQV MCKSLLGIYT INFYTSMLIL  120
TCITVDRFIV VVKATKAYNQ QAKRMTWGKV TSLLIWVISL LVSLPQIIYG NVFNLDKLIC  180
GYHDEAISTV VLATQMTLGF FLPLLTMIVC YSVIIKTLLH AGGFQKHRSL KIIFLVMAVF  240
LLTQMPFNLM KFIRSTHWEY YAMTSFHYTI MVTEAIAYLR ACLNPVLYAF VSLKFRKNFW  300
KLVKDIGCLP YLGVSHQWKS SEDNSKTFSA SHNVEATSMF QL                    342

SEQ ID NO: 21         moltype = AA  length = 25
FEATURE               Location/Qualifiers
source                1..25
                      mol_type = protein
                      organism = synthetic construct
VARIANT               1
                      note = A, Q, or E
VARIANT               11
                      note = L or V
VARIANT               13
                      note = Q or K
VARIANT               15
                      note = K or G
VARIANT               16
                      note = E or G
VARIANT               19
                      note = K or R
VARIANT               20
                      note = I or L
SEQUENCE: 21
XVQLVESGGG XVXPXXSLXX SCAAS                                25

SEQ ID NO: 22         moltype = AA  length = 14
FEATURE               Location/Qualifiers
source                1..14
                      mol_type = protein
                      organism = synthetic construct
VARIANT               6
                      note = P or S
VARIANT               14
                      note = A or G
SEQUENCE: 22
WVRQAXGKGL EWVX                                            14

SEQ ID NO: 23         moltype = AA  length = 29
FEATURE               Location/Qualifiers
source                1..29
                      mol_type = protein
```

```
                        organism = synthetic construct
VARIANT                 3
                        note = F or I
VARIANT                 7
                        note = D or N
VARIANT                 10
                        note = S, T or N
VARIANT                 11
                        note = M or T
VARIANT                 12
                        note = V, L or A
VARIANT                 17
                        note = D or N
VARIANT                 18
                        note = N, S or I
VARIANT                 20
                        note = K or R
VARIANT                 21
                        note = T or A
VARIANT                 26
                        note = M or V
SEQUENCE: 23
FTXSRDXSKX XXYLQMXXLX XEDTAXYYC                                       29

SEQ ID NO: 24           moltype = AA  length = 11
FEATURE                 Location/Qualifiers
source                  1..11
                        mol_type = protein
                        organism = synthetic construct
VARIANT                 6
                        note = L or T
SEQUENCE: 24
WGQGTXVTVS S                                                          11

SEQ ID NO: 25           moltype = AA  length = 23
FEATURE                 Location/Qualifiers
source                  1..23
                        mol_type = protein
                        organism = synthetic construct
VARIANT                 3
                        note = V or Q
VARIANT                 9
                        note = S or D
VARIANT                 12
                        note = A or S
VARIANT                 13
                        note = V or A
VARIANT                 15
                        note = A, L or V
VARIANT                 17
                        note = E or D
VARIANT                 18
                        note = T or R
VARIANT                 19
                        note = V or A
VARIANT                 22
                        note = N or T
SEQUENCE: 25
DIXMTQSPXS LXXSXGXXXT IXC                                             23

SEQ ID NO: 26           moltype = AA  length = 15
FEATURE                 Location/Qualifiers
source                  1..15
                        mol_type = protein
                        organism = synthetic construct
VARIANT                 9
                        note = S or P
SEQUENCE: 26
WYQQKPGQXP KLLIY                                                      15

SEQ ID NO: 27           moltype = AA  length = 32
FEATURE                 Location/Qualifiers
source                  1..32
                        mol_type = protein
                        organism = synthetic construct
VARIANT                 4
                        note = D or S
VARIANT                 7
                        note = I, S or T
```

```
VARIANT                 11
                        note = S or A
VARIANT                 22
                        note = V or L
VARIANT                 24
                        note = A or P
VARIANT                 27
                        note = L, V or F
VARIANT                 29
                        note = I, V or T
SEQUENCE: 27
GVPXRFXGSG XGTDFTLTIS SXQXEDXAXY YC                          32

SEQ ID NO: 28           moltype = AA  length = 9
FEATURE                 Location/Qualifiers
source                  1..9
                        mol_type = protein
                        organism = synthetic construct
VARIANT                 6
                        note = L or V
VARIANT                 8
                        note = L or I
SEQUENCE: 28
GGGTKXEXK                                                    9

SEQ ID NO: 29           moltype = AA  length = 117
FEATURE                 Location/Qualifiers
source                  1..117
                        mol_type = protein
                        organism = synthetic construct
SEQUENCE: 29
AVQLVESGGG LVQPKESLKI SCAASGFTFS NAVMNWVRQA PGKGLEWVAR IRTKPNNYAT  60
FYADSVKGRF TFSRDDSKSM VYLQMDNLKT EDTAMYYCTA WTTEGIYWGQ GTLVTVS     117

SEQ ID NO: 30           moltype = AA  length = 113
FEATURE                 Location/Qualifiers
source                  1..113
                        mol_type = protein
                        organism = synthetic construct
SEQUENCE: 30
DIVMTQSPSS LAVSAGETVT INCKSSQSLL YSGNQKNYLA WYQQKPGQSP KLLIYWASTR  60
QSGVPDRFIG SGSGTDFTLT ISSVQAEDLA IYYCQQYYDT PWTFGGGTKL ELK         113

SEQ ID NO: 31           moltype = AA  length = 246
FEATURE                 Location/Qualifiers
source                  1..246
                        mol_type = protein
                        organism = Mus sp.
SEQUENCE: 31
MRRGFGPLSL AFFLFLLALL TLPGDGNQGS VAGSCSCDRT ISSGTQIPQG TLDHIRKYLK  60
AFHRCPFFIR FQLQSKSVCG GSQDQWVREL VDCFERKECG TGHGKSFHHQ KHLPQASTQT  120
PEAAEGTPSD TSTPAHSQST QHSTLPSGAL SLNKEHTQPW EMTTLPSGYG LEARPEAEAN  180
EKQQDDRQQE APGAGASTPA WVPVLSLLAI VFFLTAAMAY VLCNRRATQQ NSAGLQLWYT  240
PVEPRP                                                       246

SEQ ID NO: 32           moltype = AA  length = 462
FEATURE                 Location/Qualifiers
source                  1..462
                        mol_type = protein
                        organism = synthetic construct
SEQUENCE: 32
ACCMGWTLVF LFLLSVTAGV HSAVQLVESG GGLVQPKESL KISCAASGFT FSNAVMNWVR  60
QAPGKGLEWV ARIRTKPNNY ATFYADSVKG RFTFSRDDSK SMVYLQMDNL KTEDTAMYYC  120
TAWTTEGIYW GQGTLVTVSS AETTAPSVYP LAPGTALKSN SMVTLGCLVK GYFPEPVTVT  180
WNSGALSSGV HTFPAVLQSG LYTLTSSVTV PSSTWSSQAV TCNVAHPASS TKVDKKIVPR  240
ECNPCGCTGS EVSSVFIFPP KTKDVLTITL TPKVTCVVVD ISQNDPEVRF SWFIDDVEVH  300
TAQTHAPEKQ SNSTLRSVSE LPIVHRDWLN GKTFKCKVNS GAFPAPIEKS ISKPEGTPRG  360
PQVYTMAPPK EEMTQSQVSI TCMVKGFYPP DIYTEWKMNG QPQENYKNTP PTMDTDGSYF  420
LYSKLNVKKE TWQQGNTFTC SVLHEGLHNH HTEKSLSHSP GK                462

SEQ ID NO: 33           moltype = DNA  length = 1380
FEATURE                 Location/Qualifiers
source                  1..1380
                        mol_type = other DNA
                        organism = synthetic construct
SEQUENCE: 33
accatgggct ggaccctggt gttcctgttc ctgctaagcg tgacggcggg cgtccactcc  60
gctgtgcaac tcgtggagag cggcggcggc ctggtgcagc ctaaggagag cctgaagatc  120
agctgcgccg ctagcggctt cacattcagc aacgccgtga tgaactgggt gagacaagcc  180
```

```
cctggcaagg gcctggagtg ggtggctaga atcagaacca agcctaacaa ctacgccacc  240
ttctacgccg acagcgtgaa gggcagattt acgttcagca gagatgacag caagagcatg  300
gtgtacctgc agatggacaa cctgaagacc gaggacaccg ccatgtacta ctgcaccgcc  360
tggaccaccg agggcatcta ctggggccaa ggcaccctgg tgaccgtgag cagcgccgag  420
accaccgccc ctagcgtgta ccctctggcc cctggcaccg ccctgaaaag caatagcatg  480
gtgaccctgg gctgccttgt gaagggctat ttccctgagc ctgtgaccgt gacctggaac  540
tccggcgccc tgagcagcgg cgtgcacacc ttccctgccg tgctgcagag cggcctgtac  600
accctgacaa gcagcgtgac cgtgcctagc agcacctgga gcagccaagc cgtgacctgc  660
aacgtggccc accctgctag cagcaccaag gtggacaaga agatcgtgcc tagagagtgc  720
aacccttgcg gctgcaccgg cagcgaggtg agcagcgtgt tcatcttccc tcctaagacc  780
aaggacgtgc tgaccatcac cctgacccct aaggtgacct gcgtggtggt ggacatctct  840
cagaacgacc ctgaggtgag attcagctgg ttcatcgacg acgtggaggt gcacaccgct  900
cagacccacg cccctgagaa gcaaagcaac agcaccctta gaagcgtgag cgagctgcct  960
atcgtgcaca gagactggct gaacggcaag accttcaagt gcaaggtgaa cagcggcgcc  1020
ttccctgccc ctatcgagaa gagcatcagc aagcctgagg gcacccctag aggccctcaa  1080
gtgtacacca tggcccctcc taaggaggag atgacacaga gccaagtgag catcacctgc  1140
atggtgaaag gcttctaccc tcctgacatc tacaccgagt ggaagatgaa cggacagcct  1200
caagagaact acaagaacac ccctcctacc atggacaccg acggcagcta cttcctgtac  1260
agcaagctga acgtgaagaa ggagacctgg cagcaaggca acaccttcac ctgcagcgtg  1320
ctgcacgagg gcctgcacaa ccaccacacc gagaagagcc tgagccacag ccctggcaag  1380

SEQ ID NO: 34          moltype = AA  length = 243
FEATURE                Location/Qualifiers
source                 1..243
                       mol_type = protein
                       organism = synthetic construct
SEQUENCE: 34
ACCMVSSAQF LGLLLLCFQG TRCDIVMTQS PSSLAVSAGE TVTINCKSSQ SLLYSGNQKN  60
YLAWYQQKPG QSPKLLIYWA STRQSGVPDR FIGSGSGTDF TLTISSVQAE DLAIYYCQQY  120
YDTPWTFGGG TKLELKRADA APTVSIFPPS TEQLATGGAS VVCLMNNFYP RDISVKWKID  180
GTERRDGVLD SVTDQDSKDS TYSMSSTLSL TKADYESHNL YTCEVVHKTS SSPVVKSFNR  240
NEC                                                               243

SEQ ID NO: 35          moltype = DNA  length = 723
FEATURE                Location/Qualifiers
source                 1..723
                       mol_type = other DNA
                       organism = synthetic construct
SEQUENCE: 35
accatggtga gcagcgctca gttcctgggc ctgctgctgc tgtgcttcca aggcacaaga  60
tgcgacatcg tgatgacaca gagccctagc agcctggccg tgagcgccgg cgagaccgtg  120
accatcaact gcaagagctc tcagagcctg ctgtacagcg gcaatcagaa gaactacctg  180
gcctggtatc agcagaagcc tggacagagc cctaagctgc tgatctactg ggctagcaca  240
agacagagcg gcgtgcctga cagattcatc ggcagcggca gcggcaccga cttcaccctg  300
accatcagca gcgtgcaagc cgaggacctg gccatctact actgtcagca gtactacgac  360
accccttgga ccttcggcgg cggcaccaag ctggagctga agagagccga cgccgcccct  420
accgtgagca tcttccctcc tagcaccgag cagctggcca ccggcggcgc tagcgtggtg  480
tgcctgatga acaacttcta ccctagagac atcagcgtga agtggaagat cgacggcacc  540
gagagaagag acggcgtgct ggacagcgtg accgaccaag acagcaagga cagcacctac  600
agcatgagca gcaccctgag cctgaccaag gccgactacg agagccacaa cctgtacacc  660
tgcgaggtgg tgcacaagac aagcagcagc cctgtggtga agagcttcaa cagaaacgag  720
tgc                                                               723

SEQ ID NO: 36          moltype = AA  length = 119
FEATURE                Location/Qualifiers
source                 1..119
                       mol_type = protein
                       organism = synthetic construct
SEQUENCE: 36
AVQLVESGGG LVQGPKESLK ISCAASGFTF SNAVMNWVRG APGKGLEWVA RIRTKPNNYA  60
TFYADSVKGR FTFSRDDSKS MVYLQMDNLK TEDTAMYYCT AWTTEGIYWG QGTLVTVSS   119

SEQ ID NO: 37          moltype = AA  length = 101
FEATURE                Location/Qualifiers
source                 1..101
                       mol_type = protein
                       organism = Homo sapiens
SEQUENCE: 37
EVQLVESGGG LVQPGGSLKL SCAASGFTFS GSAMHWVRQG ASGKGLEWVG RIRSKANSYA  60
TAYAASVKGR FTISRDDSKN TAYLQMNSLK TEDTAVYYCT R                     101

SEQ ID NO: 38          moltype = AA  length = 448
FEATURE                Location/Qualifiers
source                 1..448
                       mol_type = protein
                       organism = synthetic construct
SEQUENCE: 38
QVQLVESGGG VVQPGGSLRL SCAASGFTFS NAVMNWVRQA PGKGLEWVAR IRTKPNNYAT  60
FYADSVKGRF TFSRDNSKTM LYLQMNSLRA EDTAVYYCTA WTTEGIYWGQ GTLVTVSSAS  120
```

-continued

```
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 39          moltype = AA  length = 448
FEATURE                Location/Qualifiers
source                 1..448
                       mol_type = protein
                       organism = synthetic construct
SEQUENCE: 39
AVQLVESGGG LVQPGGSLKI SCAASGFTFS NAVMNWVRQA SGKGLEWVGR IRTKPNNYAT  60
FYADSVKGRF TISRDDSKNT AYLQMNSLKT EDTAMYYCTA WTTEGIYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 40          moltype = AA  length = 448
FEATURE                Location/Qualifiers
source                 1..448
                       mol_type = protein
                       organism = synthetic construct
SEQUENCE: 40
EVQLVESGGG LVQPGGSLKL SCAASGFTFS NAVMNWVRQA PGKGLEWVGR IRTKPNNYAT  60
FYADSVKGRF TFSRDDSKNT AYLQMNILKT EDTAMYYCTA WTTEGIYWGQ GTTVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 41          moltype = AA  length = 448
FEATURE                Location/Qualifiers
source                 1..448
                       mol_type = protein
                       organism = synthetic construct
SEQUENCE: 41
EVQLVESGGG LVKPGGSLRL SCAASGFTFS NAVMNWVRQA PGKGLEWVAR IRTKPNNYAT  60
FYADSVKGRF TFSRDDSKNT LYLQMNSLKT EDTAVYYCTA WTTEGIYWGQ GTTVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 42          moltype = AA  length = 448
FEATURE                Location/Qualifiers
source                 1..448
                       mol_type = protein
                       organism = synthetic construct
SEQUENCE: 42
EVQLVESGGG LVQPGGSLKL SCAASGFTFS NAVMNWVRQA SGKGLEWVAR IRTKPNNYAT  60
FYADSVKGRF TFSRDDSKNT AYLQMNSLKT EDTAMYYCTA WTTEGIYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 43          moltype = AA  length = 220
FEATURE                Location/Qualifiers
source                 1..220
                       mol_type = protein
                       organism = synthetic construct
SEQUENCE: 43
DIVMTQSPDS LAVSAGETVT INCKSSQSLL YSGNQKNYLA WYQQKPGQSP KLLIYWASTR  60
QSGVPDRFSG SGSGTDFTLT ISSVQAEDVA VYYCQQYYDT PWTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 44          moltype = AA  length = 220
```

```
FEATURE                 Location/Qualifiers
source                  1..220
                        mol_type = protein
                        organism = synthetic construct
SEQUENCE: 44
DIVMTQSPSS LAVSLGETAT INCKSSQSLL YSGNQKNYLA WYQQKPGQPP KLLIYWASTR  60
QSGVPDRFTG SGAGTDFTLT ISSVQAEDLA IYYCQQYYDT PWTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 45           moltype = AA  length = 220
FEATURE                 Location/Qualifiers
source                  1..220
                        mol_type = protein
                        organism = synthetic construct
SEQUENCE: 45
DIQMTQSPSS LSASVGDRVT ITCKSSQSLL YSGNQKNYLA WYQQKPGQSP KLLIYWASTR  60
QSGVPDRFSG SGSGTDFTLT ISSLQAEDFA TYYCQQYYDT PWTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 46           moltype = AA  length = 220
FEATURE                 Location/Qualifiers
source                  1..220
                        mol_type = protein
                        organism = synthetic construct
SEQUENCE: 46
DIQMTQSPSS LSASVGDRVT ITCKSSQSLL YSGNQKNYLA WYQQKPGQSP KLLIYWASTR  60
QSGVPSRFSG SGSGTDFTLT ISSLQPEDLA IYYCQQYYDT PWTFGGGTKL ELKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 47           moltype = AA  length = 220
FEATURE                 Location/Qualifiers
source                  1..220
                        mol_type = protein
                        organism = synthetic construct
SEQUENCE: 47
DIVMTQSPSS LAVSAGERAT INCKSSQSLL YSGNQKNYLA WYQQKPGQSP KLLIYWASTR  60
QSGVPDRFIG SGSGTDFTLT ISSLQAEDVA IYYCQQYYDT PWTFGGGTKL ELKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 48           moltype = AA  length = 330
FEATURE                 Location/Qualifiers
source                  1..330
                        mol_type = protein
                        organism = Homo sapiens
SEQUENCE: 48
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 49           moltype = AA  length = 107
FEATURE                 Location/Qualifiers
source                  1..107
                        mol_type = protein
                        organism = Homo sapiens
SEQUENCE: 49
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                 107

SEQ ID NO: 50           moltype = AA  length = 8
FEATURE                 Location/Qualifiers
source                  1..8
                        mol_type = protein
                        organism = synthetic construct
SEQUENCE: 50
GFTFSNAV                                                          8

SEQ ID NO: 51           moltype = AA  length = 5
FEATURE                 Location/Qualifiers
source                  1..5
                        mol_type = protein
                        organism = synthetic construct
SEQUENCE: 51
```

-continued

```
NAVMN                                                              5

SEQ ID NO: 52           moltype = AA  length = 102
FEATURE                 Location/Qualifiers
source                  1..102
                        mol_type = protein
                        organism = Homo sapiens
SEQUENCE: 52
DIVMTQSPDS LAVSLGERAT INCKSSQSVL YSSNNKNYLA WYQQKPGQPP KLLIYWASTR  60
ESGVPDRFSG SGSGTDFTLT ISSLQAEDCV AVYYCQQYYS TP                    102
```